US006852536B2

(12) United States Patent
Dobie

(10) Patent No.: US 6,852,536 B2
(45) Date of Patent: Feb. 8, 2005

(54) ANTISENSE MODULATION OF CD36L 1 EXPRESSION

(75) Inventor: Kenneth W. Dobie, Del Mar, CA (US)

(73) Assignee: ISIS Pharmaceuticals, Inc., Carlsbad, CA (US)

( * ) Notice: Subject to any disclaimer, the term of this patent is extended or adjusted under 35 U.S.C. 154(b) by 0 days.

(21) Appl. No.: 10/024,396

(22) Filed: Dec. 18, 2001

(65) Prior Publication Data

US 2003/0147864 A1 Aug. 7, 2003

(51) Int. Cl.[7] .......................... A61K 48/00; C07H 21/04

(52) U.S. Cl. ........................... 435/375; 435/6; 435/325; 536/23.1; 536/24.5

(58) Field of Search ............................... 514/44; 435/6, 435/375, 325; 536/24.5

(56) References Cited

U.S. PATENT DOCUMENTS

| | | | | |
|---|---|---|---|---|
| 5,801,154 A | * | 9/1998 | Baracchini et al. ............ | 514/44 |
| 5,962,322 A | | 10/1999 | Kozarsky et al. ............ | 435/375 |
| 5,965,790 A | * | 10/1999 | Acton .......................... | 435/29 |
| 6,008,014 A | * | 12/1999 | Gimeno et al. ............. | 435/69.1 |
| 6,130,041 A | | 10/2000 | Acton ........................... | 435/6 |
| 6,261,760 B1 | * | 7/2001 | Fielding et al. ................ | 435/4 |

FOREIGN PATENT DOCUMENTS

| | | | |
|---|---|---|---|
| WO | WO 99/11288 | | 3/1999 |
| WO | WO 00/77214 | * | 12/2000 |
| WO | WO 02/34883 | * | 5/2002 |

OTHER PUBLICATIONS

Calvo, D. et al. J. Biochem. Sep. 1993 268(25) 18929–18935.*
Branch, A. D., (1998). Trends Biochem Sci. 1998 Feb.;23(2):45–50.*
Gewirtz et al., Proc. Natl. Acad. Sci. v 93, pp. 3161–3163.*
Agrawal, S. Trends Biotechnol. Oct. 1996;14(10):376–87.*
Tamm, I. et al. The Lancet. 2001, Aug. 358: 489–497.*
Braasch, D. A. Biochemistry. Apr. 2002; 41(14): 4503–4510.*
Acton et al., *Identification of scavenger receptor SR–BI as a high density lipoprotein receptor*, Science, 1996, 271:518–520.
Acton et al., *The HDL receptor SR–BI: a new therapeutic target for atherosclerosis?*, Mol. Med. Today, 1999, 5:518–524.
Acton et al., *Expression cloning of SR–BI, a CD36–related class B scavenger receptor*, J. Biol. Chem., 1994, 269:21003–21009.
Buechler et al., *Lipopolysaccharide inhibits the expression of the scavenger receptor Cla–1 in human monocytes and macrophages*, Biochem. Biophys. Res. Commun., 1999, 262:251–254.

Calvo et al., *The CD36, CLA–1 (CD36L1), and LIMPII (CD36L2) gene family: cellular distribution, chromosomal location, and genetic evolution*, Genomics, 1995, 25:100–106.
Calvo et al., *Human CD36 is a high affinity receptor for the native lipoproteins HDL, LDL, and VLDL*, J. Lipid Res., 1998, 39:777–788.
Calvo et al., *Identification, primary structure, and distribution of CLA–1, a novel member of the CD36/LIMPII gene family*, J. Biol. Chem., 1993, 268:18929–18935.
Cao et al., *Structure and localization of the human gene encoding SR–BI/CLA–1. Evidence for transcriptional control by steroidogenic factor 1*, J. Biol. Chem., 1997, 272:33068–33076.
Chinetti et al., *CLA–1/SR–BI is expressed in atherosclerotic lesion macrophages and regulated by activators of peroxisome proliferator–activated receptors*, Circulation, 2000, 101:2411–2417.
Fukasawa et al., *SRB1, a class B scavenger receptor, recognizes both negatively charged liposomes and apoptotic cells*, Exp. Cell Res., 1996, 222:246–250.
Ikemoto et al., *Identification of a PDZ–domain–containing protein that interacts with the scavenger receptor class B type I*, Proc. Natl. Acad. Sci. U. S. A., 2000, 97:6538–6543.
Imachi et al., *Expression of HDL receptor, CLA–1 in human smooth–muscle cells and effect of interferon–gamma on its regulation*, Horm. Metab. Res., 2001, 33:389–393.
Imachi et al., *Human scavenger receptor B1 is involved in recognition of apoptotic thymocytes by thymic nurse cells*, Lab. Invest., 2000, 80:263–270.
Krieger, *The "best" of cholesterols, the "worst" of cholesterols: a tale of two receptors*, Proc. Natl. Acad. Sci. U. S. A., 1998, 95:4077–4080.
Liu et al., *Ribonucleic acid expression of the CLA–1 gene, a human homolog to mouse high density lipoprotein receptor SR–BI, in human adrenal tumors and cultured adrenal cells*, J. Clin. Endocrinol. Metab., 1997, 82:2522–2527.
Murao et al., *Characterization of CLA–1, a human homologue of rodent scavenger receptor BI, as a receptor for high density lipoprotein and apoptotic thymocytes*, J. Biol. Chem., 1997, 272:17551–17557.
Pussinen et al., *The human breast carcinoma cell line HBL–100 acquires exogenous cholesterol from high–density lipoprotein via CLA–1 (CD–36 and LIMPII analogous 1)—mediated selective cholesteryl ester uptake*, Biochem. J., 2000, 349:559–566.

(List continued on next page.)

*Primary Examiner*—John L. LeGuyader
*Assistant Examiner*—J D Schultz
(74) *Attorney, Agent, or Firm*—Licata & Tyrrell P.C.

(57) ABSTRACT

Antisense compounds, compositions and methods are provided for modulating the expression of CD36L1. The compositions comprise antisense compounds, particularly antisense oligonucleotides, targeted to nucleic acids encoding CD36L1. Methods of using these compounds for modulation of CD36L1 expression and for treatment of diseases associated with expression of CD36L1 are provided.

10 Claims, No Drawings

OTHER PUBLICATIONS

Rigotti et al., *The class B scavenger receptors SR–BI and CD36 are receptors for anionic phospholipids*, The Journal of BIological Chemistry, 1995, 270:16221–16224.

Sehayek et al., *Biliary cholesterol excretion: a novel mechanism that regulates dietary cholesterol absorption*, Proc. Natl. Acad. Sci. U. S. A., 1998, 95:10194–10199.

Stangl et al., *Transport of lipids from high and low density lipoproteins via scavenger receptor–BI*, J. Biol. Chem., 1999, 274:32692–32698.

Trigatti et al., *Influence of the high density lipoprotein receptor SR–BI on reproductive and cardiovascular pathophysiology*, Proc. Natl. Acad. Sci. U. S. A., 1999, 96:9322–9327.

\* cited by examiner

SEQUENCE LISTING

```
<160> NUMBER OF SEQ ID NOS: 91

<210> SEQ ID NO 1
<211> LENGTH: 20
<212> TYPE: DNA
<213> ORGANISM: Artificial Sequence
<220> FEATURE:
<223> OTHER INFORMATION: Antisense Oligonucleotide

<400> SEQUENCE: 1
tccgtcatcg ctcctcaggg                                            20

<210> SEQ ID NO 2
<211> LENGTH: 20
<212> TYPE: DNA
<213> ORGANISM: Artificial Sequence
<220> FEATURE:
<223> OTHER INFORMATION: Antisense Oligonucleotide

<400> SEQUENCE: 2
atgcattctg cccccaagga                                            20

<210> SEQ ID NO 3
<211> LENGTH: 2566
<212> TYPE: DNA
<213> ORGANISM: Homo sapiens
<220> FEATURE:
<221> NAME/KEY: CDS
<222> LOCATION: (70)...(1599)

<400> SEQUENCE: 3
cgtcgccgtc cccgtctcct gccaggcgcg gagccctgcg agccgcgggt gggccccagg      60 cgcgcagac atg ggc tgc tcc gcc aaa gcg cgc tgg gct gcc ggg gcg ctg     111
           Met Gly Cys Ser Ala Lys Ala Arg Trp Ala Ala Gly Ala Leu
             1               5                  10 ggc gtc gcg ggg cta ctg tgc gct gtg ctg ggc gct gtc atg atc gtg      159
Gly Val Ala Gly Leu Leu Cys Ala Val Leu Gly Ala Val Met Ile Val
 15                  20                  25                  30 atg gtg ccg tcg ctc atc aag cag cag gtc ctt aag aac gtg cgc atc      207
Met Val Pro Ser Leu Ile Lys Gln Gln Val Leu Lys Asn Val Arg Ile
                 35                  40                  45 gac ccc agt agc ctg tcc ttc aac atg tgg aag gag atc cct atc ccc      255
Asp Pro Ser Ser Leu Ser Phe Asn Met Trp Lys Glu Ile Pro Ile Pro
             50                  55                  60 ttc tat ctc tcc gtc tac ttc ttt gac gtc atg aac ccc agc gag atc      303
Phe Tyr Leu Ser Val Tyr Phe Phe Asp Val Met Asn Pro Ser Glu Ile
         65                  70                  75 ctg aag ggc gag aag ccg cag gtg cgg gag cgc ggg ccc tac gtg tac      351
Leu Lys Gly Glu Lys Pro Gln Val Arg Glu Arg Gly Pro Tyr Val Tyr
     80                  85                  90 agg gag tcc agg cac aaa agc aac atc acc ttc aac aac aac gac acc      399
Arg Glu Ser Arg His Lys Ser Asn Ile Thr Phe Asn Asn Asn Asp Thr
```

```
                 95                  100                 105                 110
gtg tcc ttc ctc gag tac cgc acc ttc cag ttc cag ccc tcc aag tcc          447
Val Ser Phe Leu Glu Tyr Arg Thr Phe Gln Phe Gln Pro Ser Lys Ser
                115                 120                 125 cac ggc tcg gag agc gac tac atc gtc atg ccc aac atc ctg gtc ttg          495
His Gly Ser Glu Ser Asp Tyr Ile Val Met Pro Asn Ile Leu Val Leu
            130                 135                 140 ggt gcg gcg gtg atg atg gag aat aag ccc atg acc ctg aag ctc atc          543
Gly Ala Ala Val Met Met Glu Asn Lys Pro Met Thr Leu Lys Leu Ile
        145                 150                 155 atg acc ttg gca ttc acc acc ctc ggc gaa cgt gcc ttc atg aac cgc          591
Met Thr Leu Ala Phe Thr Thr Leu Gly Glu Arg Ala Phe Met Asn Arg
    160                 165                 170 act gtg ggt gag atc atg tgg ggc tac aag gac ccc ctt gtg aat ctc          639
Thr Val Gly Glu Ile Met Trp Gly Tyr Lys Asp Pro Leu Val Asn Leu
175                 180                 185                 190 atc aac aag tac ttt cca ggc atg ttc ccc ttc aag gac aag ttc gga          687
Ile Asn Lys Tyr Phe Pro Gly Met Phe Pro Phe Lys Asp Lys Phe Gly
                195                 200                 205 tta ttt gct gag ctc aac aac tcc gac tct ggg ctc ttc acg gtg ttc          735
Leu Phe Ala Glu Leu Asn Asn Ser Asp Ser Gly Leu Phe Thr Val Phe
            210                 215                 220 acg ggg gtc cag aac atc agc agg atc cac ctc gtg gac aag tgg aac          783
Thr Gly Val Gln Asn Ile Ser Arg Ile His Leu Val Asp Lys Trp Asn
        225                 230                 235 ggg ctg agc aag gtt gac ttc tgg cat tcc gat cag tgc aac atg atc          831
Gly Leu Ser Lys Val Asp Phe Trp His Ser Asp Gln Cys Asn Met Ile
    240                 245                 250 aat gga act tct ggg caa atg tgg ccg ccc ttc atg act cct gag tcc          879
Asn Gly Thr Ser Gly Gln Met Trp Pro Pro Phe Met Thr Pro Glu Ser
255                 260                 265                 270 tcg ctg gag ttc tac agc ccg gag gcc tgc cga tcc atg aag cta atg          927
Ser Leu Glu Phe Tyr Ser Pro Glu Ala Cys Arg Ser Met Lys Leu Met
                275                 280                 285 tac aag gag tca ggg gtg ttt gaa ggc atc ccc acc tat cgc ttc gtg          975
Tyr Lys Glu Ser Gly Val Phe Glu Gly Ile Pro Thr Tyr Arg Phe Val
            290                 295                 300 gct ccc aaa acc ctg ttt gcc aac ggg tcc atc tac cca ccc aac gaa         1023
Ala Pro Lys Thr Leu Phe Ala Asn Gly Ser Ile Tyr Pro Pro Asn Glu
        305                 310                 315 ggc ttc tgc ccg tgc ctg gag tct gga att cag aac gtc agc acc tgc         1071
Gly Phe Cys Pro Cys Leu Glu Ser Gly Ile Gln Asn Val Ser Thr Cys
    320                 325                 330 agg ttc agt gcc ccc ttg ttt ctc tcc cat cct cac ttc ctc aac gcc         1119
Arg Phe Ser Ala Pro Leu Phe Leu Ser His Pro His Phe Leu Asn Ala
335                 340                 345                 350 gac ccg gtt ctg gca gaa gcg gtg act ggc ctg cac cct aac cag gag         1167
Asp Pro Val Leu Ala Glu Ala Val Thr Gly Leu His Pro Asn Gln Glu
                355                 360                 365 gca cac tcc ttg ttc ctg gac atc cac ccg gtc acg gga atc ccc atg         1215
Ala His Ser Leu Phe Leu Asp Ile His Pro Val Thr Gly Ile Pro Met
            370                 375                 380 aac tgc tct gtg aaa ctg cag ctg agc ctc tac atg aaa tct gtc gca         1263
Asn Cys Ser Val Lys Leu Gln Leu Ser Leu Tyr Met Lys Ser Val Ala
        385                 390                 395 ggc att gga caa act ggg aag att gag cct gtg gtc ctg ccg ctg ctc         1311
Gly Ile Gly Gln Thr Gly Lys Ile Glu Pro Val Val Leu Pro Leu Leu
    400                 405                 410 tgg ttt gca gag agc ggg gcc atg gag ggg gag act ctt cac aca ttc         1359
```

```
Trp Phe Ala Glu Ser Gly Ala Met Glu Gly Glu Thr Leu His Thr Phe
415                 420                 425                 430 tac act cag ctg gtg ttg atg ccc aag gtg atg cac tat gcc cag tac     1407
Tyr Thr Gln Leu Val Leu Met Pro Lys Val Met His Tyr Ala Gln Tyr
                435                 440                 445 gtc ctc ctg gcg ctg ggc tgc gtc ctg ctg gtc cct gtc atc tgc         1455
Val Leu Leu Ala Leu Gly Cys Val Leu Leu Val Pro Val Ile Cys
            450                 455                 460 caa atc cgg agc caa gag aaa tgc tat tta ttt tgg agt agt agt aaa     1503
Gln Ile Arg Ser Gln Glu Lys Cys Tyr Leu Phe Trp Ser Ser Ser Lys
        465                 470                 475 aag ggc tca aag gat aag gag gcc att cag gcc tat tct gaa tcc ctg     1551
Lys Gly Ser Lys Asp Lys Glu Ala Ile Gln Ala Tyr Ser Glu Ser Leu
    480                 485                 490 atg aca tca gct ccc aag ggc tct gtg ctg cag gaa gca aaa ctg tag     1599
Met Thr Ser Ala Pro Lys Gly Ser Val Leu Gln Glu Ala Lys Leu
495                 500                 505
```

```
ggtcctgagg acaccgtgag ccagccaggc ctggccgctg ggcctgaccg gccccccagc    1659
ccctacaccc cgcttctccc ggactctccc agcagacagc cccccagccc acagcctga    1719 gcctcccagc tgccatgtgc ctgttgcaca cctgcacaca cgccctggca cacatacaca   1779
catgcgtgca ggcttgtgca gacactcagg gatggagctg ctgctgaagg gacttgtagg   1839
gagaggctcg tcaacaagca ctgttctgga accttctctc cacgtggccc acaggctgac   1899
cacaggggct gtgggtcctg cgtcccttc ctcgggtgag cctggcctgt cccgttcagc    1959
cgttgggcca ggcttcctcc cctccaaggt gaaacactgc agtcccggtg tggtggctcc   2019
ccatgcagga cgggccaggc tgggagtgcc gccttcctgt gccaaattca gtggggactc   2079
agtgcccagg ccctggcacg agctttggcc ttggtctacc tgccaggcca ggcaaagcgc   2139
ctttacacag gcctcggaaa acaatggagt gagcacaaga tgcctgtgc agctgcccga    2199 gggtctccgc ccaccccggc cggactttga tccccccgaa gtcttcacag gcactgcatc   2259
gggttgtctg gcgcccttt cctccagcct aaactgacat catcctatgg actgagccgg    2319
ccactctctg gccgaagtgg cgcaggctgt gcccccgagc tgcccccacc ccctcacagg   2379
gtccctcaga ttataggtgc ccaggctgag gtgaagaggc ctgggggccc tgccttccgg   2439
gcgctcctgg accctgggggc aaacctgtga cccttttcta ctggaataga aatgagtttt   2499
atcatctttg aaaataatt cactcttgaa gtaataaacg tttaaaaaaa tggaaaaaaa   2559
aaaaaaa                                                            2566
```

<210> SEQ ID NO 4
<211> LENGTH: 20
<212> TYPE: DNA
<213> ORGANISM: Artificial Sequence
<220> FEATURE:
<223> OTHER INFORMATION: PCR Primer

<400> SEQUENCE: 4
ctgggctctt cacggtgttc                                               20

<210> SEQ ID NO 5
<211> LENGTH: 19
<212> TYPE: DNA
<213> ORGANISM: Artificial Sequence
<220> FEATURE:
<223> OTHER INFORMATION: PCR Primer

<400> SEQUENCE: 5

```
tcagcccgtt ccacttgtc                                                    19

<210> SEQ ID NO 6
<211> LENGTH: 26
<212> TYPE: DNA
<213> ORGANISM: Artificial Sequence
<220> FEATURE:
<223> OTHER INFORMATION: PCR Probe

<400> SEQUENCE: 6
ccagaacatc agcaggatcc acctcg                                            26

<210> SEQ ID NO 7
<211> LENGTH: 19
<212> TYPE: DNA
<213> ORGANISM: Artificial Sequence
<220> FEATURE:
<223> OTHER INFORMATION: PCR Primer

<400> SEQUENCE: 7
gaaggtgaag gtcggagtc                                                    19

<210> SEQ ID NO 8
<211> LENGTH: 20
<212> TYPE: DNA
<213> ORGANISM: Artificial Sequence
<220> FEATURE:
<223> OTHER INFORMATION: PCR Primer

<400> SEQUENCE: 8
gaagatggtg atgggatttc                                                   20

<210> SEQ ID NO 9
<211> LENGTH: 20
<212> TYPE: DNA
<213> ORGANISM: Artificial Sequence
<220> FEATURE:
<223> OTHER INFORMATION: PCR Probe

<400> SEQUENCE: 9
caagcttccc gttctcagcc                                                   20

<210> SEQ ID NO 10
<211> LENGTH: 972
<212> TYPE: DNA
<213> ORGANISM: Homo sapiens
<220> FEATURE:

<400> SEQUENCE: 10
ggcactgcat cgggttgtct ggcgcccttt tcctccagcc taaactgaca tcatcctatg       60
gactgagccg gccactctct ggccgaagtg gccgcaggct gtgccccga gctgccccca      120 ccccctcaca gggtccctca gattataggt gcccacgctg aggtgaagag gcctgggggc      180
cctgccttcc gggcgctcct ggaccctggg gcaaacctgt gaccttttc tactggaata      240 gaaatgagtt ttatcatctt tgaaaaataa ttcactcttg aagtaataaa cgtttaaaaa      300
aatgggatgc ctgcctctgt gacagccttg tttgctgagg tcgtgggggt ggggcctct       360 gggaagttcc gggctcctct tctcttggtc aatagctcct ttctggtggc tgccaagagc      420
gtctctccca ggccgggctg ctggcttacc ttcctgtgtt ttcaaatttc aaccttgtgc      480
aatgttgagt ttcatagaaa tactgcatga gtacgccctt gtttagaagc agcagggtct      540
gagtcccatc ccacagcccc agtgcagacg cttttgccac ttttgcatgg ggcccctgg       600
```

```
atgtgtttct gtgcatttat ctacaaatcc tggtgcccgt aggacatgcc cgtgtgttct    660
aaggcctttg ctctctgtcc ttacctaaaa ggtgagaaga gagcggctta gaggacagat    720
gggcatctaa aagtctcatc ttagtgtgat cctgcaacga ggattctcga ttggcatcct    780
gctcagttga gctggacatt ccaggattta ggtgcccggg actactggga ggacaggtcg    840
cgcaattcag atttgaacac ttgggaaggt gcctacaagg gtttccccaa ataagatatt    900 tagggatac ccgtcgcaat ttgcaaaagg ggtacgcccc tttgttatgg cgtggactta    960
caaagttttc gt                                                        972
```

```
<210> SEQ ID NO 11
<211> LENGTH: 719
<212> TYPE: DNA
<213> ORGANISM: Homo sapiens
<220> FEATURE:

<400> SEQUENCE: 11
gctcaggccc cgcccctgcc gccggaatcc tgaagcccaa ggtctgcccg ggggcggtcc     60
ggcggcgccg gcgatggggc ataaaaccac tggccacctg ccgggctgct cctgcgtgcg    120
ctgccgtccc ggatccaccg tgcctctgcg gcctgcgtgc ccgagtccc cgcctgtgtc    180 gtctctgtcg ccgtcccgt ctcctgccag gcgcggagcc ctgcgagccg cgggtggggcc    240 ccaggcgcgc agacatgggc tgctccgcca aagcgcgctg ggctgccggg gcgctgggcg    300
tcgcggggct actgtgcgct gtgctgggcg ctgtcatgat cgtgatggtg ccgtcgctca    360
tcaagcagca ggtccttaag aacgtgcgca tcgaccccag tagcctgtcc ttcaacatgt    420
ggaaggagat ccctatcccc ttctatctct ccgtctactt ctttgacgtc atgaacccca    480
gcgagatcct gaagggcgag aagccgcagg tgcgggagcg cgggccctac gtgtacaggg    540
cagttcaggc acaaaagcaa catcaccttc aacaacaacg acaccggtgt ccttcctcga    600
gtaaccgacc ttccagttcc agccctccaa gtcccacggc tcggaagagc gactaccatc    660
gtcatgccca aaatcctggt cttgggtgcg gcggtgatga tggagaataa gcccatgag    719
```

```
<210> SEQ ID NO 12
<211> LENGTH: 485
<212> TYPE: DNA
<213> ORGANISM: Homo sapiens
<220> FEATURE:
<221> NAME/KEY: exon:exon junction
<222> LOCATION: (277)...(278)
<223> OTHER INFORMATION: exon 12:exon 14

<400> SEQUENCE: 12
cccggtcacg ggaatcccca tgaactgctc tgtgaaactg cagctgagcc tctacatgaa     60
atctgtcgca ggcattggac aaactgggaa gattgagcct gtggtcctgc cgctgctctg    120
gtttgcagag agcggggcca tggagggga gactcttcac acattctaca ctcagctggt    180
gttgatgccc aaggtgatgc actatgccca gtacgtcctc ctggcgctgg gctgcgtcct    240
gctgctggtc cctgtcatct gccaaatccg gagccaaggt cctgaggaca ccgtgagcca    300
gccaggcctg gccgctgggc ctgaccggcc cgcgaggccc tacaccccgc ttctcccgga    360
ctctcccagc ggacagcccc ccagcccac aggctgagcc tcccagctgc atgtgcctgt    420
tgcacacctg cacacacgcc ctggcacaca tacacacatg cgtgcaggct tgtgcagaca    480
ctcag                                                                485
```

```
<210> SEQ ID NO 13
```

```
<211> LENGTH: 41322
<212> TYPE: DNA
<213> ORGANISM: Homo sapiens
<220> FEATURE:
<221> NAME/KEY: exon:intron junction
<222> LOCATION: (9980)...(9981)
<223> OTHER INFORMATION: exon 8:intron 8
<221> NAME/KEY: intron
<222> LOCATION: (17618)...(22472)
<223> OTHER INFORMATION: intron 9
<221> NAME/KEY: intron
<222> LOCATION: (22547)...(30283)
<223> OTHER INFORMATION: intron 10
<221> NAME/KEY: intron:exon junction
<222> LOCATION: (30283)...(30284)
<223> OTHER INFORMATION: intron 10:exon 11
<221> NAME/KEY: intron:exon junction
<222> LOCATION: (31237)...(31238)
<223> OTHER INFORMATION: intron 11:exon 12
<221> NAME/KEY: intron
<222> LOCATION: (31385)...(34929)
<223> OTHER INFORMATION: intron 12
<221> NAME/KEY: intron
<222> LOCATION: (35059)...(39154)
<223> OTHER INFORMATION: intron 13
<221> NAME/KEY: intron:exon junction
<222> LOCATION: (39154)...(39155)
<223> OTHER INFORMATION: intron 13:exon 14

<400> SEQUENCE: 13
```

| | | | | | |
|---|---|---|---|---|---|
| cgtcatgaac | cccagcgaga | tcctgaaggg | cgagaagccg | caggtgcggg | agcgcgggcc | 60 |
| ctacgtgtac | aggtgaggct | gtgtccaggt | gagggtggag | gggccggctg | aggctgggca | 120 |
| ggggaggggt | ctcagagtgg | acgggatggg | gaggctgctg | actgagcccc | agagattgtt | 180 |
| ccggaagcag | gcaagtcata | gtcgggtaa | gtgctagtcc | cagagaagtt | tttgttttag | 240 |
| ggttttttt | tttttttttt | tttttttag | agatgggatc | ttgctatgtt | gcccaggctg | 300 |
| gttttgaagt | cctgggctca | agcgatcctc | cgcctcagcc | tctcaaagtg | ctgggattac | 360 |
| aggtgcgaat | caccagacgt | tgcctagaga | ggttctttat | ggagcaggga | gggaccaatg | 420 |
| gtgtgcgtct | gggtggaggg | tgcatgtgtg | agttacacac | atacatacac | acacatacac | 480 |
| atacacatac | acacatacat | acatacacac | gtacatacac | atacacacac | acatacatac | 540 |
| acacacatgt | acctacacat | gcatacacac | atacacacac | acacacacac | acacacacac | 600 |
| atgcatgacc | aggagcaggg | accgaccccc | cagaccctat | ctgggccaga | ggaccgggtg | 660 |
| ggtcagcacg | ggaagggggtc | agctgttttgt | ggaacatgct | ggcccaagga | ccacagagtt | 720 |
| gtgcctttgc | tttctgcttg | tcctgtacct | ggctgtggcc | taggggaagt | gacttcattc | 780 |
| ctctgagcct | cagtttgccc | gtctgcagac | tggagagaca | caagagcccc | ttcatggggt | 840 |
| caccgggaca | ctcaggatgc | actcggagct | ctgagacggc | tggcggatgt | gcctgttaca | 900 |
| actcccttac | ctcctggcgt | tttcacagca | cctccctcc | tccacacccc | cacttcccag | 960 |
| ttcacagaca | ggggagctga | cttgcccccg | gcacacggtg | ttccagggat | ggggcgggca | 1020 |
| gagggtgttc | ccgctgttgg | agacccacag | tctggttctg | ggaaagccaa | gatgaaaacc | 1080 |
| cagcaaatgt | gcctgaggtt | tgggaatggg | aaacatgaat | cagctgctgc | attccgttca | 1140 |
| ctcattcact | cattcgctcg | ttcatttaac | aaatgtttac | tgagcacctg | ctaggtgttg | 1200 |
| gctgccgttc | taagtacagg | ggacccagca | gtggacagaa | tgggcaaaaa | tgccaaagct | 1260 |
| ctctatactc | cttcattctg | tgagcactga | ctgagcacct | cctgtgtgct | ggggcgcag | 1320 |
| gcagaccaag | gccctgcctc | accagctga | tgttctgatg | gggagagagt | aaagaagtgg | 1380 |
| acaaataagg | ggaaatcagg | cagccatcag | tattgtgcag | acaaaacagt | gtgaagccgg | 1440 |

```
agtgcaggag ggagggtggc cttggggctc ggtctgactg agggtcgggg agcacatctg   1500
caaagggaca ctcactggac ccgcatggtg ggaagaggcc ctggggagac agagtcccgg   1560
gcagagcatg tgcaaaggtc tgaaggctgg acagaggcc tgtgcggctg ggttacgag    1620 ggagggagac agtggagaga cgaggcctga gccttgctga gggcctcaga ggtcacgtta   1680
ggagcctgat tttaacctgc atgcaaagtg gggttgtggt ccagagcatg cacgatctg    1740 atttctactt ttttttttga gacggagtct ctctttcacc caggttggag tgcggtggcg   1800
cgatctcggc tcactgcaac gtccgccccc caggttcaag cgattctcct gcctcagcct   1860
cccgagtagc tgggattaca ggcatctgcc accatgccca gctaattttt gtattttttag  1920 tagagacgtg gtttcgccat gttgggcagg atggtcttga actcctgaca tcaggtgatc   1980
tgcccacctc agcctcccaa agtgctgggt ttacaggcat gagccactgc tcccgacctg   2040
atttccactt ttcaaagatt cttctggatg gtggagagtg gcttggagag atgagagatc   2100
ataaggacag cagcagcaac agtcacagca gctgatgttt acctcgtgct ttctctgcac   2160
ccggcggctg tgttgattgc tttctgggta tctgattgct taatccccac agctgccctg   2220
tgaagtaggg cttgtgatta cttccttttg tagatggaga gacgatggcc gtgttgggtg   2280
ggggagagca gaacgaggcc gggtgggcgg cgacaccatg tcctgcagtg gcaggcggc    2340 gggagggaca gacttggcga aggggccgag ctcagctttg gctgtggggc cggaggtgtg   2400
cacagacgtc cagggcccct ggttcccagg caggcattgc aggcgagtag aagggaaacg   2460
tcccatgcag cggggcgggg cgtctgaccc actggcttcc cccacaggga gttcaggcac   2520
aaaagcaaca tcaccttcaa caacaacgac accgtgtcct tcctcgagta ccgcaccttc   2580
cagttccagc cctccaagtc ccacggctcg gagagcgact acatcgtcat gcccaacatc   2640
ctggtcttgg tgaggctgcc ctgtggccca cgccgcctcg caccctgacc tcgtcccctg   2700
tctctcctcc cgcctgcccc ttgtgcagag agcagtccct gaggtggtcg gagcgtgggg   2760
actcacgcct ggtgggtggc tttcggccct gtgctgtctc caccaccccc agtgggttct   2820
gagtttccca ggtgggtcca cctgtcttgg tttggaagtc ctggccaaag tactttttt    2880 tcccttttca atttacattt ctgagatctc caaaagggc tgtcttgttg agggctgagc    2940
cacaggcccg cctctgggac tggggctgga gttcacttag cctgagtcca gtggggtgca   3000 aggggggagaa ggggttctcg ggagcacatg tggccttggc actggaggag cagagggtgg   3060
ttctggtgtc ccagatgccc cacgtggcca ctccagggc ctcctgcacc ccagcatttc    3120
ccttcatggg ctctttgctg tgaggcccag ctggggccaa gggaggatgg gccagccacg   3180
tccagcctct gacactagtg tcccttcgcc ttgcagggtg cggcggtgat gatggagaat   3240
aagcccatga ccctgaagct catcatgacc ttggcattca ccaccctcgg cgaacgtgcc   3300
ttcatgaacc gcactgtggg tgagatcatg tggggctaca aggaccccct tgtgaatctc   3360
atcaacaagt actttccagg catgttcccc ttcaaggaca agttcggatt atttgctgag   3420
gtacgtgtgg cctggtgaga agccaaagat tcaggcctgt gtcctgtctt ccctcacac    3480 agcctggaca ctggtcacca gcttgctttg tagctggctg gggatctagt ggctgtgggt   3540
tgtaagtgac tgagaacctg actcaaaccg gcttgagtga atggggaat gttggggctc    3600 atagaactga aaatgctagg gttggattca ggtacagctt gatccaggct caaatgatgt   3660
gactgggcct tagcttagca aattggaggc tttgctggag aaggggggca tggctgctgg   3720
ggagtaatat cacaagctga ctcttaatct tgactcttgg caacctggta gggtcactga   3780
ctgggcttcg gagccaacat ctcgtccatg gagggtctga ccctgacctt ggctccctca   3840
```

-continued

```
ccgcaggttt cactgagtcc ttgggactgc tccagcctca gccatctctt tggtctctgc    3900
tgatcagggt agagtgctgg gggggatatc gtggtgctgc gtgtgataga tactcagtac    3960 gttttttgtca agggtgacgg gctcctgtcg tgtgggtaaa tgagcaagtt tgggctaagt    4020
ggcatgatgc tgtaaaggca tcttgtaaat cctgaagtgc tttgcaaatg aaagttatta    4080
caaagtccct agtttagtat aatctacgtt tgactgcata taatgaaaac ctcacaagaa    4140
aagtctagcg gtaggctgtt cagtgttggt gtggtggctt catggtctta agtgatctgg    4200
aagccttcta ctactgtgct ctgccatcct tggcatgtgg ttttcatcct caagataacc    4260
tcattgtcca agttggctgc tagagtgtca gcaatcacat cacattccag gcagcacagc    4320
aagaaggaaa aaatggtggg gctttgggga gcagatggag gaactggggg taaaacagcg    4380
tgttccagtt tcctccctct tagggaggaa gaaaaccaat gtccacttcc tttctattgg    4440
ccagaactga gtcacatggc cacacctagc tccaggggaa gctggaaagg tagccttttta    4500 gctgggtgtg ctgatgctct gagtatggtt tgggttttgt atgaaagagt aaggagagat    4560 tgggcttttgg gtagtaactg gcagtttctg atgctctccg tccattataa tgatcattta    4620
agtatcctat tgggtgagca tttattaata ataacaataa taatgaaaat aaagactatc    4680
attttgagct cttactgtgt ccggtgcact gtacctggcc gttttttgcac atgagtccct    4740 ttaatgctcc cctttgtagt ggctctggtt attcttggct ccacatgggc acgtgacaga    4800
cacacccggg atgctgggct gggggccttgt gctgggtcct gctctggagg tctgtgatgg    4860
gtgcagtcac tcagccgggc aaccttggag ctcctcagtg tgctccaccc tgcaaagcac    4920
ttctagatat ttccttcagt cactcatacc actttgtgct ttgcatgtct ttgggattag    4980
aaaccagctt ctgggaaatg ctctcggagc accaaagcct gggccccact atcaagaacc    5040
tcgatgggtt aggacaggcc aggttttgct gctgtgacaa gcagccccgg aatctccatg    5100
gcttagaaca accaagactt attcctttgc ttgcactcca cgtccagtgt gggtgactgg    5160
ggcacccgcg cttgtggtgg tcacttgggg atccaggctg agggaggctc tgtcttgaca    5220
catacctcct tggctgctat agcagcggca gagagcccgg tgaaaggcgt gtgcacagtc    5280
cttaaagcat ccccccaagt gacatgccac ttctcctttt tcattgctca gggagctgac    5340
ctggccatgc tttatttttat gctggagtag ggtgtggtgg gggtgatctg ccatttacct    5400
gggaggaaag ccagactctc ctggagttag aagggaggg tggaacactg cagccacaga    5460
acccgggacc attcctccta gaaagctccc aagcctcctc tcggtcccca gacactgggc    5520
atttggcagt gaaccagatg ctgggggccc tgtccttctg gtgggagggg aggagggctc    5580
agcccagaat gttcagacca ggccggctca atggcaggcc taagccttac gatgctgttc    5640
cctgctgtgt ctgtagctca acaactccga ctctgggctc ttcacggtgt tcacgggggt    5700
ccagaacatc agcaggatcc acctcgtgga caagtgaaac gggctgagca aggtgagggg    5760
cgagaggcga gggcccctgt cgccagggag aggggagggt gggcccggcc atggctgctc    5820
gggagtggca gggaccagag agctccttct tcctttgtcg tgaagagggt gctgggagga    5880
tgaacactct tgaagttgga ggagggattt tacctctggt taaagcttga ccacccagag    5940
gggcaggtgg ggttagtgat tgcttactga gcttactgag cacctggcat ctgctgggaa    6000
ctgagtgctt tcttcctttc gattctttac ttacaaaaat gttttgaagg ccgggcgtgg    6060
tagttcatgc ctgtaatccc agcactttgg gaggccgagg tggggggat cacctgaggt    6120 cagggagttcg agaccagcca ggccaacatg gcaaaaccct gtctctacta aaatacaaaa    6180
```

```
aattagctgg gtgtggtgtt gcatgcctgt aatcccagct actcatgagc tgaggcagga   6240
gaatcgcttg aacacaggag gtgaaggttg cagtgagctg agatcacgca atttcacttc   6300
agcctgggtg agaagagtga aactcggtct ccaaaaaaaa gagaagagat tcacattaca   6360
aaataaaaca agagagggag ataagtgccc ttagtatcac ctcccacccc tacccccttgc   6420 cccagaggaa acccacaatt atcagtttgg gatatattct tcccatccat ttttacccat   6480
gtgcacacct atatgtacgc agagaaatac ggaattgttt cttctttgaa catcatgaaa   6540
tcatactacg tgcattgttt tgcaactggc tttttcacc ttcgtgacct tttctcaata   6600
tgtgtgaaaa tgactgtgtg acttcccact ccccactccc cgtggtagtt actgcaaaga   6660
ccctgagggc tagggacaaa tcgtaccca accggtgccc agagtggcaa aaatcaccat   6720
ctgcaactgg cagtagccat tcacgataga tggagttcac attcattgtg gcttgtatat   6780
tccaatatac tgtacatgtg cacgtgattt taaacatcct catcatacag aagattggaa   6840
agtgagcagt tggttttgtc gagtctgggt ctcgctcccc agagtcagtt aacctgacag   6900
gttctgtttt ggggttgccc ggtggtggcc accattatga ttttaagtag tttgcctgtg   6960
tgccgattgt tttcaggagg tgcctgttga cttccgctct gagggctgag cacagccgcg   7020
ccccacctct cacctcacct gctcaccaca cttcttttcc agattcaggc tggaaatgtg   7080
ggtgataggc ctattttgca gatgaaagaa ctgagtccct agcgaagtta cacattcagg   7140
ggtctgggag ggggaagctg tggtaggcat tctctctgtg tgtctacata gcctgccctc   7200
ttcccaccgt gccagtattg ggaattgagt ggccgtgcgt gcaccagggt gagttaggtg   7260
tgcagcacct gagagggctt attaaggggc cttggcccta ctgagggtc tagtctggat   7320 gcttcccccc aggttgactt ctggcattcc gatcagtgca acatgatcaa tggaacttct   7380
gggcaaatgt ggccgcccctt catgactcct gagtcctcgc tggagttcta cagcccggag   7440
gcctgccggt aatcactggg actcggggcc tcctgggttt cctggtagc tcatggccaa   7500 attctgtggt gttggctgtg cacttggaaa gcattttgac tcatcgtgga tttgactcag   7560
tagcccttgg caccagcttg aattctcttt ggtcacacca ccaaaagcca aactccagct   7620
gccaatgcct ctacacagcc aaagagagg ctgctggtgg tggtttgcag ccaggtggtg   7680
ctgggctggg aggaggggc aggacatgtc aagtcacagg gggccataaa atggaggcga   7740
gaggtgggct ccctctggcg tctggctggt ggccccatg accatctggg tgctgagaca   7800
tcagctggct ctgcttggcc ccttcaggct cagctctgtg tcccatggtc ccagttgtgg   7860
ggtaagagta gacagtgggt ggctcctaca gcccttttct ggaggccttg ctgtgtcgtg   7920
ttccattctg gtcactctgg aaaagtcctt tacttaggaa ttcactcatg tggaccttga   7980
cttatctgcc ctcccagcaa accctgtgaa gccctactgt gtgccaggtg cccggtagtg   8040
agagggtggg ccaagtctcc gttccccagg aggctggaat tcactcatgt ggaccttgac   8100
ttatctgccc tcccagcaaa ccctgtgaag ccctactgtg tgccaggtgc ccggtagtga   8160
gagggtgggc caagtctccg ttccccagga ggctgtgtcc tatcagggca actcaggcaa   8220
atgcacaaac actagagtgt cagagagtga cagtgctttt gctctgtgtg ccacttttt   8280 actatttaa gttttactt atttatttat ttaattttt agagatgggg atctcgctat   8340
gttgcccagg ctagtcttga actcctagcc tcaaggatc ttcctgcttc agcctcccaa   8400
agtgctggga ttgcaggtgt gagctactgt acccagctga ctttaaaagc tgaattttaa   8460
acttaaagaa aagttgcatg agaaatacaa gtggcccccg tctcccccttc acccaggttc   8520 actagccgtg ttaagccccc cacccctct tctcgccgag tgtcttttc cagaaccatc   8580
```

-continued

```
ggagagtagg ttggaggctg tatgccccct tacctccaaa tactcagtgg gtgttttttca    8640
gaaacgagga cattttctta cataaccata atgctgttat caaaatgaga aaatttggca    8700
ttgacataat actgttatct aagctggcac tttcctataa atcaaaatat gcaaggcaca    8760
catgcaattt aaaattttt agtggctgca ttaatacaag taacaagaaa ttggtgaaat     8820
tatttttaat aatgtatttt atttgacctc atatatcaaa aatgggatca tttcaagtgt    8880
tattgatgag gttttttttt tgtttttttt gctagcaagt attagaaatc tggaatgtat    8940
tttatacttg catcccaatt tggactcacc ccatgtcaag ggcgggatgg acagccatgc    9000
gtgctgagtg gctgccgtgg acagagtggg tagcacagtg catgttcaag ttcagaagtg    9060
cttttgagaa agtacaggag catgaatgga tggagggtgg atgggggtggg tgtgggggac   9120
ggtgctgcca cccgaggaag tgacagctga actgagatct gactgaaggg ctgaagtctg    9180
gtggatgaag atgccagagg agactgttct taggcagagg gagcagtgat gcaaagggcc    9240
tggggcagga gtgagtgtgc ttaggaactg cagggaggcc ctgggcacag gaagttgggg    9300
cagggctgag cagagcttat gcaggggcta gataaggtca atgaatccta atggtaggtt    9360
agactagaaa gggtcacaga ttttcagcag gggcatgata tattctgttc ttttttttaat  9420
ttcataactt tcaaaaacaa ttttattttt agagactggg tctcactatg ttccccaggc    9480
tggtctcaca ctcctgggct caagtgatcc tcccacctcg gcctcccaaa gtgctgggat    9540
tacaggtgtg agccataatg cctggcctct gttcttttgt aaaactccat ctggccacgg    9600
ctaatacatt gatgtgggtg gggaggcaga gtcggagcgg agaggcctgt taggaggtcg    9660
ctgcagctcc gcgggtgaga gatgggggcg gtttggaccc gggaggtggt agcgcccgtg    9720
gggagaagtg gctggatctg ggcagccttt ggcagggcct ggctctggcc gccgggtctg    9780
ggtgtcccct ctcatcctgt ctgtcccctg cagatccatg aagctaatgt acaaggagtc    9840
aggggtgttt gaaggcatcc ccacctatcg cttcgtggcc cccaaaaccc tgtttgccaa    9900
cgggtccatc tacccaccca acgaaggctt ctgcccgtgc ctggagtctg gaattcagaa    9960
cgtcagcacc tgcaggttca gtacgtgccg tcccctgtgc tgggatggcg ggagggtgtg    10020
agggtggggc cagctgaggg tttatctgcc cagtgctgtc tgcttaatct ctggcctctg    10080
tactcttgat aatcccatta ggcgaagata atgaggccgc aggaagataa tctgaaaagg    10140
aagaaatgcc aggtctatta gttgctgtca caatatattg ccatgaactt cagggcttag    10200
aacaacacac actggttatc ttgcagttct gtagtcagaa gtctgcgtgg gtctcaccgc    10260
gctcagaaca aggcggctgt gttccttctg gaggctctag gagaagctgc gtctgccttt    10320
tctggcttcc agaggcccct ctgtgtttct tggctcccgg gcccttcctc cacctttgag    10380
gccagcaaca tggcatcctt ctgatccact ctgtcctcat atctcttcct ctcctccctc    10440
ttctgccccc tcttccagtt ctaaggaccc ttaagaccac atcgtgctct cctggatacc    10500
ccaggacaat ctccccatct tgtttattat tatttttttt gagacagact ctcactctgt    10560
tacccaggtt gggtgcagt ggcgccattt cagctcactg caacctccgc ctcccaggtt     10620
caagtgatcc tcccacctca gcctcccgag tagttgggac cacaggcgtg caccaccaca    10680
cctggctaat ttttttgtatt tttggtagag atggggtttt caccatgttg cccaggctgg    10740
tcttgaactc ctgacctcaa gtgatctgcc tgcctcggcc tcccaaagtg ctgggattat    10800
aggtgtgagc caccgcgccc agcctatttt tatattttga gacaaggtat cactctgtag    10860
cctggagctg gagtatagtg gtgcgattat agctcactgc agcctcgacc tcatgggctc    10920
```

```
aagcgatctt cctgcctcag cctcctgagt agctgggacc gcaggtgtgg gccatgatac   10980
ctagctaatt ttattttgt aaagttttta tagagatgtt gtttcaccat gttgcccagg    11040
ctggtctcaa acacctggcc tcaagtgatc cacctgcctc tgcgtgttaa agcaatggga   11100
ttacaggtgt gagccactgt gcccggccca atttctggac cttcaaggca gctgctgagc   11160
aggcccagcg cccgtttacc ctgtgacctg acatagtcat gggttctggg cttagggca    11220
tgtacgtgtc ctaaatgaca tgaaatgagg ctggcgaggg tctgtgtgtt acgtaacatc   11280
ttctcgttcc gcagtgtggg tggctaggca gatgtgatga ctgctgttgg cgtcggtccc   11340
ctgacattgt tggtgtgtct caattgtgtg ccagtccctg agacaccccc acctcaagtt   11400
gctcagtttg gaccctcggg cgtcagtttg tttccctgtc ctcacccagc tcttccagtg   11460
cgtcaacaag cccagatggc tttacctcca ggttgagtcc tcactccttc ctctctcttg   11520
ctccccaccc caaccccgc ctcattgtcc aggccacgga cacgtccttc ctggtgatcc    11580
agccctttca gtagcccatc cctcaatgca gtgttgccgc cttaccatcc atcccctaga   11640
ccatccagtg cggtcactgc tggcctcttg cggctgttta aattgaaatt gatttaaacg   11700
aaatcaaatt aaaggcagt tccttggttg caccggccgg aagttaaatg ctcataagcc    11760
atgtgtgtct agcagctact gtcttggata gcacagatag agaacatttc catcatcata   11820
ggaagttctg tagcactccc gacagcagcg gagggatctt ttaacaatgc aggccgagtg   11880
tggtggttca cgcctgtaat cacaaccctg taggaggccg aggtgggagg atcacttcag   11940
gccaagagtt cgagaccagc ctgggcaata tagcaagacc tctctctggc caaaaaaaaa   12000
aaaaaaaaa aaaattagc taggcatggt ggtgcatgcc tgtagtccta gctacgtgga    12060
aagctgggt ggaaggatgg cctaagccca gaggtcaagg ctgcagtgag ctgtgatcac    12120
cccactgcac tccagcctgg gcaacagagg aagacccatc tcgaaaaata tgcagatggc   12180
cgccgtcctc ttaaaatgtc tggcagctct gtctgcattc atagtgaagt ccaaactccc   12240
accatggccc tgggccctgc aggatccagc ccctaccggc ctctctgaag gatccagccc   12300
caccagcctc tctgactcca tttctcccta cacgtcccct gttcattatt ctccagccct   12360
gatgccttcg ccctttttct aaagtatacc aaggtcagtg ccttgcactg tggtttgcat   12420
gggttgcttc ccctgcttgg agagctcttt gtctggattt ctgagtggat catccctcac   12480
cttcttttgg cctgcatgca aatgccacct cctccgggag gcctcctctg atttcctgtt   12540
ctaaagttgc cccctctccc acctgctgct ccctatggct tcctcttctt gtcttcttgt   12600
cttggtcttc ttgtcttcct cttcttgtct tggtgctcat tgctccctga actcatggac   12660
tgtggatttt attcattgcc ccttccattc actgtcatcc ctgtaggcag gccccaagc    12720
tcctcttgtt ggttttattc ttagcttcta gaactgtgcc ccgcatgtaa tgggtactca   12780
tacagtattt gaatataggg atggtgagtg cgttctgtac ttaggaaatt gaggcctgat   12840
gctggatgcg accaaggtca cagggttggt aggaccggaa gcggccctct atttgactgt   12900
gtcttgcctt ctgggagcct ttttggttga agcccgtcc tccagctggc aatggcgact    12960
ctaaaggact ggtctgcaac aggggtcagg aggagggct gtcaacagat tggatgcttt    13020
cccctatttc aggcagaatg gaacaacctg tgaatgaatg gtttggagct ggggcctggg   13080
acgcccgctg ctgtctcctg gtcctgtctg gcccgtctgg gcattggcct ctgcttgctt   13140
cattctttgc tggtatcggc ggggatttct gctcctaagg ttgaggatgt tacacaccca   13200
ataggtgtgc tacagcaact gtcgcaagtg gcagatgctg gactccacct gatttaggcc   13260
aaaagggcac ttcttggttt gcgtaatgaa aaattccagg gcagatctct gcattaggca   13320
```

```
caaatccaga acttagatgt tgtctggaag ctgcctctgc caagtcccag ctcagttttc    13380
tgctggactg gctttgctgc caagcaggct ctccctcctg gctgcctgtg gaggctccag    13440
gctcacctcc gcccagctcc gagtcctgca gaaaggggc cacctgtgtt tccttcactc     13500
cagcagaagt tccagggttt gctctaattg gtctgcctgg ctcccatgcc cagctgtaaa    13560
ccaatcacag tagccgaggt ggactatgct gattggccag gcttgtgtca catgctcaga    13620
tggctcctgg gtgggccggc cccactccaa gcacaaggct gaaagtaggg aaggcttaaa    13680 gtggggtgt aggtaccagg agaagggga gaaacgacat gcccatcccc tccaagggcg      13740
tgggacgagg tgtgtcccgc cttctcttag cacatctgcc aaaagaattt caaaagcgca    13800
aaggaatttt aaaatcttta tttaaataga gttttttctt atatttattt atattttga     13860 gacagggttt ctctgttgcc caggctcaag tgcagtggtg caatcacagc tcacagcagc    13920
cttgacctcc tgggcacaaa tgattctccc acctcagcct cccaggtagc tgggagcaca    13980
ggtacacacc accatacctg gctaatttat tttatcttat ttcaattttt tttttttttt    14040
tttttttttt tgtagaggtg gggttgtgcc gtcttgcccg ggcttagttt ttgcttctaa    14100
ataaaatata catagataca aagaagttcc cagatgactc atgcagtttt tggggttttt    14160
tgctttgttt tttgagacag ggtatcactg tcgcccaggc tggagtgcag tggtgccatc    14220
atggctcaca gcagtctgac ctccatcact caattgatcc tcttacccca gcctcctgag    14280
tagctgggac tacaagcggt tgctaccatg cccagctaat tcttaaattt tttttaagag    14340
acggggtctc accatattgc ccaggctagt cttgaagtcc tgggctcaag tgatcctccc    14400
gcccaaagtg ctgggattac aggcatgaac cgctgcgcct ggctgacacc tgcagtttga    14460
aacttcacaa agtcaacgca ccccgtggcc agcaccctga ctgagaaaca gacaggacag    14520
gccctggatg ccactcgcgg tcctcccacc gccctgacat ccagcccgg agctcagctg     14580 gtttgcatct tcatgtgaat ggacccataa tgctagactc cttttcctcc ttttctggtc    14640
cgtgcacccc ttagcaccct ggtgcaattc gtccgtgacg ttgtgggtgg tagcagcccc    14700
tcctctccgt tgctgtgtgg tgttccatcg tgggtgccac ctccatcttc tccttccatt    14760
gctcctaggc atccaagttc ctgttttttcg accgtgaccg tggtgcacac gtgtcgtttg    14820
gtgcacctat gtctgtgttt ctgtggcatg ttatctaaag agtaaaggta ccatgccttt    14880
gcctttctgg gccttgaaat ctgttggact cagacaactc cctcatctca aacctccctg    14940
ttgcgtgagg gcatccgact tgcctcacag agccaactaa ttatcatcgg tggcaatcct    15000
gggcaattat gtctggctag atatgccata aagctacaaa ttaattacca cttacagctg    15060
ggaagatctc tctcggcgtg cttggtaata acattggaag aaaacgtgc gtgggtccat     15120 gcaggctcgg cctctgaagc aagggcgggg gctggcaagt tgttccatcc cacctcggtc    15180
tccacctggg gctgtgggca ggccagggct tgtttgagat tcctccagag ttcggctccg    15240
tggctgcctc ctccacggag gaggcacgag aggcagcgtt ttccagattg tggaggacac    15300
tgtccctgcg ggtgcttggg atggcttcag aaggtccaag gaggtgagag tgagcttctg    15360
ggtccatgct cttttcctcc ttgccatcac ctgcaggaga aggtctcttg gtgttgagag    15420
gacttgaaga gccttccaca ctcatcagcc ttttttgttt tgttttttct tttaacagaa    15480
aaagagcagg gctcccagtt aaagcctcat gcagtaacag gttctagtta gaacttacaa    15540
catcattatt ttccacggta tttttttaact atgtcttttt ttttttttttt tgagacacag  15600 tcttgctctg ttgccaaggc tggagtgcaa tggtgcaatc ttggctcacc acaacttctg    15660
```

-continued

```
cctcttgggt tcaagcgatt ctcctgcctc agcctcctga gtagctggga ttacaggtgt   15720
gcaccaccag gcccggctaa ttttgtattt ttagtagaga cggggtttct ccatatcggt   15780
caggctggtc gtgaactccc aacctcaact ggtccacccg cctcggcctc taaagtgct    15840
gggattacag gcgtgagcca ccgcgcccgg ccctttattt tattttattt tttttgagac   15900
acagtcttgc tcttttgccg aggctggagt gcattggtgc aatcttggct tactgcaacc   15960
tccgaaaact attgtccagg ctggagtgca gtgatgcgat ttcagctccc tgcagcctcc   16020
gcaacctctg ccgcccaggt tcaagcaatt ctcctgcctc agcctcccga gtagctggga   16080
ttacaggcac ataccatgct cagctaattt ttgtattttt agtagagacg gggtctcacc   16140
atgttgccca ggctggtctt gaacttctga cctcaagtga tccacccgcc ttggcctccc   16200
aaagagttgg gattacaggc atgagccacc gtgcctggcc tctgattcaa gttttttgttt  16260
tgttttgttt tgttttcctt actgaggcaa aattcttgta acataaaatt aaccatttta   16320
aagtgaatga ttcagtggca tttagcaggg tcacaaggtt gtgcagccat cacttgtatc   16380
tcgttccaga acatttctgt cacccaaaa ggagacccag actcatcaga agtcactccc     16440
cgcccctcc cccagcccct ggtcaccacc cgttggctct gtctgtggat tagcactgtc     16500
tggatccttg tgagcttttt aaaaaaaaat tgttttcct ttgagacagg atcttgctct     16560
gttacccagg ctggagtgca gtggcacggt cacggctcac tgtagcctca acctctgagg   16620
ctcaagcgat tttcctgcct cagcctcctg agtagctgga actacatgca ggtgccacca   16680
tgcccggcta atttttgtag agataggatc ttgccatatt gtccagcctg gtctccaatt   16740
cctgggtgca agtcatctgc ctgctgaggc ctcccaaagt gttgggatta caggtgtaag   16800
ccatggcgcc tggccctcgt gagcttttga gagaggcccg ctcgctgttc cttgttaact   16860
tgtccttcag gcctgttgtc cattgtcccg agggtgagct ggtgtttgcc tggtttggtt    16920
ggtcagtggc gaggttgagc tcacatttgt agcaggtgtg tctacaggga cacactcctg   16980
tggatgcagg gagatctggc cacaggtgca cacacctgag ctccgatcat tgctgcgtgt   17040
cctgcagggg acagtgtggg ctgcttggct tgcgcttgag actcccctcc ccacacccaa   17100
gttcaaatct ggcgttgcct tttccatccg tgcctcccta gcacccttgt gcaccatgca   17160
tttcccctc cccacgcttg cttctgcctt cccttccacc tggaatgcgc ttcccgggca     17220
tccttcacct ggctcctgtg aagaggcctc ttccttcttt tggtctctcc tgtcagaatc   17280
agcggctcct gcctcacccc ttctctggcg cagagcttgt ccctcatcac agggcctggg   17340
gcttttaca gaatggagga agggatcctc tctgtctggt tatcttgtca tcgccacggg   17400
ggtgccctgc agaccacagc tctgtgcaga cctccggcct ggcaggacct gccaatatac   17460
tgtccttgtc tgatgtcccc tccctgcccc tcttctaggt gcccccttgt ttctctccca   17520
tcctcacttc ctcaacgctg acccggttct ggcagaagcg gtgactggcc tgcaccctaa   17580
ccaggaggca cactccttgt tcctggacat ccacccggtg agcccctgcc atcctctgtg   17640
gggggtgggt gattcctggt tggagcacac ctggctgcct cctctctccc caggcagaga   17700
gctgctgtgg gctggggtgg tgggaagcct ggcttctaga atctcgagcc accaaagttc   17760
cttacttcac cccgactcca tagttcaagg tagttcaagg gttttatgat ccctgtactg   17820
gtttctataa atgggctcta agacagtaaa ttaattagaa cttatcagct gggatgtctc   17880
ctacatgtga gctggaggca gccctctgga tgtgtcaaga taccataaag atctttaggt   17940
accaagaaga gcctggggta ttttgcagat aaatcacaca gggaatttgt cccgtgtgaa   18000
gttctgtcta caagcaggga gctggacatg tggccctccc aaggacactc cttcagcttg   18060
```

-continued

```
tggcctcttc tcttggcacc tccgttctct gtaaaatatg cccagttggt cttggtggct    18120
gctaccattg attcagaaat ctgtggtttt ctgtttcctg ggtgggcact tgtggtctat    18180
cccatgggcc tttaacaaaa ttattattat ttttgagaca gggtctcact cggttgccca    18240
ggctggggtg cagtggcatg atcatggctc actgcagctt cgacctccct gggttcaggt    18300
gatcctccca cctcagcctc cctaagtagc caggactaca gacatgtacc accatgcctg    18360
gctaattttt atattttttg tagagacgcg gttttgccat gttgcccagt ctggtctcga    18420
actcttgggc tcaagcgatc ctcctgtctt ggcctcccaa agtaccggga ttacaggcat    18480
gaaccgccgt gcccagccaa aattaattct ctaaattgaa gaagaaaagc tgtctatttt    18540
tgagtgtaca acatgatgtt atgatgtatg tataaactt gtggaatacc taaatcaagc     18600
caattaacat atgcattacc tcacatactg atgatgtatt ggtgctgaga acatttaaaa    18660
tctactgtca gcaactttca agcttacaat acattgctat tcactctagt cactgtgttg    18720
tattgtatag tacaatacag tgactgttgc tctatttccc agtaggtctc ctaaacttac    18780
tccccctgtc taactgaaat tttgtatcct ttgacggact tccccatccc tgcccctggt    18840
agccagtatt ctaccctctg cttccatgaa ttcaactttt tttcttttt ttttctgaga     18900
tggagtttca ctctggttac ccaggctgga gtgcagtggc acgatctcgg ctcactgcaa    18960
cctccgcctc ccgggttcaa gcaattctcc ctgcctcagc ctctcaagta gctgggatta    19020
caggcacaca ccaccacacc cggctaattt ttgtattttt agtagacaca gggttttgcc    19080
acgttggcca tgctggtctc gaactcgtga cctcaggtga tccacccgcc tcggactccc    19140
aggttgctgg gattataggc gtgagccact acgcctggcc tgaattcaac tcttttagat    19200
tccacataca ggtgaggtca tgcagggttt gctttcctgt gcctggccta ttttacttcg    19260
catagtgtcc ccaggtccgt catgttgtca caaataacag gatttccctg tttttattta    19320
tttatttttt gagacagagt cttgctgcgt cacccaggct ggagtgcagt ggcatgatcg    19380
tggctccctg caacctctgc ctcctgggtt caagcaattc tcctgcctcg gcctccagag    19440
tagctgggat taaaggcaca caccaccaca cctggctaat ttttgtattt ttagtggaga    19500
cgggatttca ccatcctgac caagctggtc tggaactcct ggcctcaagt gatccgtcca    19560
cctcggcctc ccaaagtgct gggattccag gcgtgagccg ccgcgcccag ctggatttcc    19620
ctcttttaa acgctgaaca gtatcccact gtgtgtgcac cacgtttctg ctgcccattc     19680
attcactgac ggacacttcg cttgattccg tatcttggcc acagcgtaca tgggagtgcc    19740
cctgtcccctt tgacacactg atttcatttc ctctgggggg atgcccggca gtgggatcac    19800
tgatccgatg gtagttctgg ttttcgttgt ctgaggaagc tccacacgtt tgccacaatg    19860
ctgtgcacct taggcccttc ccgaagctcc atggcggatg ctgttctgca ccattttct     19920
ttgtcctccc aggcctcctt agccgctgac taggccctct cggccccggc cccagccctg    19980
gtctctgcct tccctctttt agttaattcc tcctccagcc tctcttgctc tgctggcttc    20040
cggagaattc caccatgaac acagtctcct gtgcgctctc agtgatcgct ttcctttcag    20100
ggcacggatt ttcttccttc ccctcacatc aagaaagaag gggttaagtt tgggagccca    20160
gagagaggca aacagctgtt ttgccgcagc cactttagct gctgcgtcca attctacctc    20220
cagatgagct tgaggccgac ggggagagga agtggccttt atttctttgt ttttttgagct   20280
gggcacgttg gggagggggga tcaggagatc agcttgctgc ctgttggcct ttagccttga   20340
aaaacgaacg tgtgttggaa gctgcttccg tgtggccact tttctgctcc tgaaactggg    20400
```

```
ggagggcatg gggacggggg actcaacagg acgctgctta tggtggtatc acagctaaga   20460
cttattgtaa tgacagaatt caaagcaaaa ttagcaaagg gaaaaagcac cttgggtgaa   20520
gtcgggggag gccaggctgg agcttccaga gtcctcttcc aggggttcc  tacaggatgc   20580 acttaatgtc tttagcaatg agttgtgaca acatgtagga gatgttgtct agcagggaag   20640
ctcattagaa attcagtgcc catggtgttt tgctagggc  cagtcatgtg ggcacctctg   20700
cctggcaggt accaaaattc taggctctgg aaggaaagc  aggtgctgag caagaaccat   20760 attgttgta  caaataattt cggcccagtg aactactctc atcagttagg ggatggtggg   20820
gaccctcctg aaatctgggt tcccagatgc cagcagaatt cctaaggaga gcagcttcag   20880
gcctgtggcg tgaactctgt tctactcacg ggtgatctca tgcccatccc accaggctct   20940
cgagggcaag cactccccag tcgtgggcgt aagtgaggcc tttaatgagc tcttctttgc   21000
cacaggggcc tggaaggtcc tcagcatgct gggccataat gaagaaaaca tcctttccct   21060
atagtgtacg tgataataac ctaggcattt atggccctgc gtgtggctat cttgcatacc   21120 ttactttgc  tcttgcaaaa attctgtcag gtcgggagag ttctctctgt tttacagatg   21180
aggacgcgac tctcagttaa gaagaaccaa ctgcagttct ctgacctcaa atctagtttt   21240
atttccacta tcatttcctg acttcattct ggaaccacct tcctgttgtt tttgatgaca   21300
catgtgtgtc acttcggtta tttacttaaa aaaaaaagtc tcgttaaaaa gagctgggta   21360
tagtggctca tggctgtaat tccactgctt tgggaggctg aggcaggaag atcacttgag   21420
gctaggagtt tgacgccagc ctgggcaaca tagtgaaact ctgtctctac aaaaataata   21480
atgataaata ggctgggtgt ggtggctcac gcctgtaatc ccactttggg aggccaaggt   21540
gggcagttcg cttgctgcca ggagtttgag accagcctgg tcaacatggt gaaaccctgt   21600
ctttactaaa aatacaaaaa ttagccgagt gtgctggcgc acacctgtag tcccagctac   21660
tggggaggct gaggcaggac aatcgcttga actcaggagg cagaggttgc ctgcactcca   21720
gcctagatga ctgagtaaga ctctgtctca aaaagaaata aaaataaatt tctgcacaaa   21780
ggaagctttt tcttactacc tcaaatagga aattacaaaa ttctccaaaa aaagaagaca   21840
accataaaaa tgaacaagga aaaaaatatt aggctctatg taaaatattg ttgtctgtca   21900
gcaggagtga acctgggcc  agctgtcagc accattgtta gaagtggaga ttttgtgtag   21960
gtgtattaga ggggtattaa agaccatgca aacacctggc tgagacctac tcttcaaaat   22020
gatcaggagg agttgggagt gaattgagaa gggacttttg tctgttttat tgaatgtgga   22080
ggttgagagg gagcatggac aaattgccat tctgcacttt gggaaacgct gtcttaggag   22140
gacaggtgaa agtgattagg tattttccac cctgagacag ccttgcttta tagaaggaac   22200
ctctttgagg ctgtgaacat aactgtgtgg gaagcacttg tttccctata aggggttaga   22260
atcaggagag gagatcccag tgcacctgcc cagcatttct agaactgttg accccccca   22320 gcctgtggct tgttttaggt aagatacaag caagctccac tgggcagtta gctgggacgc   22380
ccaccctctt gactgggacc agggagagga gggttgacgg tgtccctgga gcttggggt   22440 ggccagtctc tcactgtgt  ttgttgccgc aggtcacggg aatccccatg aactgctctg   22500
tgaaactgca gctgagcctc tacatgaaat ctgtcgcagg cattgggtga gtgggactg   22560 ggagctgggc ctgcattgct cattgagaga ttaggtgctc agtgctccag tggtcccaga   22620
ctccagtgac ataccccagg aaccagggca tggggagggg agagggtcct attggggtg   22680 gaatccagtc cctgctgatc ttctccctga ggggtcttgg ttttgagcca ggtcctgacc   22740
tgcatcctga tattccttcc ccagaacacc acttttcttt ctctttttg  ttttgttttg   22800
```

```
ttttgttttt gagatggagt ctcgctcttg ttgcccaggc tggagtgcaa gggcgggata    22860
ttggctcacc acaacctccg cctcccaggt tcaagcgatt ctcctgactc agcctcctga    22920
gtagctggga ttacaggcat gtgccaccac gcccggctaa tttggtattt ttagtagaga    22980
tggggtttca ccatgttggt caggctggtc tcaaactcct ggcctcaagt gatccaccca    23040
cctgggcctc ccagcatgct gggattgcag gcgtgagcca ccgtgcccgg ccttcacttt    23100
tcttttttaa cattcacccc ctccctgcca attagccaga gcttcaatcc aagctgtttc    23160
ctacacgaca gagtggcaga aatgaaagcc tggcaaaacc aaatgtttga aaatggaaac    23220
gctgaggcag gagaatggcg tgaacccggg aggcggagct tgcagtgagc cgagatcgcg    23280
ccactgcact ccagcctggg cgacagagca agactccgtc tcaaaaaaaa aaaaaaaaa    23340
gaatttttca agcactgatt tcctcttttt gattttaaa ataaaacagc tttatgcaaa     23400
tataatgcat gtaccataaa actcacccct ttaaaatgca caattcaaaa taaaaaaaat    23460
aaccccccta ataaaatgca caattcagtg atttgcagta tattcacaga attgtgtatc    23520
tatcaccaca atcaattttg gaacattttc atcatcccca aaagaaaccc cacactcatt    23580
aacactcact tccctgtccc ctcagcccca ggcaaccgtt catccacttc ctgtctctgc    23640
ggacttacct attctgggca tttcatataa atggaatcat acactatgtg gtcttttgcg    23700
actggcttct ttcatttagg atcacgtttt caaggttcat ccatgtcgta gcatggatca    23760
gtatatttta tggctggata atattccatt gtctggatag accacattta tttatcggtt    23820
gatggacgtt tgagttgttt ccacgcctgg gccgttatgc ataatgcagc tgtaaatgtt    23880
cttgtgtcag tcccagtgtg gacatctgtt ctcgttttcc ttaggtatgt accgagggt    23940
ggaatcgctg ggtcctatgt taactctttg tttaaccgtt tgaggaacag tcagacttgc    24000
acagcctctg cccccatcc ccattctttt tttttttt ttttttttga gacggagtct     24060
cgctctgtcg cccaggctgg agtgcagtgg cgcgatctcg gctcactgca agctccgcct    24120
cctgggttca cgccattctc ctgcctcagc ctcccaagta gctgggacta caggcgcccg    24180
ccaccgtgcc cggctaattt tttgtatttt tagtagatac agggtttcac catgttagcc    24240
aggttggtct cgatctcctg acctcgtgat ccgcccgcct cgggctccca aagtgctggg    24300
attacaggcg tgagcaccgc gcccggcccc atccccattc ttagcagcag tgcagcaggg    24360
ttccagttcc tccccacgcg caccagcact tgctataaca ttacacgttg ctagaacttg    24420
gtgagggatt atactgattt gttgctatgt cagtgtctgt acttcttagc atatctgaaa    24480
tagtttcgtt aaaaaaatt ctcttagaaa aatccctggg ttgcaggaat gtgagcatct    24540
attcagcttt gtcaaatgcc tctcggctgg aaagaataac actttgtcag agcacggcag    24600
cgagtaataa ctgtgagctc tcttccttca tcccgcccct gcattttatt tttatatttt    24660
gaggccactt agggaatttg ttcttgatgg atttgtgggt ggggaaacag ccccaggcat    24720
ggaagaggcg tttgcagccc aagtcctccc tctggttcca ccgcgtggca cctgggctgc    24780
taactgggat gcaactgggg ccaagtgggt gaccagatag aagaggcgac ctggggccga    24840
ggatacagcc ccttcccagc accagctgac tgtagcccca tggaaatgcg ggctcagtgt    24900
ggccacatcc tctgcatttt tcaaaaggac ttccaaatct gaattttaac aggagctctg    24960
tcaatttta cttattggga ggtaattcac attcttttt ttttttttt ttttttttg       25020
agacgaagtc ttgccgtgtc acccaggcca gagtgcagtg gcatgatctc agctcactgc    25080
aacctctgcc tcccgggttc cagcgattct cctgcctcag cctctcaagt agctgggatt    25140
```

```
acaggcgctc gctagtacac ccagctaatt tttgtatttt tagtggagac aggatttcac   25200
catgttggcc aggctgttct cgaacttgtg acctcaggtg atccgcctcc cagagtgctg   25260
ggattatagg catgagccct gcgctgggcc taattcacat tcttaacaaa cagttcacgc   25320
gggcagctgg attgtgcctg ccagtgacct gtggaccggt cacccaacct ctctgggccg   25380
cacagctgct gacctccctg tggactggga caaggcact ccaggaaagt ggtctcaaca    25440
gcagatgtgg agggccacga gggatggccg tgggaaaagt ctagagacac agctgccggg   25500
aagcagagct gtctcgtgac ctgtcgggga agcttctgtg ctccttgctc gctaggtaaa   25560
ggcagtgggg ttgcatgtta cttgaataca attcccattg gttcttacaa agtctttcag   25620
agaaaagcag ccaaagtaaa tggtaccgtc tgttgtctcc ccatcgtgtt tcgtcctctg   25680
tagggtgata gtgtgagccc atttcactgt gcaatacct acttaacaag gggcctgaga    25740
gacctccaat aattgtgatt gggggatttc agcctttttt tttttttaag atggatcttg   25800
ctcttgtcgc ccaggctgga gtacaatggc gcgatttcgg ctcactgcaa cctccgcctc   25860
gggttcaagc gattctcctg cctcagcctc ccgcgtagct gggattacag gtcccgcca    25920 ccacgcccag caaattttg tatttttagt agagacgggg tttcactgtg ttggccaggc     25980
tggtctcaaa ctcctgacct caggtgatca cctgcctcag cctcccaaag tgctgggatt   26040
acaggcgtga gccactgcgc ccggtctctg attgtggtat ttgagccttt tgtgctgact   26100
ttcgtcaccg cccctcagtg acttccatct cccctcccta ctgctgtgca tggcaaagtg   26160
acagaatatt tgtgtgtcca tttctttgct gggatttaac aattataaca acaacaataa   26220
taaatgtgcc aagcactttt atatgccggg taattttcga agcactttac atgtattact   26280
gcattgaatc ctccctagag tcctaggaag agttacgtta taatatctcg cttatacaga   26340
agggacacag gctcagtagc acgcccaagg tcacagagct cgtaagtggc tgtgtcaggg   26400
gtcccaaggc caccgcaggc tcgacgattt gctgggaagc ctcaggacga agcatatggt   26460
tgtacacgtg gctatgattt attacggtaa aaggattcaa agcaaatcag caaagggaaa   26520
agccacacgg ggccaagtcc agaggaaagc aggtgccagt ttccagagcc ctctcccagg   26580
ggagtcaccc aattcttgct gcaaggagtt gtgacaaccc acgtgacatg tcatctggca   26640
gggaagcccg ctagagagac tgagtgccca gggtttttac tagggctgg tcatgtggcc    26700 accctctgcc tggcaggtac tgaaattcca gaccctaga aggcaagctg gtggtcagta    26760
taaaccacat tacttgtaca gattgctcag gcacagtgag ccatccttgt cagttaggga   26820
gcaatgggag gcctcccgaa tccaggctcc cagacgccag ctccgggcca gcattgccag   26880
cagcctgtgt gggggtggaag ggctcgggcc tgccacgtga gcacgtgcct gcacagcggc   26940
ccaggtggga ttcaaatcca ggcagcgacg cttgagtgtg cactattaac cacctcgcca   27000
cactgccttt tctgctagac acctgttgtg gggggtctg tgtggggcaa gtggtgagcc    27060
agcccaccct gctgctccat actgagtgtg agttgctgta ttcatttcct tttgctgctg   27120
tcacaatttt gccacaaatg tcatggctca cttttaaaaa ctatcttgca gtgttgggag   27180
tctgaagtct gaaaggaaca caacaaggct aagatcaagg tatctgcagg ccttgttcct   27240
tccagaggct ccagggagaa acctgtgcct tgccgtttac agcttctaga agctgcctac   27300
tttccttagc tcatgacctt aatcctagcc ctccctgttt tgttgttgtt gttgttgttg   27360
ttgagacaca gtctcgctct gctatctaga ctggagtaca gtggcatgat ctatagttca   27420
ctgcagcctt ggcctcctgg gcttaggcga tcctcccacc tgagcctcct gagtagctgg   27480
gactacaggc atgtgccacc ataccctgct aattttgtg ttttttttgt agagacaggg    27540
```

```
gtctcactat gttgcccagg ctggtcttga actccagggt gcaagtgatc ctcccacctc   27600
agcctcccaa agtgctggga ttacaggcgt gaaccactgc acttggcctc tccctcttta   27660
aagccagcag tgtagcactg tccaatttct ctctgcctct aacctcctgc ttccctcttt   27720 ttttttttttt tgagacggag tctcactctg tcgccaggct ggagtgcaat ggcatgatct   27780
ccgctcactg caacctctga ctccctggtt caagtgattc tcctgcctca gcctcccgag   27840
tagctgggat tacaggcatg tgccaccacg tccggccaat ttttatattt ttagtagaga   27900
tggggtttca ccatgttgcc caggatggtc tcaatctcct gaccttgtga tccacctgcc   27960
tcggcctccc aaagtgctgg gattacaggc gtgagccacc acgcccagc ccctcttttt   28020 aaaaattaat ttttcttttt ttagggtttt aaaatttgtt tttgttttttt cgttttttctt   28080 tctcttgcct gattgctctg ctaggactt cccgcttctc tctttaagga cttttgtgat   28140
tctctggggc ctacctaggt attccaggat actcttccca tctcagaacc ttgatgtaac   28200
catatctgca tggacccacc tagatattcc aggacgctct ccccatctga gagccttgat   28260
gcagtcatgt ctgcacggtc cccttcgtcg tggcaggtca cagtttccca ggtgtcgcat   28320
tggtcttccg gtctccttag gcaccttttg gctgtgacag tctctcatct ctccttcatt   28380
ttgatgacag tgcacttttt gagaagcact ggtcaggtat tttgtaggat gaccctctac   28440
tgggattggt ctggtgcttt tctcatgatt agactggggt gatggttttt gggaggagga   28500
ccgcagagag aaagttccag tttcagagca tcttgggtac attccgtcaa catactgtat   28560
cactgttgat gtcgaccttg atagcctgga tgaggtcatg cctgtgacgt ttctgcagta   28620
tcaagtttac ttttattctc cctttggatt ttattatctt tttaacttga cgtgtaagtt   28680
ttaacttcac aggtaataag aacatatctt cctgagggga agaatatggt ttcctgtgac   28740
tccccgccat ccccagccgt acccaccatc atcaatttgc tgtgcttcct tccaggcctt   28800
ttcctactta tttacattca tatatatgtg gccatagaga agatacatat tgtcgtttgt   28860
ctgtttgtct ttgctagtcc aagcaacact gaacatcttt gtgcctctgt gtgcatgtgt   28920
gagcatctct agggcagttt ctgaagagcg taattgctgg gtcgtgaggt atattggtgg   28980
aattaggttt ggcagtatag atcagtaaac tcaacagttg tggctcaaat gggacaaagg   29040
tatattgtta ttttaaaaat cttctttag aggatgtctg gaggcagaca gtccaagtat   29100
ggcaagagac attcatagtc caagttccac tcatctttct gttccatttt cccaacacat   29160
ggcttccatc ctcaaggtca cctctggtcc cagtgtctgc agagctccag cccttgcatc   29220
tgcgtttcag gcatctgaaa gggaggaggg aaaaaaggtt cacctcccag ctgtgaaagc   29280 ttcttttttaa gcagccctcc cggccatccc acgtaacgct tctgcgaaca tctcattaac   29340
cagaacttgg tcacagagcc tcacttgcca caagagaggc tgaagtggag tctttaactg   29400
ggtgcattgc catcctgagt aaaaatttggg tcctgttcct aaaagggacc aatggatttt   29460
ggctgggtca ctggtggtct ctgccctgta ggagatgtga gtttttagtt taaaaagatt   29520 atttcaagt tgtcaagctc tttgccaggg gagattcctt ctggcagcac atcgaaacac   29580
tggttccctc agcccatgcc aatcaagtac catggacccc ttatccctgg gggtatattc   29640
caagaccccc agtggatgcc tgaagctggg gatagtactg aaccctgtat agcatatact   29700
atgcttcttc ctatacacac acatctatga taaagttaat ttataaatta ggcatagcca   29760
caattaacaa taactaagaa tagggtaatt ataacaaata ctataataaa agttatgtga   29820
acatggtctc tccctcaaaa tatcttattg tactgtactg agggtaagaa atggcagaaa   29880
```

-continued

```
tcaaaaccat ggataaggag ggatgactga gattgcagaa tcaaatccct cctggcctca    29940
gagcttatga tcacaggttc aaagctgtgt gatgtcaaac agccctgtgg gaaaacatct    30000
caccttgtca actaaagaaa aaaaaaaaca aaacgccttt taaagattta agttagtct     30060 tatttacaag tattattgag ggctgtagac tgagaccttc agcctgggga cagttttgtc    30120
atatggctcc taaagtgttt cagctcattg tttatatttg gtggtgaggg tttagtgtgt    30180
gcaaaattat actaaacctg tttagatgtt gtattcaagc agaattagat caagtttggg    30240
tgtaagactt tgtttcacac agctatgtct tgcttatttc cagacaaact gggaagattg    30300
agcctgtggt cctgccgctg ctctggtttg cagaggtaag ggtgcgttgg gcacagcgtc    30360
gggggctttt gttaagagcc aatgtgggca tttgaggcag gaggcggggg gagcagcttg    30420
tagaaaggga gagggctgag ccagggtaac cggactgtga catggaccag cgtatcagaa    30480 acttcacccct gtccaagcac cctatgtcag ttatcccacc aaggtgaaag ggatccctag    30540
agatggggaa gacagaagct gcatgaagag gtaaagtccc tggccctggg tgtaaaataa    30600
ttttgttggg gcatatgacc tcttctcctg aaagtgggga agttggtttc caaggtgtca    30660
gcttttctct taaacttact tctctcgcag cttttcagaa ttccttctgg cctagcttgt    30720
tttattttat tatttttattt tattttattt actgtattta ttgtttcttg cccacctcgt    30780
tttaaatcag ggctagctaa tggccaggac aaacaagcct ccgaatgtca agtttacttc    30840
ctactcacag ccgaatctga agtgggttga tggggaggca gagctctgct ccctgcagtc    30900 atttaggggtt ccagggcccc ggtggccccg ccatcctgga gagcctccat tcagtggcag    30960
ggaacgagat ggagagtcac gtgaggccag gtccacctcc cattggtcag gacacgatca    31020
tatggccctg cccaactgca agggagtcgg ggaattgtag tctcaccttg tgtcctggag    31080
ggaggaggtc cctggcaggc tccaacacat gctttagccg ggaagcttga ggtggggaaa    31140
agctgaggcg ggcacagagg aaggtgttgg gtggcatctg cgctgtagcc cgcagcctgc    31200
ggccccagct catgtgtttg tcattctgtc tcctcagagc ggggccatgg aggggggagac    31260 tcttcacaca ttctacactc agctggtgtt gatgcccaag gtgatgcact atgcccagta    31320
cgtcctcctg gcgctgggct gcgtcctgct gctggtccct gtcatctgcc aaatccggag    31380
ccaagtaggt gctggccaga gggcagcccg ggctgacagc cattcgcttg cctgctgggg    31440
gaaaggggcc tcagatcgga ccctctggcc aaccgcagcc tggagcccac ctccagcagc    31500
agtcctgcgt ctctgccgga gtgggagcgg tcactgctgg gggctgcgca gcacgcttgc    31560
gtcttttgca tgccgcgttg ccactactct gcctgttctg gaaggcctgg gaccctccct    31620
tggagggggc acaggtgggc tttgagtaat gagacctggt acttgcatca tccattcatc    31680
aagtcagcac ccggggatgc caggttctgt taggggcgag gggacgtaca gcagtagagg    31740
agacagctga gatccctgct caggggggatt gaggggggct ggcatcccag ccggggagac    31800
agatgaaaac caagtaaatc agcagaaaag ataatttcac tcatgatagg agctgtgagg    31860
ggttagagcc aaatagaaat acagcgtgag ccacgtgtga ggttttcagt ttaaattttc    31920
taatagccac ttaacagtca aaggaaacag gtggaattaa ttttaatctt atttaacccca   31980 aatatatgca aagtattatc acttcaacat gtaatcagta taaacggcat caatatttt    32040 gcagtgtttt tgcatgaagt ctttgaaatc ctgtgtgtac gatacatgtg cagcaggtct    32100
cattttggac tggccccgtt tcaagggctc accaactgaa tgcagcttcc agactggaga    32160
gtgcatgtct ggagcaagtg gggacaagga cagatggagc ttcaggaagg cctctctgaa    32220
gaggtagata gtgagctttg acatggaggc cagggaggca ctcagcacac agccacatga    32280
```

```
ggaatgctgc ctggagcggc cactgcaaag gccctgtggc agggacaggc aaggcacatt    32340
ggacggtcag gtagggccag ggtggctgga ggggagtgag ggcagggaca gaggtaggag    32400
gtggtgtctg agagtggaca gggcgggcca cccagggcct cgtggtgcac agtgagcagt    32460
ttggaactga ttctgggagt gacagaggca ttggaggctt ttaaagaggg gaatcactag    32520
gtcagctgct ggctggggaa tgggccccgg gctgggaggg gtggaagcct gggcccagcg    32580
gggaggcccc agtgcgtgag gaagtcgatg gcttgaacag gatgggcag ctgctatcag     32640
gagggaacgg aagtggggaa gagctccagc cctgggcttc agacctccag aagcagcagg    32700
aagagggtg ataacagtgt ccctccttgc ttcgggtca tttatttatt cattcatgca      32760
ttcactgcaa ggccctttgc acaggtcagg ggatgcagat gaccagaaca taagatctgc    32820
agcaaagatg ggcaaggcag gcctttaggc aagttactac agtcacacga aggacaggag    32880
agctgtgatc acagagctca aggggcagtg gagatgggcg agtggctgcc atggcagggg    32940
aagggatgct gcccactggc aggtcatcag gaaaggctgt ttttggatgc atggaccaga    33000
aagccactct ctgaggtggc ccccacctgc atcatcctag gccacaggc cgaggccttc     33060
tgagggcct tgggctgcc ccgctgctct gctggtcttg gctcctctgc agcacctgct      33120
tcctttagca ctggtgaatg attcttcctc ttccctgtc tcaggaagg cttgcctgct     33180
tccatgcttg catgctgggt gacaataaag cattcctggt tcttcacctt ggctttcaga    33240
cctgaaaccc gacttccttt caaaattcct gtcctcgggg ggaaaaggtt tccacaatgt    33300
gagatggtag cctggacacc agctgtcatc atgttgctgc tctagcgttt gagctcccga    33360
tgaacaatga ccattgggtc caaccagccc ttttgggagc cccttctct gttactgccc     33420
caggggagc cagaacccag cagggctgtg actccagcga gcaaaatgga actccctcca    33480
gtttctagac tgaattatgt agggaggaca gaaggactca gaacccacac tcccagacca    33540
tgaataccctt cccgtggcag agcatcacca taggtgtcca caagtgacga cgcacagcca   33600
catgagggggg tccctgggga ctggctgagg gactgggcca gaggaggcca tgacagcctc   33660
atccctctgt ctccttctgt ctgtctccaa attgtccacc agaatgggga cagggaagga    33720
gggtcaggaa gcacagaagg tctaggctgt ggctagggtc cctttccctg ccgcagcccc    33780
caaatcagca tcccaccctc aaatccagta agaatgctac gatcggcagt gtggctccct    33840
ccctgcaggt ttcactggag gccacgtaag tgaaatttat cccattatgt gtgttttgat    33900
gtagcaggac cttaccagtt ttttttgttt tttattttt attttttttg gtttctttt      33960
tgagatggag tcttgctgtg ttgcccaggc tggagtgcag tggcacaatc ttggctcact    34020
gcaacctcca cctcccgggt tcaagtggga gcctcagcct cagcctcagc tcagcctcc     34080
cgagcagttg ggattacagg cacctgccac catgcctggc taattttgt atattgagta     34140
gaggcgggggt ttcaccatgt tggccaggct ggtcttgaac tcctgacctc atgatctgcc    34200
gccttggcct cccaaagttc tgggattaca ggtgtgagcc actgtgcctg ccggccttta    34260
tcagttttta tgtaatttgt cctgatttaa aaaaaaaaa tcacatgcgg gtaaactcaa     34320
catatttttaa tttctcttta gagaaatttt ccacttgagc caggtatggt ggctcttgcc   34380
tgtaatctga gctactcggg aggttgaggt gggaggatca cttgagccca ggagttggag    34440
gctgcagtga gccatgatcg caccattgca ctccagcctg acaacagag tgagatcctg     34500
tctcaaaaat taaaaaaagc agtaattttt tcttctcaag tcattctttt aaaataaatc    34560
aaaagtattt taacagaaca atctgttcct cgttgatttt aaacagcccc ccagctaagt    34620
```

```
ccactggttg tcggtctcca tggcccatct ccccaccttg cttcctcgct ggcttaaatt   34680
ttcaagtgga cgagcccttt tcagcttggc ttgtccacct cccaggtgtg tttcctgaag   34740
atgcttgtac ttatgtctaa gagcggcagc tccccacatc tcagccacct gcaatcgttg   34800
agggttgttg gactctaaac ttatgtgcct ttcctgtttc ctctttgcct tttgcaaatt   34860
gaagaaccgt gtaaaaccat ttttatgtgg cttcaacgtc aactataaat tagcttggtt   34920
atcttctagg agaaatgcta tttattttgg agtagtagta aaaagggctc aaaggataag   34980
gaggccattc aggcctattc tgaatccctg atgacatcag ctcccaaggg ctctgtgctg   35040
caggaagcaa aactgtaggt gggtaccagg taatgccgtg cgcctcccg cccctccca    35100 tatcaagtag aatgctggcg gcttaaaaca tttgggtcc tgctcattcc ttcagcctca   35160
acttcacctg gagtgtctac agactgaaga tgcatatttg tgtattttgc ttttggagaa   35220
actgcccttc ctatgttctg agtgaatagc agttttttg atcccagagg gcaacttgta   35280
ttctgtgggc tggtgcctat ttgcaaggtc acattagaaa gacaggagca aggcttaggc   35340
ctgctgcttc tggaatctct tgtgcaatag actcccctgg ggaagtctgc tagaaatgca   35400
gatccctggg cagccttcta gccttctgga ataggatcat ggtgggaccc tggaatctgt   35460
attttaatgg accctaatga gattctgatg tagaaacatg tttgagaggc attgatctaa   35520
atctgggatg actggccagg tgcggtggct cacacctgta atcccagcact tgggaggcc   35580 gaagcaggtg gatcatttga ggtcaggagt tcaagaccag cctggccaac atggtgaaaa   35640
cctgtctcta ctaaaaatac aaaaaaaatt agctgggtgt ggtggcacac gcttgtaatc   35700
ccagctactc aggaggctga ggcaggagaa tcgcttgaac ccgggagatg gaggttgcag   35760
tgagccaaga tcgtgccact gcactccagc ctgggtgaca gagtgagact ccgtctcaaa   35820
aaaataaaac taaataaat aaataaataa atacatctgg gatgactgac caagaacaaa   35880
gaatgtaggc atcaactgaa caccaactgt atacctggga ctggatctga gggtaggatt   35940
gccagattga gcacaaacaa acaaacgaaa cacaagaaac aacagaaggg tgcctgttaa   36000
atatgaattt ctggtaagca ataagtaatt tttattgtgt tcctgtgcaa tgataggacg   36060
cacgtatcct gaaaacctgt ctgtagttca cctgaaattc acatttaact aggcgttctg   36120 atttatgtg gccgccctat ctgctgggaa cataggctga tgcccctggg ggttctgcgt   36180
ttccttggcc aggttcctgt agggctgagg tcatggggga gccgtggcca gggatggtgt   36240
ccttgccagg ggaggtgacg ggcagagctg caggccctac aacttggggt tgggcaggga   36300
tgagtcgctc taccgtggtg cctctgataa tagctgttat tttagtttct gaaaaatgtg   36360
ctgccctcaa gagcttctga ggctaggcct acttgggtga aaatagcttt ccagggagcc   36420
acattgtggg gacgtgaggc agcagcccca ctctttgggg ccacttggct gtctctaact   36480
catctcactt gccagggctg gacaaggaga tgaaaagaa aatgccaagg ggtgggcagg   36540
caggagcctg ttggcgttgg caggcgctgc cagccctgtg tcccagtcaa gctctggggc   36600
gcccttcctg tccatctggg agtaggggt ggagtctgac catgttgggg tggagtgtta   36660
atattaggag aggatcctcc ctgggacagg gtccccaggc ttgggggcaa ggccttctgc   36720
ctggaccccc ttccttttcct ctctcccagg attcctccag gacaccgtag tgctgtgcac   36780
ggtttggccc catcggtgtg cctgctcctt ccagccactg ctccccttctg cagaaacttg   36840 cctgggattc ccagggtgca ggggtggggg ctggtcaggg gctggtcagg gcctggtcag   36900
tgtagagcag ggagcttttc acttttagca tagatagagt ggccagggcc ccatggctgc   36960
acctccctgg acataaccag gatgtcctgt catctgcccc ccaaacaaaa ctggggtctc   37020
```

```
ccctttattt tgccaacaga atccaatttt taggtgatga dacaagtgtt tgacttgaaa    37080
agaccctcct gccctgcctc ctggaaggtc tggagcccag cccagcgccc cggatcccct    37140
aggcatgtga aacggggaat gcagtgtcct ccagtggctg gctgcagctt ggggtgggca    37200
cctgggtggt ggctggtggt cccctgcag gccactgctg cccctcttg ggtcctgttc      37260 tgagtctcag gcctgagtcc ctggggaagg ccccacacct ttgccctgta cctgggtatg    37320
gggatggccc tgaggggctg ccttgcttgg gagaaggggg gaaaacagat atttttatat    37380
aaataagaaa aagacagccc ctctgggcag atgaggcctg ctgtagggca gggggcttgg    37440
taaactgtgt gtccactggt ctgtaaccct tcagctgggt cctttgtgc agtgaacagc     37500 ctggacaact gtccaggtgg cccttcaggg atatgttcct ggacctttct tagcttctca    37560
ccgatctttc ttccacgcca agtccatgtt cctcagtcaa acaagtggca aagaggagga    37620
ggaggagggg aaggaggagg aacctgcttc accctctggc acctgcgggt tttgttccac    37680
gtgtcttcct tgggaaagac aagggggttct tttacagcct agggggtggtt tcccctttct  37740 acttctgagt gagaccttct caagtcacgg ctctttgggc ccacatggct aaggtctagc    37800
cacctgtggg tgtcctgtgc tgcctcagtg ggtggtgtgg gggcggggct gacctccccc    37860
gcgcctggct cagtgcagca gaccctggcc cctgtgcccg ctctctgccc tgagcaggag    37920
tttgattttc ctaccccgtg gtgaagcaag cacaggtggg cggaggtggg cagcggtttc    37980
cagccccagc caccgcggca gggaggcctc tgttgctcag ggcaagggag gcagggggct    38040
tagtgggacg aaggctcacc ccacactctt atcattagca ttatctgtat ttttaattt    38100 taagttgaga aattttctac aactgtcaaa ctagacaaat gacagtatcc agttcccctc    38160
acccagacgc agccattgct gacagctgtc agtgttgaag atggccagca tctcatgccc    38220
ttggtttcac tcgttccctg ggtggccctc gtccccctcc ccacgtcctg cgccccgcat    38280
accctgagca gccatggcca ggaacttggc acgtgggttt gttttttctg aatctgcatg    38340
tgcgcagcca tgagcatgag gtcactttt gaatgtgacc gaagctgcat cctgctgcgt    38400
gtattgctgt gtggctggct ttcctccctg tcttctgttc aggaatactg ttcaggctga    38460
ataccgtcct gtgacatggg tttaaaaaca caggccaggc atggtgtctc acgcctggaa    38520
tcccagcgct ttgggaggct gaggtgagag gatcgcctga gcccaggagt tcgagaccag    38580
cctgggcaac atagacctga tctctacaaa aaattaaaaa atgagccggg cgtggtggtg    38640
gcacgtgtca ttgtcccggc cacttgggag gccgaggtgg gaggatcact tgagcccagg    38700
agttcaaggc cgtggtgagc catgatggca ccaccgtact ccagcctggg cgacagagag    38760
agaccgtctc taaaaaataa aaaataaatc aacacataaa catacgttct cctcctgagg    38820
gacagagctt gccccggttg ttccatgttg actgtgctgc acacaggccg ccccccttgc    38880
tctgcccctc actgtattaa gtctctttgg gcctcagttt ctccatctct aaaggaggtc    38940
ggggaggcca ggcgggtgtt gagtgagatg aagaggccct tggagtcatt ccaggagtct    39000
ataggtgact ccagtctctt ctcacttctg acagcctggt ggcggggggtg gagtctctgc    39060 tggggatgtg ggtacagggc tgtggtgggc ggggatgagg gtggggtttg gtgacagggc    39120
gtgggtggtc acccagcttt gccttctcc acagggtcct gaggacaccg tgagccagcc    39180
aggcctggcc gctgggcctg accggccccc cagcccctac accccgcttc tcccggactc    39240
tcccagcgga cagcccccca gccccacagc ctgagcctcc cagctgccat gtgcctgttg    39300
cacacctgca cacgcgccct ggcacacata cacacatgcg tgcaggcttg tgcagacact    39360
```

-continued

```
cagggatgga gctgctgctg aagggacttg tagggagagg ctcgtcaaca agcactgttc    39420
tggaaccttc tctccacgtg gcccacaggc ctgaccacag gggctgtggg tcctgcgtcc    39480
ccttcctcgg gtgagcctgg cctgtcccgt tcagccgttg ggcccaggct tcctcccctc    39540
caaggtgaaa cactgcagtc ccggtgtggt ggctccccat gcaggacggg ccaggctggg    39600
agtgccgcct tcctgtgcca aattcagtgg ggactcagtg cccaggccct ggccacgagc    39660
tttggccttg gtctacctgc caggccaggc aaagcgcctt tacacaggcc tcggaaaaca    39720
atggagtgag cacaagatgc cctgtgcagc tgcccgaggg tctccgccca ccccggccgg    39780
actttgatcc ccccgaagtc ttcacaggca ctgcatcggg ttgtctggcg cccttttcct    39840
ccagcctaaa ctgacatcat cctatggact gagccggcca ctctctggcc gaagtggccg    39900
caggctgtgc ccccgagctg ccccacccc ctcacaggt ccctcagatt ataggtgccc    39960
aggctgaggt gaagaggcct gggggccctg ccttccgggc gctcctggac cctggggcaa    40020
acctgtgacc cttttctact ggaatagaaa tgagttttat catctttgaa aaataattca    40080
ctcttgaagt aataaacgtt taaaaaatg ggatgcctgc ctctgtgaca gccttgtttg    40140
ctgaggtcgt gggggtgggg gcctctggga agttccgggc tcctcttctc ttggtcaata    40200
gctcctttct ggtggctgcc aagagcgtct ctcccagggc cgggctgctg gcttaccttc    40260
ctgttgtttt caaatttcaa ccttgtgcaa tgttgagttt catagaaata ctgcatgagt    40320
acgcccttgt ttagaagcag cagggtctga gtcccatccc acagccccca gtgcagacgc    40380
ttttgccact tttgcatggg gcccctggga tgtgtttctg tgcatttatc tacaaatcct    40440
ggtgcccata ggacatgccc cgtgttgttc taggcctttg ctttctgctc gttacataaa    40500
tggtgaagaa gagaagcggg taagagaaca gattggagcc atctaaaagt tctcatctta    40560
agtgtagatc attgcaaagg atggaatttt ctccgattgt catcatcgtt gatgtttgaa    40620
tatgagacca tttcatcagt atttaagtgt gcccgctggg atctaactag gagaggagag    40680
ggtattcact gccgaacatt tcaaagaata tacgaacaag ctcttttatg gtcagaaatg    40740
ttagcccttt tccccttaaa cttgtatttc ctttcttctt ccctcctaaa attttatcta    40800
aatgatattt atatttgatg cttttaagcc ttttattaat cactcctata cttgcctgca    40860
acataaatat ataagttgaa gcaaactttt ttttttatt tcttgtgacc atcaagggta    40920
aattttttta ggtctggggc tgccataaca aaataccatc aaggccgggc gtggtggcac    40980
acgcctgtaa tcccagccct gtgggaggcc aagaccggag gattgcttga tgccaggagt    41040
tcaagactag tctgggtaat atggtgagac cctcatcaat acaaaaaaa tacaaaaatt    41100 agccaggcgt ggtggtgggc gcctgtggtc ccaactactc aggaggctga ggtaggattg    41160
ctggaagcca agaggttgag gctgcagtga gctgtgatca tgccactgca ctccagcctg    41220
cgagacagag tgagacactg tctcaaaaag aaaaaatacc atcaataggt ggcttaaacc    41280
atttatttct cacagctctg gaggctggaa gtctgagacc ag                      41322
```

<210> SEQ ID NO 14
<211> LENGTH: 20
<212> TYPE: DNA
<213> ORGANISM: Artificial Sequence
<220> FEATURE:
<223> OTHER INFORMATION: Antisense Oligonucleotide

<400> SEQUENCE: 14
cagggctccg cgcctggcag                                               20

```
<210> SEQ ID NO 15
<211> LENGTH: 20
<212> TYPE: DNA
<213> ORGANISM: Artificial Sequence
<220> FEATURE:
<223> OTHER INFORMATION: Antisense Oligonucleotide

<400> SEQUENCE: 15
ggagcagccc atgtctgcgc                                               20

<210> SEQ ID NO 16
<211> LENGTH: 20
<212> TYPE: DNA
<213> ORGANISM: Artificial Sequence
<220> FEATURE:
<223> OTHER INFORMATION: Antisense Oligonucleotide

<400> SEQUENCE: 16
ctttggcgga gcagcccatg                                               20

<210> SEQ ID NO 17
<211> LENGTH: 20
<212> TYPE: DNA
<213> ORGANISM: Artificial Sequence
<220> FEATURE:
<223> OTHER INFORMATION: Antisense Oligonucleotide

<400> SEQUENCE: 17
acctgctgct tgatgagcga                                               20

<210> SEQ ID NO 18
<211> LENGTH: 20
<212> TYPE: DNA
<213> ORGANISM: Artificial Sequence
<220> FEATURE:
<223> OTHER INFORMATION: Antisense Oligonucleotide

<400> SEQUENCE: 18
ctgcggcttc tcgcccttca                                               20

<210> SEQ ID NO 19
<211> LENGTH: 20
<212> TYPE: DNA
<213> ORGANISM: Artificial Sequence
<220> FEATURE:
<223> OTHER INFORMATION: Antisense Oligonucleotide

<400> SEQUENCE: 19
ccctgtacac gtagggcccg                                               20

<210> SEQ ID NO 20
<211> LENGTH: 20
<212> TYPE: DNA
<213> ORGANISM: Artificial Sequence
<220> FEATURE:
<223> OTHER INFORMATION: Antisense Oligonucleotide

<400> SEQUENCE: 20
cctggactcc ctgtacacgt                                               20

<210> SEQ ID NO 21
<211> LENGTH: 20
<212> TYPE: DNA
<213> ORGANISM: Artificial Sequence
<220> FEATURE:
<223> OTHER INFORMATION: Antisense Oligonucleotide
```

```
<400> SEQUENCE: 21
ttgttgaagg tgatgttgct                                                    20

<210> SEQ ID NO 22
<211> LENGTH: 20
<212> TYPE: DNA
<213> ORGANISM: Artificial Sequence
<220> FEATURE:
<223> OTHER INFORMATION: Antisense Oligonucleotide

<400> SEQUENCE: 22
gtcgttgttg ttgaaggtga                                                    20

<210> SEQ ID NO 23
<211> LENGTH: 20
<212> TYPE: DNA
<213> ORGANISM: Artificial Sequence
<220> FEATURE:
<223> OTHER INFORMATION: Antisense Oligonucleotide

<400> SEQUENCE: 23
gaaggacacg gtgtcgttgt                                                    20

<210> SEQ ID NO 24
<211> LENGTH: 20
<212> TYPE: DNA
<213> ORGANISM: Artificial Sequence
<220> FEATURE:
<223> OTHER INFORMATION: Antisense Oligonucleotide

<400> SEQUENCE: 24
tactcgagga aggacacggt                                                    20

<210> SEQ ID NO 25
<211> LENGTH: 20
<212> TYPE: DNA
<213> ORGANISM: Artificial Sequence
<220> FEATURE:
<223> OTHER INFORMATION: Antisense Oligonucleotide

<400> SEQUENCE: 25
gggcatgacg atgtagtcgc                                                    20

<210> SEQ ID NO 26
<211> LENGTH: 20
<212> TYPE: DNA
<213> ORGANISM: Artificial Sequence
<220> FEATURE:
<223> OTHER INFORMATION: Antisense Oligonucleotide

<400> SEQUENCE: 26
atgatgagct tcagggtcat                                                    20

<210> SEQ ID NO 27
<211> LENGTH: 20
<212> TYPE: DNA
<213> ORGANISM: Artificial Sequence
<220> FEATURE:
<223> OTHER INFORMATION: Antisense Oligonucleotide

<400> SEQUENCE: 27
gcggttcatg aaggcacgtt                                                    20

<210> SEQ ID NO 28
<211> LENGTH: 20
```

```
<212> TYPE: DNA
<213> ORGANISM: Artificial Sequence
<220> FEATURE:
<223> OTHER INFORMATION: Antisense Oligonucleotide

<400> SEQUENCE: 28
cacatgatct cacccacagt                                               20

<210> SEQ ID NO 29
<211> LENGTH: 20
<212> TYPE: DNA
<213> ORGANISM: Artificial Sequence
<220> FEATURE:
<223> OTHER INFORMATION: Antisense Oligonucleotide

<400> SEQUENCE: 29
ggtccttgta gccccacatg                                               20

<210> SEQ ID NO 30
<211> LENGTH: 20
<212> TYPE: DNA
<213> ORGANISM: Artificial Sequence
<220> FEATURE:
<223> OTHER INFORMATION: Antisense Oligonucleotide

<400> SEQUENCE: 30
gatcctgctg atgttctgga                                               20

<210> SEQ ID NO 31
<211> LENGTH: 20
<212> TYPE: DNA
<213> ORGANISM: Artificial Sequence
<220> FEATURE:
<223> OTHER INFORMATION: Antisense Oligonucleotide

<400> SEQUENCE: 31
gttccacttg tccacgaggt                                               20

<210> SEQ ID NO 32
<211> LENGTH: 20
<212> TYPE: DNA
<213> ORGANISM: Artificial Sequence
<220> FEATURE:
<223> OTHER INFORMATION: Antisense Oligonucleotide

<400> SEQUENCE: 32
agaagtcaac cttgctcagc                                               20

<210> SEQ ID NO 33
<211> LENGTH: 20
<212> TYPE: DNA
<213> ORGANISM: Artificial Sequence
<220> FEATURE:
<223> OTHER INFORMATION: Antisense Oligonucleotide

<400> SEQUENCE: 33
atcatgttgc actgatcgga                                               20

<210> SEQ ID NO 34
<211> LENGTH: 20
<212> TYPE: DNA
<213> ORGANISM: Artificial Sequence
<220> FEATURE:
<223> OTHER INFORMATION: Antisense Oligonucleotide

<400> SEQUENCE: 34
```
ccattgatca tgttgcactg                                            20

<210> SEQ ID NO 35
<211> LENGTH: 20
<212> TYPE: DNA
<213> ORGANISM: Artificial Sequence
<220> FEATURE:
<223> OTHER INFORMATION: Antisense Oligonucleotide

<400> SEQUENCE: 35
gactccttgt acattagctt                                            20

<210> SEQ ID NO 36
<211> LENGTH: 20
<212> TYPE: DNA
<213> ORGANISM: Artificial Sequence
<220> FEATURE:
<223> OTHER INFORMATION: Antisense Oligonucleotide

<400> SEQUENCE: 36
cagaagcctt cgttgggtgg                                            20

<210> SEQ ID NO 37
<211> LENGTH: 20
<212> TYPE: DNA
<213> ORGANISM: Artificial Sequence
<220> FEATURE:
<223> OTHER INFORMATION: Antisense Oligonucleotide

<400> SEQUENCE: 37
ctccaggcac gggcagaagc                                            20

<210> SEQ ID NO 38
<211> LENGTH: 20
<212> TYPE: DNA
<213> ORGANISM: Artificial Sequence
<220> FEATURE:
<223> OTHER INFORMATION: Antisense Oligonucleotide

<400> SEQUENCE: 38
aggccagtca ccgcttctgc                                            20

<210> SEQ ID NO 39
<211> LENGTH: 20
<212> TYPE: DNA
<213> ORGANISM: Artificial Sequence
<220> FEATURE:
<223> OTHER INFORMATION: Antisense Oligonucleotide

<400> SEQUENCE: 39
tcctggttag ggtgcaggcc                                            20

<210> SEQ ID NO 40
<211> LENGTH: 20
<212> TYPE: DNA
<213> ORGANISM: Artificial Sequence
<220> FEATURE:
<223> OTHER INFORMATION: Antisense Oligonucleotide

<400> SEQUENCE: 40
aatgcctgcg acagatttca                                            20

<210> SEQ ID NO 41
<211> LENGTH: 20
<212> TYPE: DNA
<213> ORGANISM: Artificial Sequence

```
<220> FEATURE:
<223> OTHER INFORMATION: Antisense Oligonucleotide

<400> SEQUENCE: 41
cccagtttgt ccaatgcctg                                               20

<210> SEQ ID NO 42
<211> LENGTH: 20
<212> TYPE: DNA
<213> ORGANISM: Artificial Sequence
<220> FEATURE:
<223> OTHER INFORMATION: Antisense Oligonucleotide

<400> SEQUENCE: 42
cggcaggacc acaggctcaa                                               20

<210> SEQ ID NO 43
<211> LENGTH: 20
<212> TYPE: DNA
<213> ORGANISM: Artificial Sequence
<220> FEATURE:
<223> OTHER INFORMATION: Antisense Oligonucleotide

<400> SEQUENCE: 43
cccgctctct gcaaaccaga                                               20

<210> SEQ ID NO 44
<211> LENGTH: 20
<212> TYPE: DNA
<213> ORGANISM: Artificial Sequence
<220> FEATURE:
<223> OTHER INFORMATION: Antisense Oligonucleotide

<400> SEQUENCE: 44
cgccaggagg acgtactggg                                               20

<210> SEQ ID NO 45
<211> LENGTH: 20
<212> TYPE: DNA
<213> ORGANISM: Artificial Sequence
<220> FEATURE:
<223> OTHER INFORMATION: Antisense Oligonucleotide

<400> SEQUENCE: 45
gcatttctct tggctccgga                                               20

<210> SEQ ID NO 46
<211> LENGTH: 20
<212> TYPE: DNA
<213> ORGANISM: Artificial Sequence
<220> FEATURE:
<223> OTHER INFORMATION: Antisense Oligonucleotide

<400> SEQUENCE: 46
taaatagcat ttctcttggc                                               20

<210> SEQ ID NO 47
<211> LENGTH: 20
<212> TYPE: DNA
<213> ORGANISM: Artificial Sequence
<220> FEATURE:
<223> OTHER INFORMATION: Antisense Oligonucleotide

<400> SEQUENCE: 47
ggcctgaatg gcctcccttat                                              20
```

<210> SEQ ID NO 48
<211> LENGTH: 20
<212> TYPE: DNA
<213> ORGANISM: Artificial Sequence
<220> FEATURE:
<223> OTHER INFORMATION: Antisense Oligonucleotide

<400> SEQUENCE: 48
atgtcatcag ggattcagaa                                               20

<210> SEQ ID NO 49
<211> LENGTH: 20
<212> TYPE: DNA
<213> ORGANISM: Artificial Sequence
<220> FEATURE:
<223> OTHER INFORMATION: Antisense Oligonucleotide

<400> SEQUENCE: 49
ttcctgcagc acagagccct                                               20

<210> SEQ ID NO 50
<211> LENGTH: 20
<212> TYPE: DNA
<213> ORGANISM: Artificial Sequence
<220> FEATURE:
<223> OTHER INFORMATION: Antisense Oligonucleotide

<400> SEQUENCE: 50
gttttgcttc ctgcagcaca                                               20

<210> SEQ ID NO 51
<211> LENGTH: 20
<212> TYPE: DNA
<213> ORGANISM: Artificial Sequence
<220> FEATURE:
<223> OTHER INFORMATION: Antisense Oligonucleotide

<400> SEQUENCE: 51
tcaggaccct acagttttgc                                               20

<210> SEQ ID NO 52
<211> LENGTH: 20
<212> TYPE: DNA
<213> ORGANISM: Artificial Sequence
<220> FEATURE:
<223> OTHER INFORMATION: Antisense Oligonucleotide

<400> SEQUENCE: 52
cgcatgtgtg tatgtgtgcc                                               20

<210> SEQ ID NO 53
<211> LENGTH: 20
<212> TYPE: DNA
<213> ORGANISM: Artificial Sequence
<220> FEATURE:
<223> OTHER INFORMATION: Antisense Oligonucleotide

<400> SEQUENCE: 53
tccctgagtg tctgcacaag                                               20

<210> SEQ ID NO 54
<211> LENGTH: 20
<212> TYPE: DNA
<213> ORGANISM: Artificial Sequence
<220> FEATURE:
<223> OTHER INFORMATION: Antisense Oligonucleotide

```
<400> SEQUENCE: 54
ctccatccct gagtgtctgc                                              20

<210> SEQ ID NO 55
<211> LENGTH: 20
<212> TYPE: DNA
<213> ORGANISM: Artificial Sequence
<220> FEATURE:
<223> OTHER INFORMATION: Antisense Oligonucleotide

<400> SEQUENCE: 55
agtgcttgtt gacgagcctc                                              20

<210> SEQ ID NO 56
<211> LENGTH: 20
<212> TYPE: DNA
<213> ORGANISM: Artificial Sequence
<220> FEATURE:
<223> OTHER INFORMATION: Antisense Oligonucleotide

<400> SEQUENCE: 56
tggtcagcct gtgggccacg                                              20

<210> SEQ ID NO 57
<211> LENGTH: 20
<212> TYPE: DNA
<213> ORGANISM: Artificial Sequence
<220> FEATURE:
<223> OTHER INFORMATION: Antisense Oligonucleotide

<400> SEQUENCE: 57
aacgggacag gccaggctca                                              20

<210> SEQ ID NO 58
<211> LENGTH: 20
<212> TYPE: DNA
<213> ORGANISM: Artificial Sequence
<220> FEATURE:
<223> OTHER INFORMATION: Antisense Oligonucleotide

<400> SEQUENCE: 58
caacggctga acgggacagg                                              20

<210> SEQ ID NO 59
<211> LENGTH: 20
<212> TYPE: DNA
<213> ORGANISM: Artificial Sequence
<220> FEATURE:
<223> OTHER INFORMATION: Antisense Oligonucleotide

<400> SEQUENCE: 59
acaccgggac tgcagtgttt                                              20

<210> SEQ ID NO 60
<211> LENGTH: 20
<212> TYPE: DNA
<213> ORGANISM: Artificial Sequence
<220> FEATURE:
<223> OTHER INFORMATION: Antisense Oligonucleotide

<400> SEQUENCE: 60
aaggccaaag ctcgtgccag                                              20

<210> SEQ ID NO 61
```

```
<211> LENGTH: 20
<212> TYPE: DNA
<213> ORGANISM: Artificial Sequence
<220> FEATURE:
<223> OTHER INFORMATION: Antisense Oligonucleotide

<400> SEQUENCE: 61
cgaggcctgt gtaaaggcgc                                              20

<210> SEQ ID NO 62
<211> LENGTH: 20
<212> TYPE: DNA
<213> ORGANISM: Artificial Sequence
<220> FEATURE:
<223> OTHER INFORMATION: Antisense Oligonucleotide

<400> SEQUENCE: 62
tgcacagggc atcttgtgct                                              20

<210> SEQ ID NO 63
<211> LENGTH: 20
<212> TYPE: DNA
<213> ORGANISM: Artificial Sequence
<220> FEATURE:
<223> OTHER INFORMATION: Antisense Oligonucleotide

<400> SEQUENCE: 63
accctcgggc agctgcacag                                              20

<210> SEQ ID NO 64
<211> LENGTH: 20
<212> TYPE: DNA
<213> ORGANISM: Artificial Sequence
<220> FEATURE:
<223> OTHER INFORMATION: Antisense Oligonucleotide

<400> SEQUENCE: 64
agtgcctgtg aagacttcgg                                              20

<210> SEQ ID NO 65
<211> LENGTH: 20
<212> TYPE: DNA
<213> ORGANISM: Artificial Sequence
<220> FEATURE:
<223> OTHER INFORMATION: Antisense Oligonucleotide

<400> SEQUENCE: 65
cgccagacaa cccgatgcag                                              20

<210> SEQ ID NO 66
<211> LENGTH: 20
<212> TYPE: DNA
<213> ORGANISM: Artificial Sequence
<220> FEATURE:
<223> OTHER INFORMATION: Antisense Oligonucleotide

<400> SEQUENCE: 66
ctcagtccat aggatgatgt                                              20

<210> SEQ ID NO 67
<211> LENGTH: 20
<212> TYPE: DNA
<213> ORGANISM: Artificial Sequence
<220> FEATURE:
<223> OTHER INFORMATION: Antisense Oligonucleotide

<400> SEQUENCE: 67
```
cagagagtgg ccggctcagt                                              20

<210> SEQ ID NO 68
<211> LENGTH: 20
<212> TYPE: DNA
<213> ORGANISM: Artificial Sequence
<220> FEATURE:
<223> OTHER INFORMATION: Antisense Oligonucleotide

<400> SEQUENCE: 68
cacagcctgc gccacttcgg                                              20

<210> SEQ ID NO 69
<211> LENGTH: 20
<212> TYPE: DNA
<213> ORGANISM: Artificial Sequence
<220> FEATURE:
<223> OTHER INFORMATION: Antisense Oligonucleotide

<400> SEQUENCE: 69
tcacctcagc ctgggcacct                                              20

<210> SEQ ID NO 70
<211> LENGTH: 20
<212> TYPE: DNA
<213> ORGANISM: Artificial Sequence
<220> FEATURE:
<223> OTHER INFORMATION: Antisense Oligonucleotide

<400> SEQUENCE: 70
ggtttgcccc agggtccagg                                              20

<210> SEQ ID NO 71
<211> LENGTH: 20
<212> TYPE: DNA
<213> ORGANISM: Artificial Sequence
<220> FEATURE:
<223> OTHER INFORMATION: Antisense Oligonucleotide

<400> SEQUENCE: 71
tttctattcc agtagaaaag                                              20

<210> SEQ ID NO 72
<211> LENGTH: 20
<212> TYPE: DNA
<213> ORGANISM: Artificial Sequence
<220> FEATURE:
<223> OTHER INFORMATION: Antisense Oligonucleotide

<400> SEQUENCE: 72
tttattactt caagagtgaa                                              20

<210> SEQ ID NO 73
<211> LENGTH: 20
<212> TYPE: DNA
<213> ORGANISM: Artificial Sequence
<220> FEATURE:
<223> OTHER INFORMATION: Antisense Oligonucleotide

<400> SEQUENCE: 73
cctcaggacc ttggctccgg                                              20

<210> SEQ ID NO 74
<211> LENGTH: 20
<212> TYPE: DNA

```
<213> ORGANISM: Artificial Sequence
<220> FEATURE:
<223> OTHER INFORMATION: Antisense Oligonucleotide

<400> SEQUENCE: 74
tgtcacagag gcaggcatcc                                                    20

<210> SEQ ID NO 75
<211> LENGTH: 20
<212> TYPE: DNA
<213> ORGANISM: Artificial Sequence
<220> FEATURE:
<223> OTHER INFORMATION: Antisense Oligonucleotide

<400> SEQUENCE: 75
acctcagcaa acaaggctgt                                                    20

<210> SEQ ID NO 76
<211> LENGTH: 20
<212> TYPE: DNA
<213> ORGANISM: Artificial Sequence
<220> FEATURE:
<223> OTHER INFORMATION: Antisense Oligonucleotide

<400> SEQUENCE: 76
ccaggatttg tagataaatg                                                    20

<210> SEQ ID NO 77
<211> LENGTH: 20
<212> TYPE: DNA
<213> ORGANISM: Artificial Sequence
<220> FEATURE:
<223> OTHER INFORMATION: Antisense Oligonucleotide

<400> SEQUENCE: 77
agagagcaaa ggccttagaa                                                    20

<210> SEQ ID NO 78
<211> LENGTH: 20
<212> TYPE: DNA
<213> ORGANISM: Artificial Sequence
<220> FEATURE:
<223> OTHER INFORMATION: Antisense Oligonucleotide

<400> SEQUENCE: 78
agtcccgggc acctaaatcc                                                    20

<210> SEQ ID NO 79
<211> LENGTH: 20
<212> TYPE: DNA
<213> ORGANISM: Artificial Sequence
<220> FEATURE:
<223> OTHER INFORMATION: Antisense Oligonucleotide

<400> SEQUENCE: 79
caaatctgaa ttgcgcgacc                                                    20

<210> SEQ ID NO 80
<211> LENGTH: 20
<212> TYPE: DNA
<213> ORGANISM: Artificial Sequence
<220> FEATURE:
<223> OTHER INFORMATION: Antisense Oligonucleotide

<400> SEQUENCE: 80
gtgttcaaat ctgaattgcg                                                    20
```

<210> SEQ ID NO 81
<211> LENGTH: 20
<212> TYPE: DNA
<213> ORGANISM: Artificial Sequence
<220> FEATURE:
<223> OTHER INFORMATION: Antisense Oligonucleotide

<400> SEQUENCE: 81
ggccagtggt tttatgcccc                                            20

<210> SEQ ID NO 82
<211> LENGTH: 20
<212> TYPE: DNA
<213> ORGANISM: Artificial Sequence
<220> FEATURE:
<223> OTHER INFORMATION: Antisense Oligonucleotide

<400> SEQUENCE: 82
cggcaggtgg ccagtggttt                                            20

<210> SEQ ID NO 83
<211> LENGTH: 20
<212> TYPE: DNA
<213> ORGANISM: Artificial Sequence
<220> FEATURE:
<223> OTHER INFORMATION: Antisense Oligonucleotide

<400> SEQUENCE: 83
ccgcagaggc acggtggatc                                            20

<210> SEQ ID NO 84
<211> LENGTH: 20
<212> TYPE: DNA
<213> ORGANISM: Artificial Sequence
<220> FEATURE:
<223> OTHER INFORMATION: Antisense Oligonucleotide

<400> SEQUENCE: 84
cggcacgtac tgaacctgca                                            20

<210> SEQ ID NO 85
<211> LENGTH: 20
<212> TYPE: DNA
<213> ORGANISM: Artificial Sequence
<220> FEATURE:
<223> OTHER INFORMATION: Antisense Oligonucleotide

<400> SEQUENCE: 85
tctaatgagc ttccctgcta                                            20

<210> SEQ ID NO 86
<211> LENGTH: 20
<212> TYPE: DNA
<213> ORGANISM: Artificial Sequence
<220> FEATURE:
<223> OTHER INFORMATION: Antisense Oligonucleotide

<400> SEQUENCE: 86
agaccagcct gggcaacata                                            20

<210> SEQ ID NO 87
<211> LENGTH: 20
<212> TYPE: DNA
<213> ORGANISM: Artificial Sequence
<220> FEATURE:

-continued

```
<223> OTHER INFORMATION: Antisense Oligonucleotide

<400> SEQUENCE: 87
cccagtttgt ctggaaataa                                              20

<210> SEQ ID NO 88
<211> LENGTH: 20
<212> TYPE: DNA
<213> ORGANISM: Artificial Sequence
<220> FEATURE:
<223> OTHER INFORMATION: Antisense Oligonucleotide

<400> SEQUENCE: 88
tggccccgct ctgaggagac                                              20

<210> SEQ ID NO 89
<211> LENGTH: 20
<212> TYPE: DNA
<213> ORGANISM: Artificial Sequence
<220> FEATURE:
<223> OTHER INFORMATION: Antisense Oligonucleotide

<400> SEQUENCE: 89
ctgcagatct tatgttctgg                                              20

<210> SEQ ID NO 90
<211> LENGTH: 20
<212> TYPE: DNA
<213> ORGANISM: Artificial Sequence
<220> FEATURE:
<223> OTHER INFORMATION: Antisense Oligonucleotide

<400> SEQUENCE: 90
ctctctctgt cgcccaggct                                              20

<210> SEQ ID NO 91
<211> LENGTH: 20
<212> TYPE: DNA
<213> ORGANISM: Artificial Sequence
<220> FEATURE:
<223> OTHER INFORMATION: Antisense Oligonucleotide

<400> SEQUENCE: 91
cctcaggacc ctgtggagaa                                              20
```

ANTISENSE MODULATION OF CD36L 1 EXPRESSION

FIELD OF THE INVENTION

The present invention provides compositions and methods for modulating the expression of CD36L1. In particular, this invention relates to compounds, particularly oligonucleotides, specifically hybridizable with nucleic acids encoding CD36L1. Such compounds have been shown to modulate the expression of CD36L1.

BACKGROUND OF THE INVENTION

Atherosclerosis is the major causative factor of heart disease and stroke, and cardiovascular disease is the leading cause of death in Western countries. Dyslipidemia is a primary contributor to atherosclerosis. Because triglycerides are insoluble in the bloodstream, they are packaged for plasma transport into micelle-like lipoprotein particles composed of protein, phospholipid and cholesterol shells surrounding a non-polar core of acylglycerols, free cholesterol, and cholesterol esters. Lipoproteins have been classified into five broad categories on the basis of their functional and physical properties: chylomicrons (which transport dietary lipids from intestine to tissues); very low density lipoproteins (VLDL), intermediate density lipoproteins (IDL and low density lipoproteins (LDL), (all of which transport triacylglycerols and cholesterol from the liver to tissues); and high density lipoproteins (HDL) (which transport endogenous cholesterol from tissues to the liver, as well as mediating selective cholesteryl ester delivery to steroidogenic tissues). All of these particles undergo continuous metabolic processing and have somewhat variable properties and compositions. Plasma concentrations of LDL and HDL are directly and inversely related, respectively, to the risk of atherosclerotic cardiovascular disease (Acton et al., *Mol. Med. Today*, 1999, 5, 518–524; Krieger, *Proc. Natl. Acad. Sci. U. S. A.*, 1998, 95, 4077–4080).

A variety of integral membrane glycoproteins, collectively designated as scavenger receptors, mediate the binding and uptake of native and modified lipoproteins. A structurally diverse group, the scavenger receptors have been subclassified according to their composition: the class A scavenger receptors are trimeric glycoproteins whereas the class B scavenger receptors are composed of a single glycosylated polypeptide. The scavenger receptors are able to interact with a broad range of ligands, including modified proteins, lipoproteins and some polyanionic polysaccharides, as well as with in vitro oxidized and senescent cells, polyanionic phospholipids, and bacterial components (Calvo et al., *J. Lipid Res.*, 1998, 39, 777–788).

LDL catabolism involves endocytosis and degradation of the entire lipoprotein particle by a well-characterized LDL receptor. In contrast, HDL particles deliver the cholesterol component to cells without the degradation of the protein component of HDL; this process is known as selective lipid uptake. Thus, HDL delivers cholesteryl ester to nonplacental steroidogenic tissues (ovary, adrenal gland, and testis) for hormone synthesis and transport cholesterol from extrahepatic tissues to the liver (reverse cholesterol transport), and the receptor that mediates HDL-binding and selective lipid uptake is the class B scavenger receptor, CD36 antigen-like 1 (CD36L1; also known as CD36L1; CLA-1; and scavenger receptor class B type 1; SRB1; and the mouse homologue, SR-BI) (Acton et al., *Science*, 1996, 271, 518–520).

A human CD36L1 cDNA representing a third member of a novel gene family that also includes CD36 (the thrombospondin and collagen type I receptor) and the lysosomal integrin membrane protein II (LIMPII) was identified and isolated from the melanoma cell lines 14Mel, SKMel131, and SKMel37 as well as from Burkitt lymphoma cell Ramos using a PCR-based approach. Subsequently, the full-length CD36L1 gene was cloned from a cDNA library derived from PMA-stimulated HLA60 cells. An alternative splice form of the CD36L1 mRNA was also identified, and Northern analysis revealed the presence of a 2.9-kilobase transcript in all cell types examined, but expression varied significantly with cell type, with low levels of CD36L1 expression in lymphoid-derived cells and higher levels of expression in melanoma cells (Calvo and Vega, *J. Biol. Chem.*, 1993, 268, 18929–18935). The hamster CD36L1 gene was identified by expression cloning as a class B scavenger receptor which bound modified lipoproteins such as acetylated LDL and oxidized LDL as well as native LDL (Acton et al., *J. Biol. Chem.*, 1994, 269, 21003–21009). Using a panel of human-hamster somatic cell hybrids, the human CD36L1 gene was mapped to chromosome 12 (Calvo et al., *Genomics*, 1995, 25, 100–106), later refined to the 12q24.2 chromosomal locus (Cao et al., *J. Biol. Chem.*, 1997, 272, 33068–33076).

The uptake of lipoprotein-derived cholesteryl esters through the CD36L1 pathway represents a high-capacity, hormone-inducible cholesterol delivery system to cells. CD36L1 was observed to transfer more tree cholesterol than cholesteryl esters to cells from either LDL or HDL, and most of the cholesterol that entered cells via CD36L1 was available for efflux, suggesting that most of this cholesterol remained in the plasma membrane. While CD36L1 was able to mediate the selective uptake of core lipids from both classes of lipoproteins, HDL was a more efficient donor of cholesteryl esters than LDL. Sterols transported from LDL or HDL by CD36L1 were equally effective in delivering cholesterol to the intracellular regulatory cholesterol pool, resulting in important regulatory effects on SREBP-2 (sterol regulatory element binding protein-2) and HMG-COA reductase, two genes important in cholesterol metabolism. Thus, CD36L1 is equally efficient at mediating the import and export of cholesterol to and from cells to lipoproteins and other acceptors, resulting in a rapid exchange of cholesterol between lipoproteins and cell membranes (Stangl et al., *J. Biol. Chem.*, 1999, 274, 32692–32698).

The C-terminal linking and modulating protein (CLAMP) was identified in rat liver sinusoidal plasma membrane as a protein associated with the C-terminus of the CD36L1 protein. CLAMP may be involved in modulating the intracellular transport and metabolism of cholesteryl esters taken up from HDL by CD36L1 (Ikemoto et al., *Proc. Natl. Acad. Sci. U.S.A.*, 2000, 97, 6538–6543).

The protective, antiatherogenic effect of HDL is believed to involve the reverse transport of cholesterol from cells in the arterial wall to the liver for disposal. HDL also reduces endotoxic activity of cholesterol by complexation and neutralization of lipopolysaccharide (LPS). CD36L1 expression is upregulated during phagocytic as well as dendritic differentiation of monocytes, indicating a role for this receptor in cholesterol homeostasis in phagocytes and antigen-presenting cells. Peroxisome proliferator-activated receptors (PPARs) are nuclear receptors that heterodimerize with the retinoid X receptor to act as ligand-activated transcriptional regulators of genes controlling lipid and glucose metabolism. CD36L1 is expressed in atherosclerotic lesion macrophages and is induced by PPAR activation, identifying a mechanism by which PPARs regulates cholesterol homeostasis via CD36L1 expression in atherosclerotic lesion macrophages (Chinetti et al., *Circulation*, 2000, 101, 2411–2417).

Conversely, CD36L1 expression is suppressed in monocytes and macrophages by proinflammatory stimuli such as LPS, the cytokine interferon-gamma (IFN-γ), and tumor necrosis factor-alpha (TNF-α). Expression of CD36L1 mRNA and protein was studied in an immortalized human aortic intima smooth-muscle cell line ISS10, and IFN-γ was found to inhibit CD36L1 protein, but not mRNA expression in smooth-muscle cells, indicating that CD36L1 could play an important role in atherogenesis and that IFN-γ might impact the progression of an atherosclerotic lesion (Imachi et al., *Horm. Metab. Res.*, 2001, 33, 389–393). It has been hypothesized that suppression of CD36L1 expression during early inflammation decreases cholesterol efflux from monocytes/macrophages and thereby reduces the clearance of HDL particles from the circulation, helping to maintain the lipoprotein status in the serum important for neutralizing LPS in the circulation as a short-term means of host defense (Buechler et al., *Biochem. Biophys. Res. Commun.*, 1999, 262, 251–254)

The specific recognition of anionic phospholipids in the outer leaflets of cell membranes and lipoproteins by cell surface receptors it believed to play an important role in physiologic and pathophysiologic processes such as recognition of damaged or senescent cells by the reticuloendothelial system and lipoprotein homeostasis. In addition to its role in the absorption of dietary lipids, CD36L1 can bind to the membrane phospholipid phosphatidylserine (PS) and phosphatidylinositol (PI)-containing liposomes with high affinity (Rigotti et al., *The J. Biol. Chem.*, 1995, 270, 16221–16224). Chinese hamster ovary (CHO) cell lines constitutively expressing CD36L1 were found to recognize both negatively charged liposomes and apoptotic cells presumably bearing PS in the outer layer of the plasma membrane (Fukasawa et al., *Exp. Cell Res.*, 1996, 222, 246–250). Furthermore, because expression of human CD36L1 was found in circulating monocytes and, to a lesser extent, in fully differentiated macrophages, and because apoptotic thymocytes were able to bind cells transfected with CD36L1, it appears that CD36L1 not only acts as a "docking receptor" for HDL in liver and steroidogenic tissues, but also has alternative functions in leukocytes as a means for recognition of damaged cells (Murao et al., *J. Biol. Chem.*, 1997, 272, 17551–17557).

Aberrant cell proliferation is one of the hallmarks of carcinogenesis, and cholesterol is believed to be involved in cell proliferation and cancer progression. An association between high HDL and cholesterol and the incidence of breast cancer, possibly related to estrogen metabolism, has been reported. In a study of pathways that could contribute to enhanced proliferation rates of cancer cells, the human breast cancer HBL-100 cell line was able to acquire HDL-cholesteryl esters via selective uptake mediated by CD36L1. Subsequent hydrolysis by hormone-sensitive lipase provided a significant contribution to the free cholesterol pool in rapidly dividing HBL-100 cells, potentially reflecting a source of precursors for hormone synthesis and cancer cell proliferation (Pussinen et al., *Biochem. J.*, 2000, 349, 559–566).

CD36L1 is also involved in synthesis of steroid hormones. Northern analyses of 42 tissue samples revealed expression of CD36L1 mRNA in normal adult and fetal adrenal tissues as well as in pathological tissues, such as hyperplasias and adrenocortical adenomas. Adrenocortical carcinomas and the adrenals adjacent to Cushing's adenomas expressed lower levels of CD36L1 mRNA than did normal tissues, and the accumulation of CD36L1 mRNA in primary cultures of normal adrenocortical cells was up-regulated by adrenocorticotropic hormone (ACTH) in a dose- and time-dependent manner through the cAMP-dependent protein kinase pathway, suggesting that CD36L1 is involved in selective cholesterol uptake in human adrenocortical cells (Liu et al., *J. Clin. Endocrinol. Metab.*, 1997, 82, 2522–2527). The SF-1 protein, an orphan member of the nuclear hormone receptor family of transcription factors, is expressed at high levels in steroidogenic tissues and appears to regulate CD36L1. SF-1 binds, in a sequence-specific manner, to the promoter of CD36L1, and efficient transcription from the CD36L1 promoter in Y1 mouse adrenocortical cells was found to depend on an intact SF-1 site, suggesting that CD36L1 supplies selected tissues with lipoprotein-derived lipids and is part of the repertoire of SF-1 responsive genes involved in steroidogenesis (Cao et al., *J. Biol. Chem.*, 1997, 272, 33068–33076). In support of these findings, homozygous null CD36L1 knockout mice have been generated and used to show that CD36L1 is not only required for maintaining normal biliary cholesterol levels, but also for oocyte development and female fertility (Trigatti et al., *Proc. Natl. Acad. Sci. U. S. A.*, 1999, 96, 9322–9327). Thus, inhibition of CD36L1 could act as a means of reducing production of steroid hormones for contraception.

In another study of the effects of CD36L1 in mice, the transgene-induced overexpression of murine CD36L1 resulted in a stimulation of excretion of cholesterol into the bile and suppressed percentage dietary cholesterol absorption. Thus, by extension, accelerated reverse cholesterol transport and storage in the liver, induced by hepatic overproduction of CD36L1 might be associated with increase bile cholesterol content, increasing the risk of biliary cholesterol and gall stone disease in humans (Sehayek et al., *Proc. Natl. Acad. Sci. U. S. A.*, 1998, 95, 10194–10199).

Currently, there are no known therapeutic agents which effectively inhibit the synthesis of CD36L1 and to date, investigative strategies aimed at modulating CD36L1 function have involved the use of antisense oligonucleotides.

A phosphorothioate antisense oligonucleotide, 27 nucleotides in length, corresponding to the 5' end of the CD36L1 mRNA was used to suppress CD36L1 protein expression by 80% and to inhibit the binding of thymic macrophages and nursing thymic epithelial cells to apoptotic thymocytes by 40% (Imachi et al., *Lab. Invest.*, 2000, 80, 263–270).

Disclosed and claimed in U.S. Pat. No. 5,962,322 is the nucleic acid sequence for the hamster and murine CD36L1 genes and a method for selectively altering transport of lipid, cholesterol, lipoprotein or component thereof into and out of mammalian cells in an amount effective to alter plasma cholesterol comprising administering a composition in an amount effective to alter expression or activity of CD36L1 and thus alter the rate of clearance of the protein component of HDL as compared to the cholesterol ester component of the HDL, wherein transport of lipid, cholesterol, lipoprotein or component of the lipoprotein is inhibited or stimulated by administering a compound which binds to a regulatory nucleic acid sequence and therefore inhibits or increases expression of CD36L1, and wherein the compound is a viral vector encoding CD36L1. Direct inhibitors such as antisense oligonucleotides are generally disclosed (Kozarsky et al., 1999).

Disclosed and claimed in PCT publication WO 99/11288 is a method for modifying steroid production in a mammal comprising administering a compound altering the transfer of cholesterol or cholesteryl ester from high density lipoprotein or other lipoproteins via CD36L1 to liver or steroidogenic tissues, wherein the compound alters CD36L1 expression in the tissue, and wherein the compound alters binding of CD36L1 to high density lipoprotein including cholesteryl ester or other lipoproteins, or CD36L1 binding to lipoprotein or transfer of cholesteryl ester, and wherein the mammal is a female and the compound is administered in an amount effective to prevent normal reproductive function, and wherein the mammal has a disorder characterized by overproduction or underproduction of steroids, as well as a method of manufacture of said compound and a pharmaceutical composition for use in any one of said methods. Direct inhibitors such as antisense oligonucleotides are generally disclosed (Krieger, 1999).

Disclosed and claimed in U.S. Pat. No. 6,130,041 are isolated intronic and polymorphic nucleic acid variants of a genomic DNA comprising the human CD36L1 gene, a kit for amplifying and/or for determining the molecular structure of at least a portion of a CD36L1 gene, a method for determining whether a subject has, or is at risk of developing, a disease or condition associated with a specific allelic variant of a polymorphic region in the human CD36L1 gene, further comprising determining whether the CD36L1 gene of the subject comprises an allelic variant that is associated with a disease or condition, wherein the disease or condition is an abnormal lipid metabolism, inappropriate lipid levels, a cardiovascular disease, atherosclerosis, gallstone formation or an abnormal body mass index. Antisense techniques are generally disclosed (Acton, 2000).

Disclosed and claimed in U.S. Pat. No. 5,965,790 is an isolated nucleic acid molecule which is capable of hybridizing to a nucleic acid molecule consisting of the nucleotide sequence the human CD36L1 promoter or the complement thereof, wherein the nucleic acid is capable of modulating transcription of a gene operably linked to the nucleic acid, and wherein the gene encodes a CD36L1 receptor, and wherein the nucleic acid is capable of activating or enhancing transcription of said gene, as well as vectors, host cells, transgenic mice. Antisense oligonucleotides are generally disclosed (Acton, 1999).

The results of investigations of CD36L1 discussed herein suggest that pharmacological modulation of CD36L1 activity and/or expression may be an appropriate point for therapeutic intervention in pathologic conditions such as the overproduction of biliary cholesterol and gall stone disease, atherosclerosis and potentially, as a method of contraception. Consequently, there remains a long-felt need for therapeutic agents capable of inhibiting the function of CD36L1.

Antisense technology is emerging as an effective means of reducing the expression of specific gene products and may therefore serve as a unique strategy with which to modulate the expression of CD36L1.

The present invention provides compositions and methods for modulating CD36L1 expression.

SUMMARY OF THE INVENTION

The present invention is directed to compounds, particularly antisense oligonucleotides, which are targeted to a nucleic acid encoding CD36L1, and which modulate the expression of CD36L1. Pharmaceutical and other compositions comprising the compounds of the invention are also provided. Further provided are methods of modulating the expression of CD36L1 in cells or tissues comprising contacting said cells or tissues with one or more of the antisense compounds or compositions of the invention. Further provided are methods of treating an animal, particularly a human, suspected of having or being prone to a disease or condition associated with expression of CD36L1 by administering a therapeutically or prophylactically effective amount of one or more of the antisense compounds or compositions of the invention.

DETAILED DESCRIPTION OF THE INVENTION

The present invention employs oligomeric compounds, particularly antisense oligonucleotides, for use in modulating the function of nucleic acid molecules encoding CD36L1, ultimately modulating the amount of CD36L1 produced. This is accomplished by providing antisense compounds which specifically hybridize with one or more nucleic acids encoding CD36L1. As used herein, the terms "target nucleic acid" and "nucleic acid encoding CD36L1" encompass DNA encoding CD36L1, RNA (including pre-mRNA and mRNA) transcribed from such DNA, and also cDNA derived from such RNA. The specific hybridization of an oligomeric compound with its target nucleic acid interferes with the normal function of the nucleic acid. This modulation of function of a target nucleic acid by compounds which specifically hybridize to it is generally referred to as "antisense". The functions of DNA to be interfered with include replication and transcription. The functions of RNA to be interfered with include all vital functions such as, for example, translocation of the RNA to the site of protein translation, translation of protein from the RNA, splicing of the RNA to yield one or more mRNA species, and catalytic activity which may be engaged in or facilitated by the RNA. The overall effect of such interference with target nucleic acid function is modulation of the expression of CD36L1. In the context of the present invention, "modulation" means either an increase (stimulation) or a decrease (inhibition) in the expression of a gene. In the context of the present invention, inhibition is the preferred form of modulation of gene expression and mRNA is a preferred target.

It is preferred to target specific nucleic acids for antisense. "Targeting" an antisense compound to a particular nucleic acid, in the context of this invention, is a multistep process. The process usually begins with the identification of a nucleic acid sequence whose function is to be modulated. This may be, for example, a cellular gene (or mRNA transcribed from the gene) whose expression is associated with a particular disorder or disease state, or a nucleic acid molecule from an infectious agent. In the present invention, the target is a nucleic acid molecule encoding CD36L1. The targeting process also includes determination of a site or sites within this gene for the antisense interaction to occur such that the desired effect, e.g., detection or modulation of expression of the protein, will result. Within the context of the present invention, a preferred intragenic site is the region encompassing the translation initiation or termination codon of the open reading frame (ORF) of the gene. Since, as is known in the art, the translation initiation codon is typically 5'-AUG (in transcribed mRNA molecules; 5'-ATG in the corresponding DNA molecule), the translation initiation codon is also referred to as the "AUG codon," the "start codon" or the "AUG start codon". A minority of genes have a translation initiation codon having the RNA sequence 5'-GUG, 5'-UUG or 5'-CUG, and 5'-AUA, 5'-ACG and 5'-CUG have been shown to function in vivo. Thus, the terms "translation initiation codon" and "start codon" can encompass many codon sequences, even though the initiator amino acid in each instance is typically methionine (in eukaryotes) or formylmethionine (in prokaryotes). It is also known in the art that eukaryotic and prokaryotic genes may have two or more alternative start codons, any one of which may be preferentially utilized for translation initiation in a particular cell type or tissue, or under a particular set of conditions. In the context of the invention, "start codon" and "translation initiation codon" refer to the codon or codons that are used in vivo to initiate translation of an mRNA molecule transcribed from a gene encoding CD36L1, regardless of the sequence(s) of such codons.

It is also known in the art that a translation termination codon (or "stop codon") of a gene may have one of three sequences, i.e., 5'-UAA, 5'-UAG and 5'-UGA (the corresponding DNA sequences are 5'-TAA, 5'-TAG and 5'-TGA, respectively). The terms "start codon region" and "translation initiation codon region" refer to a portion of such an mRNA or gene that encompasses from about 25 to about 50 contiguous nucleotides in either direction (i.e., 5' or 3') from a translation initiation codon. Similarly, the terms "stop codon region" and "translation termination codon region" refer to a portion of such an mRNA or gene that encompasses from about 25 to about 50 contiguous nucleotides in either direction (i.e., 5' or 3') from a translation termination codon.

The open reading frame (ORF) or "coding region," which is known in the art to refer to the region between the translation initiation codon and the translation termination codon, is also a region which may be targeted effectively. Other target regions include the 5' untranslated region (5'UTR), known in the art to refer to the portion of an mRNA in the 5' direction from the translation initiation codon, and thus including nucleotides between the 5' cap site and the translation initiation codon of an mRNA or corresponding nucleotides on the gene, and the 3' untranslated region (3'UTR), known in the art to refer to the portion of an mRNA in the 3' direction from the translation termination codon, and thus including nucleotides between the translation termination codon and 3' end of an mRNA or corresponding nucleotides on the gene. The 5' cap of an mRNA comprises an N7-methylated guanosine residue joined to the 5'-most residue of the mRNA via a 5'—5' triphosphate linkage. The 5' cap region of an mRNA is considered to include the 5' cap structure itself as well as the first 50 nucleotides adjacent to the cap. The 5' cap region may also be a preferred target region.

Although some eukaryotic mRNA transcripts are directly translated, many contain one or more regions, known as "introns," which are excised from a transcript before it is translated. The remaining (and therefore translated) regions are known as "exons" and are spliced together to form a continuous mRNA sequence. mRNA splice sites, i.e., intron-exon junctions, may also be preferred target regions, and are particularly useful in situations where aberrant splicing is implicated in disease, or where an overproduction of a particular mRNA splice product is implicated in disease. Aberrant fusion junctions due to rearrangements or deletions are also preferred targets. It has also been found that introns can also be effective, and therefore preferred, target regions for antisense compounds targeted, for example, to DNA or pre-mRNA.

It is also known in the art that alternative RNA transcripts can be produced from the same genomic region of DNA. These alternative transcripts are generally known as "variants". More specifically, "pre-mRNA variants" are transcripts produced from the same genomic DNA that differ from other transcripts produced from the same genomic DNA in either their start or stop position and contain both intronic and extronic regions.

Upon excision of one or more exon or intron regions or portions thereof during splicing, pre-mRNA variants produce smaller "mRNA variants". Consequently, mRNA variants are processed pre-mRNA variants and each unique pre-mRNA variant must always produce a unique mRNA variant as a result of splicing. These mRNA variants are also known as "alternative splice variants". If no splicing of the pre-mRNA variant occurs then the pre-mRNA variant is identical to the mRNA variant.

It is also known in the art that variants can be produced through the use of alternative signals to start or stop transcription and that pre-mRNAs and mRNAs can possess more that one start codon or stop codon. Variants that originate from a pre-mRNA or mRNA that use alternative start codons are known as "alternative start variants" of that pre-mRNA or mRNA. Those transcripts that use an alternative stop codon are known as "alternative stop variants" of that pre-mRNA or mRNA. One specific type of alternative stop variant is the "polyA variant" in which the multiple transcripts produced result from the alternative selection of one of the "polyA stop signals" by the transcription machinery, thereby producing transcripts that terminate at unique polyA sites.

Once one or more target sites have been identified, oligonucleotides are chosen which are sufficiently complementary to the target, i.e., hybridize sufficiently well and with sufficient specificity, to give the desired effect.

In the context of this invention, "hybridization" means hydrogen bonding, which may be Watson-Crick, Hoogsteen or reversed Hoogsteen hydrogen bonding, between complementary nucleoside or nucleotide bases. For example, adenine and thymine are complementary nucleobases which pair through the formation of hydrogen bonds. "Complementary," as used herein, refers to the capacity for precise pairing between two nucleotides. For example, if a nucleotide at a certain position of an oligonucleotide is capable of hydrogen bonding with a nucleotide at the same position of a DNA or RNA molecule, then the oligonucleotide and the DNA or RNA are considered to be complementary to each other at that position. The oligonucleotide and the DNA or RNA are complementary to each other when a sufficient number of corresponding positions in each molecule are occupied by nucleotides which can hydrogen bond with each other. Thus, "specifically hybridizable" and "complementary" are terms which are used to indicate a sufficient degree of complementarity or precise pairing such that stable and specific binding occurs between the oligonucleotide and the DNA or RNA target. It is understood in the art that the sequence of an antisense compound need not be 100% complementary to that of its target nucleic acid to be specifically hybridizable. An antisense compound is specifically hybridizable when binding of the compound to the target DNA or RNA molecule interferes with the normal function of the target DNA or RNA to cause a loss of utility, and there is a sufficient degree of complementarity to avoid non-specific binding of the antisense compound to non-target sequences under conditions in which specific binding is desired, i.e., under physiological conditions in the case of in vivo assays or therapeutic treatment, and in the case of in vitro assays, under conditions in which the assays are performed.

Antisense and other compounds of the invention which hybridize to the target and inhibit expression of the target are identified through experimentation, and the sequences of these compounds are hereinbelow identified as preferred embodiments of the invention. The target sites to which these preferred sequences are complementary are hereinbelow referred to as "active sites" and are therefore preferred sites for targeting. Therefore another embodiment of the invention encompasses compounds which hybridize to these active sites.

Antisense compounds are commonly used as research reagents and diagnostics. For example, antisense oligonucleotides, which are able to inhibit gene expression with exquisite specificity, are often used by those of ordinary skill to elucidate the function of particular genes. Antisense compounds are also used, for example, to distinguish between functions of various members of a biological pathway. Antisense modulation has, therefore, been harnessed for research use.

For use in kits and diagnostics, the antisense compounds of the present invention, either alone or in combination with other antisense compounds or therapeutics, can be used as tools in differential and/or combinatorial analyses to elucidate expression patterns of a portion or the entire complement of genes expressed within cells and tissues.

Expression patterns within cells or tissues treated with one or more antisense compounds are compared to control cells or tissues not treated with antisense compounds and the patterns produced are analyzed for differential levels of gene expression as they pertain, for example, to disease association, signaling pathway, cellular localization, expression level, size, structure or function of the genes examined. These analyses can be performed on stimulated or unstimulated cells and in the presence or absence of other compounds which affect expression patterns.

Examples of methods of gene expression analysis known in the art include DNA arrays or microarrays (Brazma and Vilo, *FEBS Lett.*, 2000, 480, 17–24; Celis, et al., *FEBS Lett.*, 2000, 480, 2–16), SAGE (serial analysis of gene expression) (Madden, et al., *Drug Discov. Today*, 2000, 5, 415–425), READS (restriction enzyme amplification of digested cDNAs) (Prashar and Weissman, *Methods Enzymol.*, 1999, 303, 258–72), TOGA (total gene expression analysis) (Sutcliffe, et al., *Proc. Natl. Acad. Sci. U. S. A.*, 2000, 97, 1976–81), protein arrays and proteomics (Celis, et al., *FEBS Lett.*, 2000, 480, 2–16; Jungblut, et al., *Electrophoresis*, 1999, 20, 2100–10), expressed sequence tag (EST) sequencing (Celis, et al., *FEBS Lett.*, 2000, 480, 2–16; Larsson, et al., *J. Biotechnol.*, 2000, 80, 143–57), subtractive RNA fingerprinting (SuRF) (Fuchs, et al., *Anal. Biochem.*, 2000, 286, 91–98; Larson, et al., *Cytometry*, 2000, 41, 203–208), subtractive cloning, differential display (DD) (Jurecic and Belmont, *Curr. Opin. Microbiol.*, 2000, 3, 316–21), comparative genomic hybridization (Carulli, et al., *J. Cell Biochem. Suppl.*, 1998, 31, 286–96), FISH (fluorescent in situ hybridization) techniques (Going and Gusterson, *Eur. J. Cancer*, 1999, 35, 1895–904) and mass spectrometry methods (reviewed in (To, *Comb. Chem. High Throughput Screen*, 2000, 3, 235–41).

The specificity and sensitivity of antisense is also harnessed by those of skill in the art for therapeutic uses. Antisense oligonucleotides have been employed as therapeutic moieties in the treatment of disease states in animals and man. Antisense oligonucleotide drugs, including ribozymes, have been safely and effectively administered to humans and numerous clinical trials are presently underway. It is thus established that oligonucleotides can be useful therapeutic modalities that can be configured to be useful in treatment regimes for treatment of cells, tissues and animals, especially humans.

In the context of this invention, the term "oligonucleotide" refers to an oligomer or polymer of ribonucleic acid (RNA) or deoxyribonucleic acid (DNA) or mimetics thereof. This term includes oligonucleotides composed of naturally-occurring nucleobases, sugars and covalent internucleoside (backbone) linkages as well as oligonucleotides having non-naturally-occurring portions which function similarly. Such modified or substituted oligonucleotides are often preferred over native forms because of desirable properties such as, for example, enhanced cellular uptake, enhanced affinity for nucleic acid target and increased stability in the presence of nucleases.

While antisense oligonucleotides are a preferred form of antisense compound, the present invention comprehends other oligomeric antisense compounds, including but not limited to oligonucleotide mimetics such as are described below. The antisense compounds in accordance with, this invention preferably comprise from about 8 to about 50 nucleobases (i.e. from about 8 to about 50 linked nucleosides). Particularly preferred antisense compounds are antisense oligonucleotides, even more preferably those comprising from about 12 to about 30 nucleobases. Antisense compounds include ribozymes, external guide sequence (EGS) oligonucleotides (oligozymes), and other short catalytic RNAs or catalytic oligonucleotides which hybridize to the target nucleic acid and modulate its expression.

As is known in the art, a nucleoside is a base-sugar combination. The base portion of the nucleoside is normally a heterocyclic base. The two most common classes of such heterocyclic bases are the purines and the pyrimidines. Nucleotides are nucleosides that further include a phosphate group covalently linked to the sugar portion of the nucleoside. For those nucleosides that include a pentofuranosyl sugar, the phosphate group can be linked to either the 2', 3' or 5' hydroxyl moiety of the sugar. In forming oligonucleotides, the phosphate groups covalently link adjacent nucleosides to one another to form a linear polymeric compound. In turn the respective ends of this linear polymeric structure can be further joined to form a circular structure, however, open linear structures are generally preferred. Within the oligonucleotide structure, the phosphate groups are commonly referred to as forming the internucleoside backbone of the oligonucleotide. The normal linkage or backbone of RNA and DNA is a 3' to 5' phosphodiester linkage.

Specific examples of preferred antisense compounds useful in this invention include oligonucleotides containing modified backbones or non-natural internucleoside linkages. As defined in this specification, oligonucleotides having modified backbones include those that retain a phosphorus atom in the backbone and those that do not have a phosphorus atom in the backbone. For the purposes of this specification, and as sometimes referenced in the art, modified oligonucleotides that do not have a phosphorus atom in their internucleoside backbone can also be considered to be oligonucleosides.

Preferred modified oligonucleotide backbones include, for example, phosphorothioates, chiral phosphorothioates, phosphorodithioates, phosphotriesters, aminoalkylphosphotriesters, methyl and other alkyl phosphonates including 3'-alkylene phosphonates, 5'-alkylene phosphonates and chiral phosphonates, phosphinates, phosphoramidates including 3'-amino phosphoramidate and aminoalkylphosphoramidates, thionophosphoramidates, thionoalkylphosphonates, thionoalkylphosphotriesters, selenophosphates and borano-phosphates having normal 3'-5' linkages, 2'-5' linked analogs of these, and those having inverted polarity wherein one or more internucleotide linkages is a 3' to 3', 5' to 5' or 2' to 2' linkage. Preferred oligonucleotides having inverted polarity comprise a single 3' to 3' linkage at the 3'-most internucleotide linkage i.e. a single inverted nucleoside residue which may be abasic (the nucleobase is missing or has a hydroxyl group in place thereof). Various salts, mixed salts and free acid forms are also included.

Representative United States patents that teach the preparation of the above phosphorus-containing linkages include, but are not limited to, U.S. Pat. Nos.: 3,687,808; 4,469,863; 4,476,301; 5,023,243; 5,177,196; 5,188,897; 5,264,423; 5,276,019; 5,278,302; 5,286,717; 5,321,131; 5,399,676; 5,405,939; 5,453,496; 5,455,233; 5,466,677; 5,476,925; 5,519,126; 5,536,821; 5,541,306; 5,550,111; 5,563,253; 5,571,799; 5,587,361; 5,194,599; 5,565,555; 5,527,899; 5,721,218; 5,672,697 and 5,625,050, certain of which are commonly owned with this application, and each of which is herein incorporated by reference.

Preferred modified oligonucleotide backbones that do not include a phosphorus atom therein have backbones that are formed by short chain alkyl or cycloalkyl internucleoside linkages, mixed heteroatom and alkyl or cycloalkyl internucleoside linkages, or one or more short chain heteroatomic or heterocyclic internucleoside linkages. These include those having morpholino linkages (formed in part from the sugar portion of a nucleoside); siloxane backbones; sulfide, sulfoxide and sulfone backbones; formacetyl and thioformacetyl backbones; methylene formacetyl and thioformacetyl backbones; riboacetyl backbones; alkene containing backbones; sulfamate backbones; methyleneimino and methylenehydrazino backbones; sulfonate and sulfonamide backbones; amide backbones; and others having mixed N, O, S and $CH_2$ component parts.

Representative United States patents that teach the preparation of the above oligonucleosides include, but are not limited to, U.S. Pat. Nos.: 5,034,506; 5,166,315; 5,185,444; 5,214,134; 5,216,141; 5,235,033; 5,264,562; 5,264,564; 5,405,938; 5,434,257; 5,466,677; 5,470,967; 5,489,677; 5,541,307; 5,561,225; 5,596,086; 5,602,240; 5,610,289; 5,602,240; 5,608,046; 5,610,289; 5,618,704; 5,623,070; 5,663,312; 5,633,360; 5,677,437; 5,792,608; 5,646,269 and 5,677,439, certain of which are commonly owned with this application, and each of which is herein incorporated by reference.

In other preferred oligonucleotide mimetics, both the sugar and the internucleoside linkage, i.e., the backbone, of the nucleotide units are replaced with novel groups. The base units are maintained for hybridization with an appropriate nucleic acid target compound. One such oligomeric compound, an oligonucleotide mimetic that has been shown to have excellent hybridization properties, is referred to as a peptide nucleic acid (PNA). In PNA compounds, the sugar-backbone of an oligonucleotide is replaced with an amide containing backbone, in particular an aminoethylglycine backbone. The nucleobases are retained and are bound directly or indirectly to aza nitrogen atoms of the amide portion of the backbone. Representative United States patents that teach the preparation of PNA compounds include, but are not limited to, U.S. Pat. Nos.: 5,539,082; 5,714,331; and 5,719,262, each of which is herein incorporated by reference. Further teaching of PNA compounds can be found in Nielsen et al., *Science*, 1991, 254, 1497–1500.

Most preferred embodiments of the invention are oligonucleotides with phosphorothioates backbones and oligonucleosides with heteroatom backbones, and in particular —$CH_2$—NH—O—$CH_2$—, —$CH_2$—N($CH_3$)—O—$CH_2$— [known as a methylene (methylimino) or MMI backbone], —$CH_2$—O—N($CH_3$)—$CH_2$—, —$CH_2$— N($CH_3$)—N($CH_3$)—$CH_2$— and —O—N($CH_3$)—$CH_2$—$CH_2$— [wherein the native phosphodiester backbone is represented as —O—P—O—$CH_2$—] of the above referenced U.S. Pat. No. 5,489,677, and the amide backbones of the above referenced U.S. Pat. No. 5,602,240. Also preferred are oligonucleotides having morpholino backbone structures of the above-referenced U.S. Pat. No. 5,034,506.

Modified oligonucleotides may also contain one or more substituted sugar moieties. Preferred oligonucleotides comprise one of the following at the 2' position: OH; F; O—, S—, or N-alkyl; O—, S—, or N-alkenyl; O—, S— or N-alkynyl; or O-alkyl-O-alkyl, wherein the alkyl, alkenyl and alkynyl may be substituted or unsubstituted $C_1$ to $C_{10}$ alkyl or $C_2$ to $C_{10}$ alkenyl and alkynyl. Particularly preferred are $O[(CH_2)_nO]_mCH_3$, $O(CH_2)_nOCH_3$, $O(CH_2)_nNH_2$, $O(CH_2)_nCH_3$, $O(CH_2)_nONH_2$, and $O(CH_2)_nON[(CH_2)_nCH_3)]_2$, where n and m are from 1 to about 10. Other preferred oligonucleotides comprise one of the following at the 2' position: $C_1$ to $C_{10}$ lower alkyl, substituted lower alkyl, alkenyl, alkynyl, alkaryl, aralkyl, O-alkaryl or O-aralkyl, SH, $SCH_3$, OCN, Cl, Br, CN, $CF_3$, $OCF_3$, $SOCH_3$, $SO_2CH_3$, $ONO_2$, $NO_2$, $N_3$, $NH_2$, heterocycloalkyl, heterocycloalkaryl, aminoalkylamino, poly-alkylamino, substituted silyl, an RNA cleaving group, a reporter group, an intercalator, a group for improving the pharmacokinetic properties of an oligonucleotide, or a group for improving the pharmacodynamic properties of an oligonucleotide, and other substituents having similar properties. A preferred modification includes 2'-methoxyethoxy (2'-O—$CH_2CH_2OCH_3$, also known as 2'-O-(2-methoxyethyl) or 2'-MOE) (Martin et al., *Helv. Chim. Acta*, 1995, 78, 486–504) i.e., an alkoxyalkoxy group. A further preferred modification includes 2'-dimethylaminooxyethoxy, i.e., a $O(CH_2)_2ON(CH_3)_2$ group, also known as 2'-DMAOE, as described in examples hereinbelow, and 2'-dimethylamino-ethoxyethoxy (also known in the art as 2'-O-dimethylamino-ethoxyethyl or 2'-DMAEOE), i.e., 2'-O—$CH_2$—O—$CH_2$—N($CH_2$)$_2$, also described in examples hereinbelow.

A further prefered modification includes Locked Nucleic Acids (LNAs) in which the 2'-hydroxyl group is linked to the 3' or 4' carbon atom of the sugar ring thereby forming a bicyclic sugar moiety. The linkage is preferably a methelyne (—$CH_2$—)$_n$ group bridging the 2' oxygen atom and the 4' carbon atom wherein n is 1 or 2. LNAs and preparation thereof are described in WO 98/39352 and WO 99/14226.

Other preferred modifications include 2'-methoxy (2'-O—$CH_3$), 2'-aminopropoxy (2'-O$CH_2CH_2CH_2NH_2$), 2'-allyl (2'-$CH_2$—CH=$CH_2$), 2'-O-allyl (2'-O—$CH_2$—CH=$CH_2$) and 2'-fluoro (2'-F). The 2'-modification may be in the arabino (up) position or ribo (down) position. A preferred 2'-arabino modification is 2'-F. Similar modifications may also be made at other positions on the oligonucleotide, particularly the 3' position of the sugar on the 3' terminal nucleotide or in 2'-5' linked oligonucleotides and the 5' position of 5' terminal nucleotide. Oligonucleotides may also have sugar mimetics such as cyclobutyl moieties in place of the pentofuranosyl sugar. Representative United States patents that teach the preparation of such modified sugar structures include, but are not limited to, U.S. Pat. Nos.: 4,981,957; 5,118,800; 5,319,080; 5,359,044; 5,393,878; 5,446,137; 5,466,786; 5,514,785; 5,519,134; 5,567,811; 5,576,427; 5,591,722; 5,597,909; 5,610,300; 5,627,053; 5,639,873; 5,646,265; 5,658,873; 5,670,633; 5,792,747; and 5,700,920, certain of which are commonly owned with the instant application, and each of which is herein incorporated by reference in its entirety.

Oligonucleotides may also include nucleobase (often referred to in the art simply as "base") modifications or substitutions. As used herein, "unmodified" or "natural" nucleobases include the purine bases adenine (A) and guanine (G), and the pyrimidine bases thymine (T), cytosine (C) and uracil (U). Modified nucleobases include other synthetic and natural nucleobases such as 5-methylcytosine (5-me-C), 5-hydroxymethyl cytosine, xanthine, hypoxanthine, 2-aminoadenine, 6-methyl and other alkyl derivatives of adenine and guanine, 2-propyl and other alkyl derivatives of adenine and guanine, 2-thiouracil, 2-thiothymine and 2-thiocytosine, 5-halouracil and cytosine, 5-propynyl (—C≡C—CH$_3$) uracil and cytosine and other alkynyl derivatives of pyrimidine bases, 6-azo uracil, cytosine and thymine, 5-uracil (pseudouracil), 4-thiouracil, 8-halo, 8-amino, 8-thiol, 8-thioalkyl, 8-hydroxyl and other 8-substituted adenines and guanines, 5-halo particularly 5-bromo, 5-trifluoromethyl and other 5-substituted uracils and cytosines, 7-methylguanine and 7-methyladenine, 2-F-adenine, 2-amino-adenine, 8-azaguanine and 8-azaadenine, 7-deazaguanine and 7-deazaadenine and 3-deazaguanine and 3-deazaadenine. Further modified nucleobases include tricyclic pyrimidines such as phenoxazine cytidine(1H-pyrimido[5,4-b][1,4]benzoxazin-2(3H)-one), phenothiazine cytidine (1H-pyrimido[5,4-b] [1,4]benzothiazin-2(3H)-one), G-clamps such as a substituted phenoxazine cytidine (e.g. 9-(2-aminoethoxy)-H-pyrimido[5,4-b] [1,4] benzoxazin-2(3H)-one), carbazole cytidine (2H-pyrimido[4,5-b]indol-2-one), pyridoindole cytidine (H-pyrido[3',2':4,5] pyrrolo[2,3-d]pyrimiclin-2-one). Modified nucleobases may also include those in which the purine or pyrimidine base is replaced with other heterocycles, for example 7-deaza-adenine, 7-deazaguanosine, 2-aminopyridine and 2-pyridone. Further nucleobases include those disclosed in U.S. Pat. No. 3,687,808, those disclosed in *The Concise Encyclopedia Of Polymer Science And Engineering*, pages 858–859, Kroschwitz, J. I., ed. John Wiley & Sons, 1990, those disclosed by Englisch et al., *Angewandte Chemie*, International Edition, 1991, 30, 613, and those disclosed by Sanghvi, Y. S., Chapter 15, *Antisense Research and Applications*, pages 289–302, Crooke, S. T. and Lebleu, B. ed., CRC Press, 1993. Certain of these nucleobases are particularly useful for increasing the binding affinity of the oligomeric compounds of the invention. These include 5-substituted pyrimidines, 6-azapyrimidines and N-2, N-6 and O-6 substituted purines, including 2-aminopropyladenine, 5-propynyluracil and 5-propynylcytosine. 5-methylcytosine substitutions have been shown to increase nucleic acid duplex stability by 0.6–1.2° C. (Sanghvi, Y. S., Crooke, S. T. and Lebleu, B., eds., *Antisense Research and Applications*, CRC Press, Boca Raton, 1993, pp. 276–278) and are presently preferred base substitutions, even more particularly when combined with 2'-O-methoxyethyl sugar modifications.

Representative United States patents that teach the preparation of certain of the above noted modified nucleobases as well as other modified nucleobases include, but are not limited to, the above noted U.S. Pat. No. 3,687,808, as well as U.S. Pat. Nos.: 4,845,205; 5,130,302; 5,134,066; 5,175,273; 5,367,066; 5,432,272; 5,457,187; 5,459,255; 5,484,908; 5,502,177; 5,525,711; 5,552,540; 5,587,469; 5,594,121, 5,596,091; 5,614,617; 5,645,985; 5,830,653; 5,763,588; 6,005,096; and 5,681,941, certain of which are commonly owned with the instant application, and each of which is herein incorporated by reference, and U.S. Pat. No. 5,750,692, which is commonly owned with the instant application and also herein incorporated by reference.

Another modification of the oligonucleotides of the invention involves chemically linking to the oligonucleotide one or more moieties or conjugates which enhance the activity, cellular distribution or cellular uptake of the oligonucleotide. The compounds of the invention can include conjugate groups covalently bound to functional groups such as primary or secondary hydroxyl groups. Conjugate groups of the invention include intercalators, reporter molecules, polyamines, polyamides, polyethylene glycols, polyethers, groups that enhance the pharmacodynamic properties of oligomers, and groups that enhance the pharmacokinetic properties of oligomers. Typical conjugates groups include cholesterols, lipids, phospholipids, biotin, phenazine, folate, phenanthridine, anthraquinone, acridine, fluoresceins, rhodamines, coumarins, and dyes. Groups that enhance the pharmacodynamic properties, in the context of this invention, include groups that improve oligomer uptake, enhance oligomer resistance to degradation, and/or strengthen sequence-specific hybridization with RNA. Groups that enhance the pharmacokinetic properties, in the context of this invention, include groups that improve oligomer uptake, distribution, metabolism or excretion. Representative conjugate groups are disclosed in International Patent Application PCT/US92/09196, filed Oct. 23, 1992 the entire disclosure of which is incorporated herein by reference. Conjugate moieties include but are not limited to lipid moieties such as a cholesterol moiety (Letsinger et al., *Proc. Natl. Acad. Sci. USA*, 1989, 86, 6553–6556), cholic acid (Manoharan et al., *Bioorg. Med. Chem. Let.*, 1994, 4, 1053–1060), a thioether, e.g., hexyl-S-tritylthiol (Manoharan et al., *Ann. N.Y. Acad. Sci.*, 1992, 660, 306–309; Manoharan et al., *Bioorg. Med. Chem. Let.*, 1993, 3, 2765–2770), a thiocholesterol (Oberhauser et al., *Nucl. Acids Res.*, 1992, 20, 533–538), an aliphatic chain, e.g., dodecandiol or undecyl residues (Saison-Behmoaras et al., *EMBO J.*, 1991, 10, 1111–1118; Kabanov et al., *FEBS Lett.*, 1990, 259, 327–330; Svinarchuk et al., *Biochimie*, 1993, 75, 49–54), a phospholipid, e.g., di-hexadecyl-rac-glycerol or triethyl-ammonium 1,2-di-O-hexadecyl-rac-glycero-3-H-phosphonate (Manoharan et al., *Tetrahedron Lett.*, 1995, 36, 3651–3654; Shea et al., *Nucl. Acids Res.*, 1990, 18, 3777–3783), a polyamine or a polyethylene glycol chain (Manoharan et al., *Nucleosides & Nucleotides*, 1995, 14, 969–973), or adamantane acetic acid (Manoharan et al., *Tetrahedron Lett.*, 1995, 36, 3651–3654), a palmityl moiety (Mishra et al., *Biochim. Biophys. Acta*, 1995, 1264, 229–237), or an octadecylamine or hexylamino-carbonyl-oxycholesterol moiety (Crooke et al., *J. Pharmacol. Exp. Ther.*, 1996, 277, 923–937. Oligonucleotides of the invention may also be conjugated to active drug substances, for example, aspirin, warfarin, phenylbutazone, ibuprofen, suprofen, fenbufen, ketoprofen, (S)-(+)-pranoprofen, carprofen, dansylsarcosine, 2,3,5-triiodobenzoic acid, flufenamic acid, folinic acid, a benzothiadiazide, chlorothiazide, a diazepine, indomethicin, a barbiturate, a cephalosporin, a sulfa drug, an antidiabetic, an antibacterial or an antibiotic. Oligonucleotide-drug conjugates and their preparation are described in U.S. patent application Ser. No. 09/334,130 (filed Jun. 15, 1999) which is incorporated herein by reference in its entirety.

Representative United States patents that teach the preparation of such oligonucleotide conjugates include, but are not limited to, U.S. Pat. Nos.: 4,828,979; 4,948,882; 5,218,105; 5,525,465; 5,541,313; 5,545,730; 5,552,538; 5,578,717, 5,580,731; 5,580,731; 5,591,584; 5,109,124; 5,118,802; 5,138,045; 5,414,077; 5,486,603; 5,512,439; 5,578,718; 5,608,046; 4,587,044; 4,605,735; 4,667,025; 4,762,779; 4,789,737; 4,824,941; 4,835,263; 4,876,335; 4,904,582; 4,958,013; 5,082,830; 5,112,963; 5,214,136; 5,082,830; 5,112,963; 5,214,136; 5,245,022; 5,254,469; 5,258,506; 5,262,536; 5,272,250; 5,292,873; 5,317,098; 5,371,241, 5,391,723; 5,416,203, 5,451,463; 5,510,475; 5,512,667; 5,514,785; 5,565,552; 5,567,810; 5,574,142; 5,585,481; 5,587,371; 5,595,726; 5,597,696; 5,599,923; 5,599,928 and 5,688,941, certain of which are commonly owned with the instant application, and each of which is herein incorporated by reference.

It is not necessary for all positions in a given compound to be uniformly modified, and in fact more than one of the aforementioned modifications may be incorporated in a single compound or even at a single nucleoside within an oligonucleotide. The present invention also includes antisense compounds which are chimeric compounds. "Chimeric" antisense compounds or "chimeras," in the context of this invention, are antisense compounds, particularly oligonucleotides, which contain two or more chemically distinct regions, each made up of at least one monomer unit, i.e., a nucleotide in the case of an oligonucleotide compound. These oligonucleotides typically contain at least one region wherein the oligonucleotide is modified so as to confer upon the oligonucleotide increased resistance to nuclease degradation, increased cellular uptake, and/or increased binding affinity for the target nucleic acid. An additional region of the oligonucleotide may serve as a substrate for enzymes capable of cleaving RNA:DNA or RNA:RNA hybrids. By way of example, RNase H is a cellular endonuclease which cleaves the RNA strand of an RNA:DNA duplex. Activation of RNase H, therefore, results in cleavage of the RNA target, thereby greatly enhancing the efficiency of oligonucleotide inhibition of gene expression. Consequently, comparable results can often be obtained with shorter oligonucleotides when chimeric oligonucleotides are used, compared to phosphorothioate deoxyoligonucleotides hybridizing to the same target region. Cleavage of the RNA target can be routinely detected by gel electrophoresis and, if necessary, associated nucleic acid hybridization techniques known in the art.

Chimeric antisense compounds of the invention may be formed as composite structures of two or more oligonucleotides, modified oligonucleotides, oligonucleosides and/or oligonucleotide mimetics as described above. Such compounds have also been referred to in the art as hybrids or gapmers. Representative United States patents that teach the preparation of such hybrid structures include, but are not limited to, U.S. Pat. Nos.: 5,013,830; 5,149,797; 5,220,007; 5,256,775; 5,366,878; 5,403,711; 5,491,133; 5,565,350; 5,623,065; 5,652,355; 5,652,356; and 5,700,922, certain of which are commonly owned with the instant application, and each of which is herein incorporated by reference in its entirety.

The antisense compounds used in accordance with this invention may be conveniently and routinely made through the well-known technique of solid phase synthesis. Equipment for such synthesis is sold by several vendors including, for example, Applied Biosystems (Foster City, Calif.). Any other means for such synthesis known in the art may additionally or alternatively be employed. It is well known to use similar techniques to prepare oligonucleotides such as the phosphorothioates and alkylated derivatives.

The antisense compounds of the invention are synthesized in vitro and do not include antisense compositions of biological origin, or genetic vector constructs designed to direct the in vivo synthesis of antisense molecules. The compounds of the invention may also be admixed, encapsulated, conjugated or otherwise associated with other molecules, molecule structures or mixtures of compounds, as for example, liposomes, receptor targeted molecules, oral, rectal, topical or other formulations, for assisting in uptake, distribution and/or absorption. Representative United States patents that teach the preparation of such uptake, distribution and/or absorption assisting formulations include, but are not limited to, U.S. Pat. Nos.: 5,108,921; 5,354,844; 5,416,016; 5,459, 127; 5,521,291; 5,543,158; 5,547,932; 5,583,020; 5,591, 721; 4,426,330; 4,534,899; 5,013,556; 5,108,921; 5,213, 804; 5,227,170; 5,264,221; 5,356,633; 5,395,619; 5,416, 016; 5,417,978; 5,462,854; 5,469,854; 5,512,295; 5,527, 528; 5,534,259; 5,543,152; 5,556,948; 5,580,575; and 5,595,756, each of which is herein incorporated by reference.

The antisense compounds of the invention encompass any pharmaceutically acceptable salts, esters, or salts of such esters, or any other compound which, upon administration to an animal including a human, is capable of providing (directly or indirectly) the biologically active metabolite or residue thereof. Accordingly, for example, the disclosure is also drawn to prodrugs and pharmaceutically acceptable salts of the compounds of the invention, pharmaceutically acceptable salts of such prodrugs, and other bioequivalents.

The term "prodrug" indicates a therapeutic agent that is prepared in an inactive form that is converted to an active form (i.e., drug) within the body or cells thereof by the action of endogenous enzymes or other chemicals and/or conditions. In particular, prodrug versions of the oligonucleotides of the invention are prepared as SATE [(S-acetyl-2-thioethyl) phosphate] derivatives according to the methods disclosed in WO 93/24510 to Gosselin et al., published Dec. 9, 1993 or in WO 94/26764 and U.S. Pat. No. 5,770,713 to Imbach et al.

The term "pharmaceutically acceptable salts" refers to physiologically and pharmaceutically acceptable salts of the compounds of the invention: i.e., salts that retain the desired biological activity of the parent compound and do not impart undesired toxicological effects thereto.

Pharmaceutically acceptable base addition salts are formed with metals or amines, such as alkali and alkaline earth metals or organic amines. Examples of metals used as cations are sodium, potassium, magnesium, calcium, and the like. Examples of suitable amines are N,N'-dibenzylethylenediamine, chloroprocaine, choline, diethanolamine, dicyclohexylamine, ethylenediamine, N-methylglucamine, and procaine (see, for example, Berge et al., "Pharmaceutical Salts," J. of Pharma Sci., 1977, 66, 1–19). The base addition salts of said acidic compounds are prepared by contacting the free acid form with a sufficient amount of the desired base to produce the salt in the conventional manner. The free acid form may be regenerated by contacting the salt form with an acid and isolating the free acid in the conventional manner. The free acid forms differ from their respective salt forms somewhat in certain physical properties such as solubility in polar solvents, but otherwise the salts are equivalent to their respective free acid for purposes of the present invention. As used herein, a "pharmaceutical addition salt" includes a pharmaceutically acceptable salt of an acid form of one of the components of the compositions of the invention. These include organic or inorganic acid salts of the amines. Preferred acid salts are the hydrochlorides, acetates, salicylates, nitrates and phosphates. Other suitable pharmaceutically acceptable salts are well known to those skilled in the art and include basic salts of a variety of inorganic and organic acids, such as, for example, with inorganic acids, such as for example hydrochloric acid, hydrobromic acid, sulfuric acid or phosphoric acid; with organic carboxylic, sulfonic, sulfo or phospho acids or N-substituted sulfaric acids, for example acetic acid, propionic acid, glycolic acid, succinic acid, maleic acid, hydroxymaleic acid, methylmaleic acid, fumaric acid, malic acid, tartaric acid, lactic acid, oxalic acid, gluconic acid, glucaric acid, glucuronic acid, citric acid, benzoic acid, cinnamic acid, mandelic acid, salicylic acid, 4-aminosalicylic acid, 2-phenoxybenzoic acid, 2-acetoxybenzoic acid, embonic acid, nicotinic acid or isonicotinic acid; and with amino acids, such as the 20 alpha-amino acids involved in the synthesis of proteins in nature, for example glutamic acid or aspartic acid, and also with phenylacetic acid, methanesulfonic acid, ethanesulfonic acid, 2-hydroxyethanesulfonic acid, ethane-1,2-disulfonic acid, benzenesulfonic acid, 4-methylbenzenesulfonic acid, naphthalene-2-sulfonic acid, naphthalene-1,5-disulfonic acid, 2- or 3-phosphoglycerate, glucose-6-phosphate, N-cyclohexylsulfamic acid (with the formation of cyclamates), or with other acid organic compounds, such as ascorbic acid. Pharmaceutically acceptable salts of compounds may also be prepared with a pharmaceutically acceptable cation. Suitable pharmaceutically acceptable cations are well known to those skilled in the art and include alkaline, alkaline earth, ammonium and quaternary ammonium cations. Carbonates or hydrogen carbonates are also possible.

For oligonucleotides, preferred examples of pharmaceutically acceptable salts include but are not limited to (a) salts formed with cations such as sodium, potassium, ammonium, magnesium, calcium, polyamines such as spermine and spermidine, etc.; (b) acid addition salts formed with inorganic acids, for example hydrochloric acid, hydrobromic acid, sulfuric acid, phosphoric acid, nitric acid and the like; (c) salts formed with organic acids such as, for example, acetic acid, oxalic acid, tartaric acid, succinic acid, maleic acid, fumaric acid, gluconic acid, citric acid, malic acid, ascorbic acid, benzoic acid, tannic acid, palmitic acid, alginic acid, polyglutamic acid, naphthalenesulfonic acid, methanesulfonic acid, p-toluenesulfonic acid, naphthalene-disulfonic acid, polygalacturonic acid, and the like; and (d) salts formed from elemental anions such as chlorine, bromine, and iodine.

The antisense compounds of the present invention can be utilized for diagnostics, therapeutics, prophylaxis and as research reagents and kits. For therapeutics, an animal, preferably a human, suspected of having a disease or disorder which can be treated by modulating the expression of CD36L1 is treated by administering antisense compounds in accordance with this invention. The compounds of the invention can be utilized in pharmaceutical compositions by adding an effective amount of an antisense compound to a suitable pharmaceutically acceptable diluent or carrier. Use of the antisense compounds and methods of the invention may also be useful prophylactically, e.g., to prevent or delay infection, inflammation or tumor formation, for example.

The antisense compounds of the invention are useful for research and diagnostics, because these compounds hybridize to nucleic acids encoding CD36L1, enabling sandwich and other assays to easily be constructed to exploit this fact. Hybridization of the antisense oligonucleotides of the invention with a nucleic acid encoding CD36L1 can be detected by means known in the art. Such means may include conjugation of an enzyme to the oligonucleotide, radiolabelling of the oligonucleotide or any other suitable detection means. Kits using such detection means for detecting the level of CD36L1 in a sample may also be prepared.

The present invention also includes pharmaceutical compositions and formulations which include the antisense compounds of the invention. The pharmaceutical compositions of the present invention may be administered in a number of ways depending upon whether local or systemic treatment is desired and upon the area to be treated. Administration may be topical (including ophthalmic and to mucous membranes including vaginal and rectal delivery), pulmonary, e.g., by inhalation or insufflation of powders or aerosols, including by nebulizer; intratracheal, intranasal, epidermal and transdermal), oral or parenteral. Parenteral administration includes intravenous, intraarterial, subcutaneous, intraperitoneal or intramuscular injection or infusion; or intracranial, e.g., intrathecal or intraventricular, administration. Oligonucleotides with at least one 2'-O-methoxyethyl modification are believed to be particularly useful for oral administration.

Pharmaceutical compositions and formulations for topical administration may include transdermal patches, ointments, lotions, creams, gels, drops, suppositories, sprays, liquids and powders. Conventional pharmaceutical carriers, aqueous, powder or oily bases, thickeners and the like may be necessary or desirable. Coated condoms, gloves and the like may also be useful. Preferred topical formulations include those in which the oligonucleotides of the invention are in admixture with a topical delivery agent such as lipids, liposomes, fatty acids, fatty acid esters, steroids, chelating agents and surfactants. Preferred lipids and liposomes include neutral (e.g. dioleoylphosphatidyl DOPE ethanolamine, dimyristoylphosphatidyl choline DMPC, distearolyphosphatidyl choline) negative (e.g. dimyristoylphosphatidyl glycerol DMPG) and cationic (e.g. dioleoyltetramethylaminopropyl DOTAP and dioleoylphosphatidyl ethanolamine DOTMA). Oligonucleotides of the invention may be encapsulated within liposomes or may form complexes thereto, in particular to cationic liposomes. Alternatively, oligonucleotides may be complexed to lipids, in particular to cationic lipids. Preferred fatty acids and esters include but are not limited arachidonic acid, oleic acid, eicosanoic acid, lauric acid, caprylic acid, capric acid, myristic acid, palmitic acid, stearic acid, linoleic acid, linolenic acid, dicaprate, tricaprate, monoolein, dilaurin, glyceryl 1-monocaprate, 1-dodecylazacycloheptan-2-one, an acylcarnitine, an acylcholine, or a $C_{1-10}$ alkyl ester (e.g. isopropylmyristate IPM), monoglyceride, diglyceride or pharmaceutically acceptable salt thereof. Topical formulations are described in detail in U.S. patent application Ser. No. 09/315,298 filed on May 20, 1999 which is incorporated herein by reference in its entirety.

Compositions and formulations for oral administration include powders or granules, microparticulates, nanoparticulates, suspensions or solutions in water or non-aqueous media, capsules, gel capsules, sachets, tablets or minitablets. Thickeners, flavoring agents, diluents, emulsifiers, dispersing aids or binders may be desirable. Preferred oral formulations are those in which oligonucleotides of the invention are administered in conjunction with one or more penetration enhancers surfactants and chelators. Preferred surfactants include fatty acids and/or esters or salts thereof, bile acids and/or salts thereof. Prefered bile acids/salts include chenodeoxycholic acid (CDCA) and ursodeoxychenodeoxycholic acid (UDCA), cholic acid, dehydrocholic acid, deoxycholic acid, glucholic acid, glycholic acid, glycodeoxycholic acid, taurocholic acid, taurodeoxycholic acid, sodium tauro-24,25-dihydro-fusidate, sodium glycodihydrofusidate. Prefered fatty acids include arachidonic acid, undecanoic acid, oleic acid, lauric acid, caprylic acid, capric acid, myristic acid, palmitic acid, stearic acid, linoleic acid, linolenic acid, dicaprate, tricaprate, monoolein, dilaurin, glyceryl 1-monocaprate, 1-dodecylazacycloheptan-2-one, an acylcarnitine, an acylcholine, or a monoglyceride, a diglyceride or a pharmaceutically acceptable salt thereof (e.g. sodium). Also prefered are combinations of penetration enhancers, for example, fatty acids/salts in combination with bile acids/salts. A particularly prefered combination is the sodium salt of lauric acid, capric acid and UDCA. Further penetration enhancers include polyoxyethylene-9-lauryl ether, polyoxyethylene-20-cetyl ether. oligonucleotides of the invention may be delivered orally in granular form including sprayed dried particles, or complexed to form micro or nanoparticles. Oligonucleotide complexing agents include poly-amino acids; polyimines; polyacrylates; polyalkylacrylates, polyoxethanes, polyalkylcyanoacrylates; cationized gelatins, albumins, starches, acrylates, polyethyleneglycols (PEG) and starches; polyalkylcyanoacrylates; DEAE-derivatized polyimines, pollulans, celluloses and starches. Particularly preferred complexing agents include chitosan, N-trimethylchitosan, poly-L-lysine, polyhistidine, polyornithine, polyspermines, protamine, polyvinylpyridine, polythiodiethylamino-methylethylene P(TDAE), polyaminostyrene (e.g. p-amino), poly(methylcyanoacrylate), poly(ethylcyanoacrylate), poly(butylcyanoacrylate), poly(isobutylcyanoacrylate), poly(isohexylcynaoacrylate), DEAE-methacrylate, DEAE-hexylacrylate, DEAE-acrylamide, DEAE-albumin and DEAE-dextran, polymethylacrylate, polyhexylacrylate, poly(D,L-lactic acid), poly(DL-lactic-co-glycolic acid (PLGA), alginate, and polyethyleneglycol (PEG). Oral formulations for oligonucleotides and their preparation are described in detail in U.S. applications Ser. Nos. 08/886,829 (filed Jul. 1, 1997), 09/108,673 (filed Jul. 1, 1998), 09/256, 515 (filed Feb. 23, 1999), 09/082,624 (filed May 21, 1998) and 09/315,298 (filed May 20, 1999) each of which is incorporated herein by reference in their entirety.

Compositions and formulations for parenteral, intrathecal or intraventricular administration may include sterile aqueous solutions which may also contain buffers, diluents and other suitable additives such as, but not limited to, penetration enhancers, carrier compounds and other pharmaceutically acceptable carriers or excipients.

Pharmaceutical compositions of the present invention include, but are not limited to, solutions, emulsions, and liposome-containing formulations. These compositions may be generated from a variety of components that include, but are not limited to, preformed liquids, self-emulsifying solids and self-emulsifying semisolids.

The pharmaceutical formulations of the present invention, which may conveniently be presented in unit dosage form, may be prepared according to conventional techniques well known in the pharmaceutical industry. Such techniques include the step of bringing into association the active ingredients with the pharmaceutical carrier(s) or excipient (s). In general the formulations are prepared by uniformly and intimately bringing into association the active ingredients with liquid carriers or finely divided solid carriers or both, and then, if necessary, shaping the product.

The compositions of the present invention may be formulated into any of many possible dosage forms such as, but not limited to, tablets, capsules, gel capsules, liquid syrups, soft gels, suppositories, and enemas. The compositions of the present invention may also be formulated as suspensions in aqueous, non-aqueous or mixed media. Aqueous suspensions may further contain substances which increase the viscosity of the suspension including, for example, sodium carboxymethylcellulose, sorbitol and/or dextran. The suspension may also contain stabilizers.

In one embodiment of the present invention the pharmaceutical compositions may be formulated and used as foams. Pharmaceutical foams include formulations such as, but not limited to, emulsions, microenulsions, creams, jellies and liposomes. While basically similar in nature these formulations vary in the components and the consistency of the final product. The preparation of such compositions and formulations is generally known to those skilled in the pharmaceutical and formulation arts and may be applied to the formulation of the compositions of the present invention.

Emulsions

The compositions of the present invention may be prepared and formulated as emulsions. Emulsions are typically heterogenous systems of one liquid dispersed in another in the form of droplets usually exceeding 0.1 μm in diameter. (Idson, in *Pharmaceutical Dosage Forms*, Lieberman, Rieger and Banker (Eds.), 1988, Marcel Dekker, Inc., New York, N.Y., volume 1, p. 199; Rosoff, in *Pharmaceutical Dosage Forms*, Lieberman, Rieger and Banker (Eds.), 1988, Marcel Dekker, Inc., New York, N.Y., Volume 1, p. 245; Block in *Pharmaceutical Dosage Forms*, Lieberman, Rieger and Banker (Eds.), 1988, Marcel Dekker, Inc., New York, N.Y., volume 2, p. 335; Higuchi et al., in *Remington's Pharmaceutical Sciences*, Mack Publishing Co., Easton, Pa., 1985, p. 301). Emulsions are often biphasic systems comprising of two immiscible liquid phases intimately mixed and dispersed with each other. In general, emulsions may be either water-in-oil (w/o) or of the oil-in-water (o/w) variety. When an aqueous phase is finely divided into and dispersed as minute droplets into a bulk oily phase the resulting composition is called a water-in-oil (w/o) emulsion. Alternatively, when an oily phase is finely divided into and dispersed as minute droplets into a bulk aqueous phase the resulting composition is called an oil-in-water (o/w) emulsion. Emulsions may contain additional components in addition to the dispersed phases and the active drug which may be present as a solution in either the aqueous phase, oily phase or itself as a separate phase. Pharmaceutical excipients such as emulsifiers, stabilizers, dyes, and anti-oxidants may also be present in emulsions as needed. Pharmaceutical emulsions may also be multiple emulsions that are comprised of more than two phases such as, for example, in the case of oil-in-water-in-oil (o/w/o) and water-in-oil-in-water (w/o/w) emulsions. Such complex formulations often provide certain advantages that simple binary emulsions do not. Multiple emulsions in which individual oil droplets of an o/w emulsion enclose small water droplets constitute a w/o/w emulsion. Likewise a system of oil droplets enclosed in globules of water stabilized in an oily continuous provides an o/w/o emulsion.

Emulsions are characterized by little or no thermodynamic stability. Often, the dispersed or discontinuous phase of the emulsion is well dispersed into the external or continuous phase and maintained in this form through the means of emulsifiers or the viscosity of the formulation. Either of the phases of the emulsion may be a semisolid or a solid, as is the case of emulsion-style ointment bases and creams. Other means of stabilizing emulsions entail the use of emulsifiers that may be incorporated into either phase of the emulsion. Emulsifiers may broadly be classified into four categories: synthetic surfactants, naturally occurring emulsifiers, absorption bases, and finely dispersed solids (Idson, in *Pharmaceutical Dosage Forms*, Lieberman, Rieger and Banker (Eds.), 1988, Marcel Dekker, Inc., New York, N.Y., volume 1, p. 199).

Synthetic surfactants, also known as surface active agents, have found wide applicability in the formulation of emulsions and have been reviewed in the literature (Rieger, in *Pharmaceutical Dosage Forms*, Lieberman, Rieger and Banker (Eds.), 1988, Marcel Dekker, Inc., New York, N.Y., volume 1, p. 285; Idson, in *Pharmaceutical Dosage Forms*, Lieberman, Rieger and Banker (Eds.), Marcel Dekker, Inc., New York, N.Y., 1988, volume 1, p. 199). Surfactants are typically amphiphilic and comprise a hydrophilic and a hydrophobic portion. The ratio of the hydrophilic to the hydrophobic nature of the surfactant has been termed the hydrophile/lipophile balance (HLB) and is a valuable tool in categorizing and selecting surfactants, in the preparation of formulations. Surfactants may be classified into different classes based on the nature of the hydrophilic group: nonionic, anionic, cationic and amphoteric (Rieger, in *Pharmaceutical Dosage Forms*, Lieberman, Rieger and Banker (Eds.), 1988, Marcel Dekker, Inc., New York, N.Y., volume 1, p. 285).

Naturally occurring emulsifiers used in emulsion formulations include lanolin, beeswax, phosphatides, lecithin and acacia. Absorption bases possess hydrophilic properties such that they can soak up water to form w/o emulsions yet retain their semisolid consistencies, such as anhydrous lanolin and hydrophilic petrolatum. Finely divided solids have also been used as good emulsifiers especially in combination with surfactants and in viscous preparations. These include polar inorganic solids, such as heavy metal hydroxides, nonswelling clays such as bentonite, attapulgite, hectorite, kaolin, montmorillonite, colloidal aluminum silicate and colloidal magnesium aluminum silicate, pigments and nonpolar solids such as carbon or glyceryl tristearate.

A large variety of non-emulsifying materials are also included in emulsion formulations and contribute to the properties of emulsions. These include fats, oils, waxes, fatty acids, fatty alcohols, fatty esters, humectants, hydrophilic colloids, preservatives and antioxidants (Block, in *Pharmaceutical Dosage Forms*, Lieberman, Rieger and Banker (Eds.), 1988, Marcel Dekker, Inc., New York, N.Y., volume 1, p. 335; Idson, in *Pharmaceutical Dosage Forms*, Lieberman, Rieger and Banker (Eds.), 1988, Marcel Dekker, Inc., New York, N.Y., volume 1, p. 199).

Hydrophilic colloids or hydrocolloids include naturally occurring gums and synthetic polymers such as polysaccharides (for example, acacia, agar, alginic acid, carrageenan, guar gum, karaya gum, and tragacanth), cellulose derivatives (for example, carboxymethylcellulose and carboxypropylcellulose), and synthetic polymers (for example, carbomers, cellulose ethers, and carboxyvinyl polymers). These disperse or swell in water to form colloidal solutions that stabilize emulsions by forming strong interfacial films around the dispersed-phase droplets and by increasing the viscosity of the external phase.

Since emulsions often contain a number of ingredients such as carbohydrates, proteins, sterols and phosphatides that may readily support the growth of microbes, these formulations often incorporate preservatives. Commonly used preservatives included in emulsion formulations include methyl paraben, propyl paraben, quaternary ammonium salts, benzalkonium chloride, esters of p-hydroxybenzoic acid, and boric acid. Antioxidants are also commonly added to emulsion formulations to prevent deterioration of the formulation. Antioxidants used may be free radical scavengers such as tocopherols, alkyl gallates, butylated hydroxyanisole, butylated hydroxytoluene, or reducing agents such as ascorbic acid and sodium metabisulfite, and antioxidant synergists such as citric acid, tartaric acid, and lecithin.

The application of emulsion formulations via dermatological, oral and parenteral routes and methods for their manufacture have been reviewed in the literature (Idson, in *Pharmaceutical Dosage Forms*, Lieberman, Rieger and Banker (Eds.), 1988, Marcel Dekker, Inc., New York, N.Y., volume 1, p. 199). Emulsion formulations for oral delivery have been very widely used because of reasons of ease of formulation, efficacy from an absorption and bioavailability standpoint. (Rosoff, in *Pharmaceutical Dosage Forms*, Lieberman, Rieger and Banker (Eds.), 1988, Marcel Dekker, Inc., New York, N.Y., volume 1, p. 245; Idson, in *Pharmaceutical Dosage Forms*, Lieberman, Rieger and Banker (Eds.), 1988, Marcel Dekker, Inc., New York, N.Y., volume 1, p. 199). Mineral-oil base laxatives, oil-soluble vitamins and high fat nutritive preparations are among the materials that have commonly been administered orally as o/w emulsions.

In one embodiment of the present invention, the compositions of oligonucleotides and nucleic acids are formulated as microemulsions. A microemulsion may be defined as a system of water, oil and amphiphile which is a single optically isotropic and thermodynamically stable liquid solution (Rosoff, in *Pharmaceutical Dosage Forms*, Lieberman, Rieger and Banker (Eds.), 1988, Marcel Dekker, Inc., New York, N.Y., volume 1, p. 245). Typically microemulsions are systems that are prepared by first dispersing an oil in an aqueous surfactant solution and then adding a sufficient amount of a fourth component, generally an intermediate chain-length alcohol to form a transparent system. Therefore, microemulsions have also been described as thermodynamically stable, isotropically clear dispersions of two immiscible liquids that are stabilized by interfacial films of surface-active molecules (Leung and Shah, in: *Controlled Release of Drugs: Polymers and Aggregate Systems*, Rosoff, M., Ed., 1989, VCH Publishers, New York, pages 185–215). Microemulsions commonly are prepared via a combination of three to five components that include oil, water, surfactant, cosurfactant and electrolyte. Whether the microemulsion is of the water-in-oil (w/o) or an oil-in-water (o/w) type is dependent on the properties of the oil and surfactant used and on the structure and geometric packing of the polar heads and hydrocarbon tails of the surfactant molecules (Schott, in *Remington's Pharmaceutical Sciences*, Mack Publishing Co., Easton, Pa., 1985, p. 271).

The phenomenological approach utilizing phase diagrams has been extensively studied and has yielded a comprehensive knowledge, to one skilled in the art, of how to formulate microemulsions (Rosoff, in *Pharmaceutical Dosage Forms*, Lieberman, Rieger and Banker (Eds.), 1988, Marcel Dekker, Inc., New York, N.Y., volume 1, p. 245; Block, in *Pharmaceutical Dosage Forms*, Lieberman, Rieger and Banker (Eds.), 1988, Marcel Dekker, Inc., New York, N.Y., volume 1, p. 335). Compared to conventional emulsions, microemulsions offer the advantage of solubilizing water-insoluble drugs in a formulation of thermodynamically stable droplets that are formed spontaneously.

Surfactants used in the preparation of microemulsions include, but are not limited to, ionic surfactants, non-ionic surfactants, Brij 96, polyoxyethylene oleyl ethers, polyglycerol fatty acid esters, tetraglycerol monolaurate (ML310), tetraglycerol monooleate (MO310), hexaglycerol monooleate (PO310), hexaglycerol pentaoleate (PO500), decaglycerol monocaprate (MCA750), decaglycerol monooleate (MO750), decaglycerol sequioleate (SO750), decaglycerol decaoleate (DAO750), alone or in combination with cosurfactants. The cosurfactant, usually a short-chain alcohol such as ethanol, 1-propanol, and 1-butanol, serves to increase the interfacial fluidity by penetrating into the surfactant film and consequently creating a disordered film because of the void space generated among surfactant molecules. Microemulsions may, however, be prepared without the use of cosurfactants and alcohol-free self-emulsifying microemulsion systems are known in the art. The aqueous phase may typically be, but is not limited to, water, an aqueous solution of the drug, glycerol, PEG300, PEG400, polyglycerols, propylene glycols, and derivatives of ethylene glycol. The oil phase may include, but is not limited to, materials such as Captex 300, Captex 355, Capmul MCM, fatty acid esters, medium chain (C8–C12) mono, di, and tri-glycerides, polyoxyethylated glyceryl fatty acid esters, fatty alcohols, polyglycolized glycerides, saturated polyglycolized C8–C10 glycerides, vegetable oils and silicone oil.

Microemulsions are particularly of interest from the standpoint of drug solubilization and the enhanced absorption of drugs. Lipid based microemulsions (both o/w and w/o) have been proposed to enhance the oral bioavailability of drugs, including peptides (Constantinides et al., *Pharmaceutical Research*, 1994, 11, 1385–1390; Ritschel, *Meth. Find. Exp. Clin. Pharmacol.*, 1993, 13, 205). Microemulsions afford advantages of improved drug solubilization, protection of drug from enzymatic hydrolysis, possible enhancement of drug absorption due to surfactant-induced alterations in membrane fluidity and permeability, ease of preparation, ease of oral administration over solid dosage forms, improved clinical potency, and decreased toxicity (Constantinides et al., *Pharmaceutical Research*, 1994, 11, 1385; Ho et al., *J. Pharm. Sci.*, 1996, 85, 138–143). Often microemulsions may form spontaneously when their components are brought together at ambient temperature. This may be particularly advantageous when formulating thermolabile drugs, peptides or oligonucleotides. Microemulsions have also been effective in the transdermal delivery of active components in both cosmetic and pharmaceutical applications. It is expected that the microemulsion compositions and formulations of the present invention will facilitate the increased systemic absorption of oligonucleotides and nucleic acids from the gastrointestinal tract, as well as improve the local cellular uptake of oligonucleotides and nucleic acids within the gastrointestinal tract, vagina, buccal cavity and other areas of administration.

Microemulsions of the present invention may also contain additional components and additives such as sorbitan monostearate (Grill 3), Labrasol, and penetration enhancers to improve the properties of the formulation and to enhance the absorption of the oligonucleotides and nucleic acids of the present invention. Penetration enhancers used in the microemulsions of the present invention may be classified as belonging to one of five broad categories—surfactants, fatty acids, bile salts, chelating agents, and non-chelating non-surfactants (Lee et al., *Critical Reviews in Therapeutic Drug Carrier Systems*, 1991, p. 92). Each of these classes has been discussed above.

Liposomes

There are many organized surfactant structures besides microemulsions that have been studied and used for the formulation of drugs. These include monolayers, micelles, bilayers and vesicles. Vesicles, such as liposomes, have attracted great interest because of their specificity and the duration of action they offer from the standpoint of drug delivery. As used in the present invention, the term "liposome" means a vesicle composed of amphiphilic lipids arranged in a spherical bilayer or bilayers.

Liposomes are unilamellar or multilamellar vesicles which have a membrane formed from a lipophilic material and an aqueous interior. The aqueous portion contains the composition to be delivered. Cationic liposomes possess the advantage of being able to fuse to the cell wall. Non-cationic liposomes, although not able to fuse as efficiently with the cell wall, are taken up by macrophages in vivo.

In order to cross intact mammalian skin, lipid vesicles must pass through a series of fine pores, each with a diameter less than 50 nm, under the influence of a suitable transdermal gradient. Therefore, it is desirable to use a liposome which is highly deformable and able to pass through such fine pores.

Further advantages of liposomes include; liposomes obtained from natural phospholipids are biocompatible and biodegradable; liposomes can incorporate a wide range of water and lipid soluble drugs; liposotes can protect encapsulated drugs in their internal compartments from metabolism and degradation (Rosoff, in *Pharmaceutical Dosage Forms*, Lieberman, Rieger and Banker (Ends.), 1988, Marcel Dekker, Inc., New York, N.Y., volume 1, p. 245). Important considerations in the preparation of liposome formulations are the lipid surface charge, vesicle size and the aqueous volume of the liposomes.

Liposomes are useful for the transfer and delivery of active ingredients to the site of action. Because the liposomal membrane is structurally similar to biological membranes, when liposomes are applied to a tissue, the liposomes start to merge with the cellular membranes. As the merging of the liposome and cell progresses, the liposomal contents are emptied into the cell where the active agent may act.

Liposomal formulations have been the focus of extensive investigation as the mode of delivery for many drugs. There is growing evidence that for topical administration, liposomes present several advantages over other formulations. Such advantages include reduced side-effects related to high systemic absorption of the administered drug, increased accumulation of the administered drug at the desired target, and the ability to administer a wide variety of drugs, both hydrophilic and hydrophobic, into the skin.

Several reports have detailed the ability of liposomes to deliver agents including high-molecular weight DNA into the skin. Compounds including analgesics, antibodies, hormones and high-molecular weight DNAs have been administered to the skin. The majority of applications resulted in the targeting of the upper epidermis.

Liposomes fall into two broad classes. Cationic liposomes are positively charged liposomes which interact with the negatively charged DNA molecules to form a stable complex. The positively charged DNA/liposome complex binds to the negatively charged cell surface and is internalized in an endosome. Due to the acidic pH within the endosome, the liposomes are ruptured, releasing their contents into the cell cytoplasm (Wang et al., *Biochem. Biophys. Res. Commun.*, 1987, 147, 980–985).

Liposomes which are pH-sensitive or negatively-charged, entrap DNA rather than complex with it. Since both the DNA and the lipid are similarly charged, repulsion rather than complex formation occurs. Nevertheless, some DNA is entrapped within the aqueous interior of these liposomes. pH-sensitive liposomes have been used to deliver DNA encoding the thymidine kinase gene to cell monolayers in culture. Expression of the exogenous gene was detected in the target cells (Zhou et al., *Journal of Controlled Release*, 1992, 19, 269–274).

One major type of liposomal composition includes phospholipids other than naturally-derived phosphatidylcholine. Neutral liposome compositions, for example, can be formed from dimyristoyl phosphatidylcholine (DMPC) or dipalmitoyl phosphatidylcholine (DPPC). Anionic liposome compositions generally are formed from dimyristoyl phosphatidylglycerol, while anionic fusogenic liposomes are formed primarily from dioleoyl phosphatidylethanolamine (DOPE). Another type of liposomal composition is formed from phosphatidylcholine (PC) such as, for example, soybean PC, and egg PC. Another type is formed from mixtures of phospholipid and/or phosphatidylcholine and/or cholesterol.

Several studies have assessed the topical delivery of liposomal drug formulations to the skin. Application of liposomes containing interferon to guinea pig skin resulted in a reduction of skin herpes sores while delivery of interferon via other means (e.g. as a solution or as an emulsion) were ineffective (Weiner et al., *Journal of Drug Targeting*, 1992, 2, 405–410). Further, an additional study tested the efficacy of interferon administered as part of a liposomal formulation to the administration of interferon using an aqueous system, and concluded that the liposomal formulation was superior to aqueous administration (du Plessis et al., *Antiviral Research*, 1992, 18, 259–265).

Non-ionic liposomal systems have also been examined to determine their utility in the delivery of drugs to the skin, in particular systems comprising non-ionic surfactant and cholesterol. Non-ionic liposomal formulations comprising Novasome™ I (glyceryl dilaurate/cholesterol/ polyoxyethylene-10-stearyl ether) and Novasome™ II (g-Lyceryl distearate/cholesterol/polyoxyethylene-10-stearyl ether) were used to deliver cyclosporin-A into the dermis of mouse skin. Results indicated that such non-ionic liposomal systems were effective in facilitating the deposition of cyclosporin-A into different layers of the skin (Hu et al. *S.T.P.Pharma. Sci.*, 1994, 4, 6, 466).

Liposomes also include "sterically stabilized" liposomes, a term which, as used herein, refers to liposomes comprising one or more specialized lipids that, when incorporated into liposomes, result in enhanced circulation lifetimes relative to liposomes lacking such specialized lipids. Examples of sterically stabilized liposomes are those in which part of the vesicle-forming lipid portion of the liposome (A) comprises one or more glycolipids, such as monosialoganglioside $G_{M1}$, or (B) is derivatized with one or more hydrophilic polymers, such as a polyethylene glycol (PEG) moiety. While not wishing to be bound by any particular theory, it is thought in the art that, at least for sterically stabilized liposomes containing gangliosides, sphingomyelin, or PEG-derivatized lipids, the enhanced circulation half-life of these sterically stabilized liposomes derives from a reduced uptake into cells of the reticuloendothelial system (RES) (Allen et al., *FEBS Letters*, 1987, 223, 42; Wu et al., *Cancer Research*, 1993, 53, 3765).

Various liposomes comprising one or more glycolipids are known in the art. Papahadjopoulos et al. (*Ann. N.Y. Acad. Sci.*, 1987, 507, 64) reported the ability of monosialoganglioside $G_{M1}$, galactocerebroside sulfate and phosphatidylinositol to improve blood half-lives of liposomes. These findings were expounded upon by Gabizon et al. (*Proc. Natl. Acad. Sci. U.S.A.*, 1988, 85, 6949). U.S. Pat. No. 4,837,028 and WO 88/04924, both to Allen et al., disclose liposomes comprising (1) sphingomyelin and (2) the ganglioside $G_{M1}$ or a galactocerebroside sulfate ester. U.S. Pat. No. 5,543,152 (Webb et al.) discloses liposomes comprising sphingomyelin. Liposomes comprising 1,2-sn-dimyristoylphosphatidylcholine are disclosed in WO 97/13499 (Lim et al.).

Many liposomes comprising lipids derivatized with one or more hydrophilic polymers, and methods of preparation thereof, are known in the art. Sunamoto et al. (*Bull. Chem. Soc. Jpn.*, 1980, 53, 2778) described liposomes comprising a nonionic detergent, $2C_{12}15G$, that contains a PEG moiety. Illum et al. (*FEBS Lett.*, 1984, 167, 79) noted that hydrophilic coating of polystyrene particles with polymeric glycols results in significantly enhanced blood half-lives. Synthetic phospholipids modified by the attachment of carboxylic groups of polyalkylene glycols (e.g., PEG) are described by Sears (U.S. Pat. Nos. 4,426,330 and 4,534,899). Klibanov et al. (*FEBS Lett.*, 1990, 268, 235) described experiments demonstrating that liposomes comprising phosphatidylethanolamine (PE) derivatized with PEG or PEG stearate have significant increases in blood circulation half-lives. Blume et al. (*Biochimica et Biophysica Acta*, 1990, 1029, 91) extended such observations to other PEG-derivatized phospholipids, e.g., DSPE-PEG, formed from the combination of distearoylphosphatidylethanolamine (DSPE) and PEG. Liposomes having covalently bound PEG moieties on their external surface are described in European Patent No. EP 0 445 131 B1 and WO 90/04384 to Fisher. Liposome compositions containing 1–20 mole percent of PE derivatized with PEG, and methods of use thereof, are described by Woodle et al. (U.S. Pat. Nos. 5,013,556 and 5,356,633) and Martin et al. (U.S. Pat. No. 5,213,804 and European Patent No. EP 0 496 813 B1). Liposomes comprising a number of other lipid-polymer conjugates are disclosed in WO 91/05545 and U.S. Pat. No. 5,225,212 (both to Martin et al.) and in WO 94/20073 (Zalipsky et al.) Liposomes comprising PEG-modified ceramide lipids are described in WO 96/10391 (Choi et al.). U.S. Pat. Nos. 5,540,935 (Miyazaki et al.) and 5,556,948 (Tagawa et al.) describe PEG-containing liposomes that can be further derivatized with functional moieties on their surfaces.

A limited number of liposomes comprising nucleic acids are known in the art. WO 96/40062 to Thierry et al. discloses methods for encapsulating high molecular weight nucleic acids in liposomes. U.S. Pat. No. 5,264,221 to Tagawa et al. discloses protein-bonded liposomes and asserts that the contents of such liposomes may include an antisense RNA. U.S. Pat. No. 5,665,710 to Rahman et al. describes certain methods of encapsulating oligodeoxynucleotides in liposomes. WO 97/04787 to Love et al. discloses liposomes comprising antisense oligonucleotides targeted to the raf gene.

Transfersomes are yet another type of liposomes, and are highly deformable lipid aggregates which are attractive candidates for drug delivery vehicles. Transfersomes may be described as lipid droplets which are so highly deformable that they are easily able to penetrate through pores which are smaller than the droplet. Transfersomes are adaptable to the environment in which they are used, e.g. they are self-optimizing (adaptive to the shape of pores in the skin), self-repairing, frequently reach their targets without fragmenting, and often self-loading. To make transfersomes it is possible to add surface edge-activators, usually surfactants, to a standard liposomal composition. Transfersomes have been used to deliver serum albumin to the skin. The transfersome-mediated delivery of serum albumin has been shown to be as effective as subcutaneous injection of a solution containing serum albumin.

Surfactants find wide application in formulations such as emulsions (including microemulsions) and liposomes. The most common way of classifying and ranking the properties of the many different types of surfactants, both natural and synthetic, is by the use of the hydrophile/lipophile balance (HLB). The nature of the hydrophilic group (also known as the "head") provides the most useful means for categorizing the different surfactants used in formulations (Rieger, in *Pharmaceutical Dosage Forms*, Marcel Dekker, Inc., New York, N.Y., 1988, p. 285).

If the surfactant molecule is not ionized, it is classified as a nonionic surfactant. Nonionic surfactants find wide application in pharmaceutical and cosmetic products and are usable over a wide range of pH values. In general their HLB values range from 2 to about 18 depending on their structure. Nonionic surfactants include nonionic esters such as ethylene glycol esters, propylene glycol esters, glyceryl esters, polyglyceryl esters, sorbitan esters, sucrose esters, and ethoxylated esters. Nonionic alkanolamides and ethers such as fatty alcohol ethoxylates, propoxylated alcohols, and ethoxylated/propoxylated block polymers are also included in this class. The polyoxyethylene surfactants are the most popular members of the nonionic surfactant class.

If the surfactant molecule carries a negative charge when it is dissolved or dispersed in water, the surfactant is classified as anionic. Anionic surfactants include carboxylates such as soaps, acyl lactylates, acyl amides of amino acids, esters of sulfuric acid such as alkyl sulfates and ethoxylated alkyl sulfates, sulfonates such as alkyl benzene sulfonates, acyl isethionates, acyl taurates and sulfosuccinates, and phosphates. The most important members of the anionic surfactant class are the alkyl sulfates and the soaps.

If the surfactant molecule carries a positive charge when it is dissolved or dispersed in water, the surfactant is classified as cationic. Cationic surfactants include quaternary ammonium salts and ethoxylated amines. The quaternary ammonium salts are the most used members of this class.

If the surfactant molecule has the ability to carry either a positive or negative charge, the surfactant is classified as amphoteric. Amphoteric surfactants include acrylic acid derivatives, substituted alkylamides, N-alkylbetaines and phosphatides.

The use of surfactants in drug products, formulations and in emulsions has been reviewed (Rieger, in *Pharmaceutical Dosage Forms*, Marcel Dekker, Inc., New York, N.Y., 1988, p. 285).

Penetration Enhancers

In one embodiment, the present invention employs various penetration enhancers to effect the efficient delivery of nucleic acids, particularly oligonucleotides, to the skin of animals. Most drugs are present in solution in both ionized and nonionized forms. However, usually only lipid soluble or lipophilic drugs readily cross cell membranes. It has been discovered that even non-lipophilic drugs may cross cell membranes if the membrane to be crossed is treated with a penetration enhancer. In addition to aiding the diffusion of non-lipophilic drugs across cell membranes, penetration enhancers also enhance the permeability of lipophilic drugs.

Penetration enhancers may be classified as belonging to one of five broad categories, i.e., surfactants, fatty acids, bile salts, chelating agents, and non-chelating non-surfactants (Lee et al., *Critical Reviews in Therapeutic Drug Carrier Systems*, 1991, p.92). Each of the above mentioned classes of penetration enhancers are described below in greater detail.

Surfactants: In connection with the present invention, surfactants (or "surface-active agents") are chemical entities which, when dissolved in an aqueous solution, reduce the surface tension of the solution or the interfacial tension between the aqueous solution and another liquid, with the result that absorption of oligonucleotides through the mucosa is enhanced. In addition to bile salts and fatty acids, these penetration enhancers include, for example, sodium lauryl sulfate, polyoxyethylene-9-lauryl ether and polyoxyethylene-20-cetyl ether) (Lee et al., *Critical Reviews in Therapeutic Drug Carrier Systems*, 1991, p.92); and perfluorochemical emulsions, such as FC-43. Takahashi et al., *J. Pharm. Pharmacol.*, 1988, 40, 252).

Fatty acids: Various fatty acids and their derivatives which act as penetration enhancers include, for example, oleic acid, lauric acid, capric acid (n-decanoic acid), myristic acid, palmitic acid, stearic acid, linoleic acid, linolenic acid, dicaprate, tricaprate, monoolein (1-monooleoyl-rac-glycerol), dilaurin, caprylic acid, arachidonic acid, glycerol 1-monocaprate, 1-dodecylazacycloheptan-2-one, acylcarnitines, acylcholines, $C_{1-10}$ alkyl esters thereof (e.g., methyl, isopropyl and t-butyl), and mono- and di-glycerides thereof (i.e., oleate, laurate, caprate, myristate, palmitate, stearate, linoleate, etc.) (Lee et al., *Critical Reviews in Therapeutic Drug Carrier Systems*, 1991, p.92; Muranishi, *Critical Reviews in Therapeutic Drug Carrier Systems*, 1990 7, 1–33; El Hariri et al., J. Pharm. Pharmacol., 1992, 44, (651–654).

Bile salts: The physiological role of bile includes the facilitation of dispersion and absorption of lipids and fat-soluble vitamins (Brunton, Chapter 38 in: Goodman & Gilman's *The Pharmacological Basis of Therapeutics*, 9th Ed., Hardman et al. Eds., McGraw-Hill, New York, 1996, pp. 934–935). Various natural bile salts, and their synthetic derivatives, act as penetration enhancers. Thus the term "bile salts" includes any of the naturally occurring components of bile as well as any of their synthetic derivatives. The bile salts of the invention include, for example, cholic acid (or its pharmaceutically acceptable sodium salt, sodium cholate), dehydrocholic acid (sodium dehydrocholate), deoxycholic acid (sodium deoxycholate), glucholic acid (sodium glucholate), glycholic acid (sodium glycocholate), glycodeoxycholic acid (sodium glycodeoxycholate), taurocholic acid (sodium taurocholate), taurodeoxycholic acid (sodium taurodeoxycholate), chenodeoxycholic acid (sodium chenodeoxycholate), ursodeoxycholic acid (UDCA), sodium tauro-24,25-dihydro-fusidate (STDHF), sodium glycodihydrofusidate and polyoxyethylene-9-lauryl ether (POE) (Lee et al., *Critical Reviews in Therapeutic Drug Carrier Systems*, 1991, page 92; Swinyard, Chapter 39 *In: Remington's Pharmaceutical Sciences*, 18th Ed., Gennaro, ed., Mack Publishing Co., Easton, Pa., 1990, pages 782–783; Muranishi, *Critical Reviews in Therapeutic Drug Carrier Systems*, 1990, 7, 1–33; Yamamoto et al., *J. Pharm. Exp. Ther.*, 1992, 263, 25; Yamashita et al., *J. Pharm. Sci.*, 1990, 79, 579–583).

Chelating Agents: Chelating agents, as used in connection with the present invention, can be defined as compounds that remove metallic ions from solution by forming complexes therewith, with the result that absorption of oligonucleotides through the mucosa is enhanced. With regards to their use as penetration enhancers in the present invention, chelating agents have the added advantage of also serving as DNase inhibitors, as most characterized DNA nucleases require a divalent metal ion for catalysis and are thus inhibited by chelating agents (Jarrett, *J. Chromatogr.*, 1993, 618, 315–339). Chelating agents of the invention include but are not limited to disodium ethylenediaminetetraacetate (EDTA), citric acid, salicylates (e.g., sodium salicylate, 5-methoxysalicylate and homovanilate), N-acyl derivatives of collagen, laureth-9 and N-amino acyl derivatives of beta-diketones (enamines)(Lee et al., *Critical Reviews in Therapeutic Drug Carrier Systems*, 1991, page 92; Muranishi, *Critical Reviews in Therapeutic Drug Carrier Systems*, 1990, 7, 1–33; Buur et al., *J. Control Rel.*, 1990, 14, 43–51).

Non-chelating non-surfactants: As used herein, non-chelating non-surfactant penetration enhancing compounds can be defined as compounds that demonstrate insignificant activity as chelating agents or as surfactants but that nonetheless enhance absorption of oligonucleotides through the alimentary mucosa (Muranishi, *Critical Reviews in Thera-* peutic *Drug Carrier Systems,* 1990, 7, 1–33). This class of penetration enhancers include, for example, unsaturated cyclic ureas, 1-alkyl- and 1-alkenylazacyclo-alkanone derivatives (Lee et al., *Critical Reviews in Therapeutic Drug Carrier Systems,* 1991, page 92); and non-steroidal anti-inflammatory agents such as diclofenac sodium, indomethacin and phenylbutazone (Yamashita et al., *J. Pharm. Pharmacol.,* 1987, 39, 621–626).

Agents that enhance uptake of oligonucleotides at the cellular level may also be added to the pharmaceutical and other compositions of the present invention. For example, cationic lipids, such as lipofectin (Junichi et al, U.S. Pat. No. 5,705,188), cationic glycerol derivatives, and polycationic molecules, such as polylysine (Lollo et al., PCT Application WO 97/30731), are also known to enhance the cellular uptake of oligonucleotides.

Other agents may be utilized to enhance the penetration of the administered nucleic acids, including glycols such as ethylene glycol and propylene glycol, pyrrols such as 2-pyrrol, azones, and terpenes such as limonene and menthone.

Carriers

Certain compositions of the present invention also incorporate carrier compounds in the formulation. As used herein, "carrier compound" or "carrier" can refer to a nucleic acid, or analog thereof, which is inert (i.e., does not possess biological activity per se) but is recognized as a nucleic acid by in vivo processes that reduce the bioavailability of a nucleic acid having biological activity by, for example, degrading the biologically active nucleic acid or promoting its removal from circulation. The coadministration of a nucleic acid and a carrier compound, typically with an excess of the latter substance, can result in a substantial reduction of the amount of nucleic acid recovered in the liver, kidney or other extracirculatory reservoirs, presumably due to competition between the carrier compound and the nucleic acid for a common receptor. For example, the recovery of a partially phosphorothioate oligonucleotide in hepatic tissue can be reduced when it is coadministered with polyinosinic acid, dextran sulfate, polycytidic acid or 4-acetamido-4'isothiocyano-stilbene-2,2'-disulfonic acid (Miyao et al., *Antisense Res. Dev.,* 1995, 5, 115–121; Takakura et al., *Antisense & Nucl. Acid Drug Dev.,* 1996, 6, 177–183).

Excipients

In contrast to a carrier compound, a "pharmaceutical carrier" or "excipient" is a pharmaceutically acceptable solvent, suspending agent or any other pharmacologically inert vehicle for delivering one or more nucleic acids to an animal. The excipient may be liquid or solid and is selected, with the planned manner of administration in mind, so as to provide for the desired bulk, consistency, etc., when combined with a nucleic acid and the other components of a given pharmaceutical composition. Typical pharmaceutical carriers include, but are not limited to, binding agents (e.g., pregelatinized maize starch, polyvinylpyrrolidone or hydroxypropyl methylcellulose, etc.); fillers (e.g., lactose and other sugars, microcrystalline cellulose, pectin, gelatin, calcium sulfate, ethyl cellulose, polyacrylates or calcium hydrogen phosphate, etc.); lubricants (e.g., magnesium stearate, talc, silica, colloidal silicon dioxide, stearic acid, metallic stearates, hydrogenated vegetable oils, corn starch, polyethylene glycols, sodium benzoate, sodium acetate, etc.); disintegrants (e.g., starch, sodium starch glycolate, etc.); and wetting agents (e.g., sodium lauryl sulphate, etc.).

Pharmaceutically acceptable organic or inorganic excipient suitable for non-parenteral administration which do not deleteriously react with nucleic acids can also be used to formulate the compositions of the present invention. Suitable pharmaceutically acceptable carriers include, but are not limited to, water, salt solutions, alcohols, polyethylene glycols, gelatin, lactose, amylose, magnesium stearate, talc, silicic acid, viscous paraffin, hydroxymethylcellulose, polyvinylpyrrolidone and the like.

Formulations for topical administration of nucleic acids may include sterile and non-sterile aqueous solutions, non-aqueous solutions in common solvents such as alcohols, or solutions of the nucleic acids in liquid or solid oil bases. The solutions may also contain buffers, diluents and other suitable additives. Pharmaceutically acceptable organic or inorganic excipients suitable for non-parenteral administration which do not deleteriously react with nucleic acids can be used.

Suitable pharmaceutically acceptable excipients include, but are not limited to, water, salt solutions, alcohol, polyethylene glycols, gelatin, lactose, amylose, magnesium stearate, talc, silicic acid, viscous paraffin, hydroxymethylcellulose, polyvinylpyrrolidone and the like.

Other Components

The compositions of the present invention may additionally contain other adjunct components conventionally found in pharmaceutical compositions, at their art-established usage levels. Thus, for example, the compositions may contain additional, compatible, pharmaceutically-active materials such as, for example, antipruritics, astringents, local anesthetics or anti-inflammatory agents, or may contain additional materials useful in physically formulating various dosage forms of the compositions of the present invention, such as dyes, flavoring agents, preservatives, antioxidants, opacifiers, thickening agents and stabilizers. However, such materials, when added, should not unduly interfere with the biological activities of the components of the compositions of the present invention. The formulations can be sterilized and, if desired, mixed with auxiliary agents, e.g., lubricants, preservatives, stabilizers, wetting agents, emulsifiers, salts for influencing osmotic pressure, buffers, colorings, flavorings and/or aromatic substances and the like which do not deleteriously interact with the nucleic acid(s) of the formulation.

Aqueous suspensions may contain substances which increase the viscosity of the suspension including, for example, sodium carboxymethylcellulose, sorbitol and/or dextran. The suspension may also contain stabilizers.

Certain embodiments of the invention provide pharmaceutical compositions containing (a) one or more antisense compounds and (b) one or more other chemotherapeutic agents which function by a non-antisense mechanism. Examples of such chemotherapeutic agents include but are not limited to daunorubicin, daunomycin, dactinomycin, doxorubicin, epirubicin, idarubicin, esorubicin, bleomycin, mafosfamide, itosfamide, cytosine arabinoside, bis-chloroethylnitrosurea, busulfan, mitomycin C, actinomycin D, mithramycin, prednisone, hydroxyprogesterone, testosterone, tamoxifen, dacarbazine, procarbazine, hexamethylmelamine, pentamethylmelamine, mitoxantrone, amsacrine, chlorambucil, methylcyclohexylnitrosurea, nitrogen mustards, melphalan, cyclophosphamide, 6-mercaptopurine, 6-thioguanine, cytarabine, 5-azacytidine, hydroxyurea, deoxycoformycin, 4-hydroxyperoxycyclophosphoramide, 5-fluorouracil (5-FU), 5-fluorodeoxyuridine (5-FUdR), methotrexate (MTX), colchicine, taxol, vincristine, vinblastine, etoposide (VP-16), trimetrexate, irinotecan, topotecan, gemcitabine, teniposide, cisplatin and diethylstilbestrol (DES). See, generally, *The Merck Manual of Diagnosis and Therapyl,* 15th Ed. 1987, pp. 1206–1228, Berkow et al., eds., Rahway, N.J. When used with the compounds of the invention, such chemotherapeutic agents may be used individually (e.g., 5-FU and oligonucleotide), sequentially (e.g., 5-FU and oligonucleotide for a period of time followed by MTX and oligonucleotide), or in combination with one or more other such chemotherapeutic agents (e.g., 5-FU, MTX and oligonucleotide, or 5-FU, radiotherapy and oligonucleotide). Anti-inflammatory drugs, including but not limited to non-steroidal anti-inflammatory drugs and corticosteroids, and antiviral drugs, including but not limited to ribivirin, vidarabine, acyclovir and ganciclovir, may also be combined in compositions of the invention. See, generally, *The Merck Manual of Diagnosis and Therapy,* 15th Ed., Berkow et al., eds., 1987, Rahway, N.J., pages 2499–2506 and 46–49, respectively). Other non-antisense chemotherapeutic agents are also within the scope of this invention. Two or more combined compounds may be used together or sequentially.

In another related embodiment, compositions of the invention may contain one or more antisense compounds, particularly oligonucleotides, targeted to a first nucleic acid and one or more additional antisense compounds targeted to a second nucleic acid target. Numerous examples of antisense compounds are known in the art. Two or more combined compounds may be used together or sequentially.

The formulation of therapeutic compositions and their subsequent administration is believed to be within the skill of those in the art. Dosing is dependent on severity and responsiveness of the disease state to be treated, with the course of treatment lasting from several days to several months, or until a cure is effected or a diminution of the disease state is achieved. Optimal dosing schedules can be calculated from measurements of drug accumulation in the body of the patient. Persons of ordinary skill can easily determine optimum dosages, dosing methodologies and repetition rates. Optimum dosages may vary depending on the relative potency of individual oligonucleotides, and can generally be estimated based on $EC_{50}$s found to be effective in in vitro and in vivo animal models. In general, dosage is from 0.01 ug to 100 g per kg of body weight, and may be given once or more daily, weekly, monthly or yearly, or even once every 2 to 20 years. Persons of ordinary skill in the art can easily estimate repetition rates for dosing based on measured residence times and concentrations of the drug in bodily fluids or tissues. Following successful treatment, it may be desirable to have the patient undergo maintenance therapy to prevent the recurrence of the disease state, wherein the oligonucleotide is administered in maintenance doses, ranging from 0.01 ug to 100 g per kg of body weight, once or more daily, to once every 20 years.

While the present invention has been described with specificity in accordance with certain of its preferred embodiments, the following examples serve only to illustrate the invention and are not intended to limit the same.

EXAMPLES

Example 1
Nucleoside Phosphoramidites for Oligonucleotide Synthesis Deoxy and 21-alkoxy amidites 2'-Deoxy and 2'-methoxy beta-cyanoethyldiisopropyl phosphoramidites were purchased from commercial sources (e.g. Chemgenes, Needham Mass. or Glen Research, Inc. Sterling Va.). Other 2'-O-alkoxy substituted nucleoside amidites are prepared as described in U.S. Pat. No. 5,506, 351, herein incorporated by reference. For oligonucleotides synthesized using 2'-alkoxy amidites, the standard cycle for unmodified oligonucleotides was utilized, except the wait step after pulse delivery of tetrazole and base was increased to 360 seconds.

Oligonucleotides containing 5-methyl-2'-deoxycytidine (5-Me-C) nucleotides were synthesized according to published methods [Sanghvi, et. al., *Nucleic Acids Research,* 1993, 21, 3197–3203] using commercially available phosphoramidites (Glen Research, Sterling Va. or ChemGenes, Needham Mass.).

2'-Fluoro amidites
  2'-Fluorodeoxyadenosine amidites
  2'-fluoro oligonucleotides were synthesized as described previously [Kawasaki, et. al., *J. Med. Chem.,* 1993, 36, 831–841] and U.S. Pat. No. 5,670,633, herein incorporated by reference. Briefly, the protected nucleoside N6-benzoyl-2'-deoxy-2'-fluoroadenosine was synthesized utilizing commercially available 9-beta-D-arabinofuranosyladenine as starting material and by modifying literature procedures whereby the 2'-alpha-fluoro atom is introduced by a $S_N2$-displacement of a 2'-beta-trityl group. Thus N6-benzoyl-9-beta-D-arabinofuranosyladenine was selectively protected in moderate yield as the 3',5'-ditetrahydropyranyl (THP) intermediate. Deprotection of the THP and N6-benzoyl groups was accomplished using standard methodologies and standard methods were used to obtain the 5'-dimethoxytrityl-(DMT) and 5'-DMT-3'-phosphoramidite intermediates.

2'-Fluorodeoxyguanosine
  The synthesis of 2'-deoxy-2'-fluoroguanosine was accomplished using tetraisopropyldisiloxanyl (TPDS) protected 9-beta-D-arabinofuranosylguanine as starting material, and conversion to the intermediate diisobutyryl-arabinofuranosylguanosine. Deprotection of the TPDS group was followed by protection of the hydroxyl group with THP to give diisobutyryl di-THP protected arabino-furanosylguanine. Selective O-deacylation and triflation was followed by treatment of the crude product with fluoride, then deprotection of the THP groups. Standard methodologies were used to obtain the 5'-DMT- and 5'-DMT-3'-phosphoramidites.

2'-Fluorouridine
  Synthesis of 2'-deoxy-2'-fluorouridine was accomplished by the modification of a literature procedure in which 2,2'-anhydro-1-beta-D-arabinofuranosyluracil was treated with 70% hydrogen fluoride-pyridine. Standard procedures were used to obtain the 5'-DMT and 5'-DMT-3'phosphoramidites.

2'-Fluorodeoxycytidine
  2'-deoxy-2'-fluorocytidine was synthesized via amination of 2'-deoxy-2'-fluorouridine, followed by selective protection to give N4-benzoyl-2'-deoxy-2'-fluorocytidine. Standard procedures were used to obtain the 5'-DMT and 5'-DMT-3'phosphoramidites.

2'-O-(2-Methoxyethyl) Modified amidites
  2'-O-Methoxyethyl-substituted nucleoside amidites are prepared as follows, or alternatively, as per the methods of Martin, P., *Helvetica Chimica Acta,* 1995, 78, 486–504.

2,2'-Anhydro[1-(beta-D-arabinofuranosyl)-5-methyluridine]
  5-Methyluridine (ribosylthymine, commercially available through Yamasa, Choshi, Japan) (72.0 g, 0.279 M), diphenyl-carbonate (90.0 g, 0.420 M) and sodium bicarbonate (2.0 g, 0.024 M) were added to DMF (300 mL). The mixture was heated to reflux, with stirring, allowing the evolved carbon dioxide gas to be released in a controlled manner. After 1 hour, the slightly darkened solution was concentrated under reduced pressure. The resulting syrup was poured into diethylether (2.5 L), with stirring. The product formed a gum. The ether was decanted and the residue was dissolved in a minimum amount of methanol (ca. 400 mL). The solution was poured into fresh ether (2.5 L) to yield a stiff gum. The ether was decanted and the gum was dried in a vacuum oven (60° C. at 1 mm Hg for 24 h) to give a solid that was crushed to a light tan powder (57 g, 85% crude yield). The NMR spectrum was consistent with the structure, contaminated with phenol as its sodium salt (ca. 5%). The material was used as is for further reactions (or it can be purified further by column chromatography using a gradient of methanol in ethyl acetate (10–25%) to give a white solid, mp 222–4° C.).

2'-O-Methoxyethyl-5-methyluridins 2,2'-Anhydro-5-methyluridine (195 g, 0.81 M), tris(2-methoxyethyl)borate (231 g, 0.98 M) and 2-methoxyethanol (1.2 L) were added to a 2 L stainless steel pressure vessel and placed in a pre-heated oil bath at 160° C. After heating for 48 hours at 155–160° C., the vessel was opened and the solution evaporated to dryness and triturated with MeOH (200 mL). The residue was suspended in hot acetone (1 L). The insoluble salts were filtered, washed with acetone (150 mL) and the filtrate evaporated. The residue (280 g) was dissolved in $CH_3CN$ (600 mL) and evaporated. A silica gel column (3 kg) was packed in $CH_2Cl_2$/acetone/MeOH (20:5:3) containing 0.5% $Et_3NH$. The residue was dissolved in $CH_2Cl_2$ (250 mL) and adsorbed onto silica (150 g) prior to loading onto the column. The product was eluted with the packing solvent to give 160 g (63%) of product. Additional material was obtained by reworking impure fractions.

2'-O-Methoxyethyl-5'-O-dimethoxytrityl-5-methyluridine

2'-O-Methoxyethyl-5-methyluridine (160 g, 0.506 M) was co-evaporated with pyridine (250 mL) and the dried residue dissolved in pyridine (1.3 L). A first aliquot of dimethoxytrityl chloride (94.3 g, 0.278 M) was added and the mixture stirred at room temperature for one hour. A second aliquot of dimethoxytrityl chloride (94.3 g, 0.278 M) was added and the reaction stirred for an additional one hour. Methanol (170 mL) was then added to stop the reaction. HPLC showed the presence of approximately 70% product. The solvent was evaporated and triturated with $CH_3CN$ (200 mL). The residue was dissolved in $CHCl_3$ (1.5 L) and extracted with 2×500 mL of saturated $NaHCO_3$ and 2×500 mL of saturated NaCl. The organic phase was dried over $Na_2SO_4$, filtered and evaporated. 275 g of residue was obtained. The residue was purified on a 3.5 kg silica gel column, packed and eluted with EtOAc/hexane/acetone (5:5:1) containing 0.5% $Et_3NH$. The pure fractions were evaporated to give 164 g of product. Approximately 20 g additional was obtained from the impure fractions to give a total yield of 183 g (57%).

3'-O-Acetyl-2'-O-methoxyethyl-5'-O-dimethoxytrityl-5-methyluridine

2'-O-Methoxyethyl-5'-O-dimethoxytrityl-5-methyluridine (106 g, 0.167 M), DMF/pyridine (750 mL of a 3:1 mixture prepared from 562 mL of DMF and 188 mL of pyridine) and acetic anhydride (24.38 mL, 0.258 M) were combined and stirred at room temperature for 24 hours. The reaction was monitored by TLC by first quenching the TLC sample with the addition of MeOH. Upon completion of the reaction, as judged by TLC, MeOH (50 mL) was added and the mixture evaporated at 35° C. The residue was dissolved in $CHCl_3$ (800 mL) and extracted with 2×200 mL of saturated sodium bicarbonate and 2×200 mL of saturated NaCl. The water layers were back extracted with 200 mL of $CHCl_3$. The combined organics were dried with sodium sulfate and evaporated to give 122 g of residue (approx. 90% product). The residue was purified on a 3.5 kg silica gel column and eluted using EtOAc/hexane(4:1). Pure product fractions were evaporated to yield 96 g (84%). An additional 1.5 g was recovered from later fractions.

3'-O-Acetyl-2'-O-methoxyethyl-5'-O-dimethoxytrityl-5-methyl-4-triazoleuridine

A first solution was prepared by dissolving 3'-O-acetyl-2'-O-methoxyethyl-5'-O-dimethoxytrityl-5-methyluridine (96 g, 0.144 M) in $CH_3CN$ (700 mL) and set aside. Triethylamine (189 mL, 1.44 M) was added to a solution of triazole (90 g, 1.3 M) in $CH_3CN$ (1 L), cooled to −5° C. and stirred for 0.5 h using an overhead stirrer. $POCl_3$ was added dropwise, over a 30 minute period, to the stirred solution maintained at 0–10° C., and the resulting mixture stirred for an additional 2 hours. The first solution was added dropwise, over a 45 minute period, to the latter solution. The resulting reaction mixture was stored overnight in a cold room. Salts were filtered from the reaction mixture and the solution was evaporated. The residue was dissolved in EtOAc (1 L) and the insoluble solids were removed by filtration. The filtrate was washed with 1×300 mL of $NaHCO_3$ and 2×300 mL of saturated NaCl, dried over sodium sulfate and evaporated. The residue was triturated with EtOAc to give the title compound.

2'-O-Methoxyethyl-5'-O-dimethoxytrityl-5-methylcytidine

A solution of 3'-O-acetyl-2'-O-methoxyethyl-5'-O-dimethoxytrityl-5-methyl-4-triazoleuridine (103 g, 0.141 M) in dioxane (500 mL) and $NH_4OH$ (30 mL) was stirred at room temperature for 2 hours. The dioxane solution was evaporated and the residue azeotroped with MeOH (2×200 mL). The residue was dissolved in MeOH (300 mL) and transferred to a 2 liter stainless steel pressure vessel. MeOH (400 mL) saturated with $NH_3$ gas was added and the vessel heated to 100° C. for 2 hours (TLC showed complete conversion). The vessel contents were evaporated to dryness and the residue was dissolved in EtOAc (500 mL) and washed once with saturated NaCl (200 mL). The organics were dried over sodium sulfate and the solvent was evaporated to give 85 g (95%) of the title compound.

N4-Benzoyl-2'-O-methoxyethyl-5'-O-dimethoxytrityl-5-methylcytidine

2'-O-Methoxyethyl-5'-O-dimethoxytrityl-5-methylcytidine (85 g, 0.134 M) was dissolved in DMF (800 mL) and benzoic anhydride (37.2 g, 0.165 M) was added with stirring. After stirring for 3 hours, TLC showed the reaction to be approximately 95% complete. The solvent was evaporated and the residue azeotroped with MeOH (200 mL). The residue was dissolved in $CHCl_3$ (700 mL) and extracted with saturated $NaHCO_3$ (2×300 mL) and saturated NaCl (2×300 mL), dried over $MgSO_4$ and evaporated to give a residue (96 g). The residue was chromatographed on a 1.5 kg silica column using EtOAc/hexane (1:1) containing 0.5% $Et_3NH$ as the eluting solvent. The pure product fractions were evaporated to give 90 g (90%) of the title compound.

N4-Benzoyl-2'-O-methoxyethyl-5'-O-dimethoxytrityl-5-methylcytidine-3'-amidite

N4-Benzoyl-2'-O-methoxyethyl-5'-O-dimethoxytrityl-5-methylcytidine (74 g, 0.10 M) was dissolved in $CH_2Cl_2$ (1 L) Tetrazole diisopropylamine (7.1 g) and 2-cyanoethoxy-tetra-(isopropyl)phosphite (40.5 mL, 0.123 M) were added with stirring, under a nitrogen atmosphere. The resulting mixture was stirred for 20 hours at room temperature (TLC showed the reaction to be 95% complete). The reaction mixture was extracted with saturated $NaHCO_3$ (1×300 mL) and saturated NaCl (3×300 mL). The aqueous washes were back-extracted with $CH_2Cl_2$ (300 mL), and the extracts were combined, dried over $MgSO_4$ and concentrated. The residue obtained was chromatographed on a 1.5 kg silica column using EtOAc/hexane (3:1) as the eluting solvent. The pure fractions were combined to give 90.6 g (87%) of the title compound.

2'-O-(Aminooxyethyl)nucleoside amidites and 2'-O-(dimethylaminooxyethyl)nucleoside amidites 2'-(Dimethylaminooxyethoxy) nucleoside amidites 2'-(Dimethylaminooxyethoxy) nucleoside amidites [also known in the art as 2'-O-(dimethylaminooxyethyl) nucleoside amidites] are prepared as described in the following paragraphs. Adenosine, cytidine and guanosine nucleoside amidites are prepared similarly to the thymidine (5-methyluridine) except the exocyclic amines are protected with a benzoyl moiety in the case of adenosine and cytidine and with isobutyryl in the case of guanosine.

5'-O-tert-Butyldiphenylsilyl-$O^2$-2'-anhydro-5-methyluridine $O^2$-2'-anhydro-5-methyluridine (Pro. Bio. Sint., Varese, Italy, 100.0 g, 0.416 mmol), dimethylaminopyridine (0.66 g, 0.013 eq, 0.0054 mmol) were dissolved in dry pyridine (500 ml) at ambient temperature under an argon atmosphere and with mechanical stirring. tert-Butyldiphenylchlorosilane (125.8 g, 119.0 mL, 1.1 eq, 0.458 mmol) was added in one portion. The reaction was stirred for 16 h at ambient temperature. TLC (Rf 0.22, ethyl acetate) indicated a complete reaction. The solution was concentrated under reduced pressure to a thick oil. This was partitioned between dichloromethane (1 L) and saturated sodium bicarbonate (2×1 L) and brine (1 L). The organic layer was dried over sodium sulfate and concentrated under reduced pressure to a thick oil. The oil was dissolved in a 1:1 mixture of ethyl acetate and ethyl ether (600 mL) and the solution was cooled to −10° C. The resulting crystalline product was collected by filtration, washed with ethyl ether (3×200 mL) and dried (40° C., 1 mm Hg, 24 h) to 149 g (74.8%) of white solid. TLC and NMR were consistent with pure product.

5'-O-tert-Butyldiphenylsilyl-2'-O-(2-hydroxyethyl)-5-methyluridine

In a 2 L stainless steel, unstirred pressure reactor was added borane in tetrahydrofuran (1.0 M, 2.0 eq, 622 mL). In the fume hood and with manual stirring, ethylene glycol (350 mL, excess) was added cautiously at first until the evolution of hydrogen gas subsided. 5'-O-tert-Butyldiphenylsilyl-$O^2$-2'-anhydro-5-methyluridine (149 g, 0.311 mol) and sodium bicarbonate (0.074 g, 0.003 eq) were added with manual stirring. The reactor was sealed and heated in an oil bath until an internal temperature of 160° C. was reached and then maintained for 16 h (pressure<100 psig). The reaction vessel was cooled to ambient and opened. TLC (Rf 0.67 for desired product and Rf 0.82 for ara-T side product, ethyl acetate) indicated about 70% conversion to the product. In order to avoid additional side product formation, the reaction was stopped, concentrated under reduced pressure (10 to 1 mm Hg) in a warm water bath (40–100° C.) with the more extreme conditions used to remove the ethylene glycol. [Alternatively, once the low boiling solvent is gone, the remaining solution can be partitioned between ethyl acetate and water. The product will be in the organic phase.] The residue was purified by column chromatography (2 kg silica gel, ethyl acetate-hexanes gradient 1:1 to 4:1). The appropriate fractions were combined, stripped and dried to product as a white crisp foam (84 g, 50%), contaminated starting material (17.4 g) and pure reusable starting material 20 g. The yield based on starting material less pure recovered starting material was 58%. TLC and NMR were consistent with 99% pure product.

2'-O-([2-phthalimidoxy)ethyl]-5'-t-butyldiphenylsilyl-5-methyluridine

5'-O-tert-Butyldiphenylsilyl-2'-O-(2-hydroxyethyl)-5-methyluridine (20 g, 36.98mmol) was mixed with triphenylphosphine (11.63 g, 44.36mmol) and N-hydroxyphthalimide (7.24 g, 44.36mmol). It was then dried over $P_2O_5$ under high vacuum for two days at 40° C. The reaction mixture was flushed with argon and dry THF (369.8 mL, Aldrich, sure seal bottle) was added to get a clear solution. Diethyl-azodicarboxylate (6.98 mL, 44.36 mmol) was added dropwise to the reaction mixture. The rate of addition is maintained such that resulting deep red coloration is just discharged before adding the next drop. After the addition was complete, the reaction was stirred for 4 hrs. By that time TLC showed the completion of the reaction (ethylacetate:hexane, 60:40). The solvent was evaporated in vacuum. Residue obtained was placed on a flash column and eluted with ethyl acetate:hexane (60:40), to get 2'-O-([2-phthalimidoxy)ethyl]-5'-t-butyldiphenylsilyl-5-methyluridine as white foam (21.819 g, 86%).

5'-O-tert-butyldiphenylsilyl-2'-O-[(2-formadoximinooxy)ethyl)-5-methyluridine

2'-O-([2-phthalimidoxy)ethyl]-5'-t-butyldiphenylsilyl-5-methyluridine (3.1 g, 4.5 mmol) was dissolved in dry $CH_2Cl_2$ (4.5 mL) and methylhydrazine (300 mL, 4.64 mmol) was added dropwise at −10° C. to 0° C. After 1 h the mixture was filtered, the filtrate was washed with ice cold $CH_2Cl_2$ and the combined organic phase was washed with water, brine and dried over anhydrous $Na_2SO_4$. The solution was concentrated to get 2'-O-(aminooxyethyl) thymidine, which was then dissolved in MeOH (67.5 mL). To this formaldehyde (20% aqueous solution, w/w, 1.1 eq.) was added and the resulting mixture was stirred for 1 h. Solvent was removed under vacuum; residue chromatographed to get 5'-O-tert-butyldiphenylsilyl-2'-O-[(2-formadoximinooxy) ethyl]-5-methyluridine as white foam (1.95 g, 78%).

5'-O-tert-Butyldiphenylsilyl-2'-O-[N,N-dimethylaminooxyethyl]-5-methyluridine

5'-O-tert-butyldiphenylsilyl-2'-O-[(2-formadoximinooxy) ethyl]-5-methyluridine (1.77 g, 3.12 mmol) was dissolved in a solution of 1M pyridinium p-toluenesulfonate (PPTS) in dry MeOH (30.6 mL). Sodium cyanoborohydride (0.39 g, 6.13 mmol) was added to this solution at 10° C. under inert atmosphere. The reaction mixture was stirred for 10 minutes at 10° C. After that the reaction vessel was removed from the ice bath and stirred at room temperature for 2 h, the reaction monitored by TLC (5% MeOH in $CH_2Cl_2$). Aqueous $NaHCO_3$ solution (5%, 10 mL) was added and extracted with ethyl acetate (2×20 mL). Ethyl acetate phase was dried over anhydrous $Na_2SO_4$, evaporated to dryness. Residue was dissolved in a solution of 1M PPTS in MeOH (30.6 mL). Formaldehyde (20% w/w, 30 mL, 3.37 mmol) was added and the reaction mixture was stirred at room temperature for 10 minutes. Reaction mixture cooled to 10° C. in an ice bath, sodium cyanoborohydride (0.39 g, 6.13 mmol) was added and reaction mixture stirred at 10° C. for 10 minutes. After 10 minutes, the reaction mixture was removed from the ice bath and stirred at room temperature for 2 hrs. To the reaction mixture 5% $NaHCO_3$ (25 mL) solution was added and extracted with ethyl acetate (2×25 mL). Ethyl acetate layer was dried over anhydrous $Na_2SO_4$ and evaporated to dryness . The residue obtained was purified by flash column chromatography and eluted with 5% MeOH in $CH_2Cl_2$ to get 5'-O-tert-butyldiphenylsilyl-2'-O-[N,N-dimethylaminooxyethyl]-5-methyluridine as a white foam (14.6 g, 80%).

2'-O-(dimethylaminooxyethyl)-5-methyluridine

Triethylamine trihydrofluoride (3.91 mL, 24.0 mmol) was dissolved in dry THF and triethylamine (1.67 mL, 12 mmol, dry, kept over KOH). This mixture of triethylamine-2HF was then added to 5'-O-tert-butyldiphenylsilyl-2'-O-[N,N-dimethylaminooxyethyl]-5-methyluridine (1.40 g, 2.4 mmol) and stirred at room temperature for 24 hrs. Reaction was monitored by TLC (5% MeOH in $CH_2Cl_2$). Solvent was removed under vacuum and the residue placed on a flash column and eluted with 10% MeOH in $CH_2Cl_2$ to get 2'-O-(dimethylaminooxyethyl)-5-methyluridine (766 mg, 92.5%).

5'-O-DMT-2'-O-(dimethylaminooxyethyl)-5-methyluridine

2'-O-(dimethylaminooxyethyl)-5-methyluridine (750 mg, 2.17 mmol) was dried over $P_2O_5$ under high vacuum overnight at 40° C. It was then co-evaporated with anhydrous pyridine (20 mL). The residue obtained was dissolved in pyridine (11 mL) under argon atmosphere. 4-dimethylaminopyridine (26.5 mg, 2.60 mmol), 4,4'-dimethoxytrityl chloride (880 mg, 2.60 mmol) was added to the mixture and the reaction mixture was stirred at room temperature until all of the starting material disappeared. Pyridine was removed under vacuum and the residue chromatographed and eluted with 10% MeOH in $CH_2Cl_2$ (containing a few drops of pyridine) to get 5'-O-DMT-2'-O-(dimethylamino-oxyethyl)-5-methyluridine (1.13 g, 80%).

5'-O-DMT-2'-O-(2-N,N-dimethylamixiooxyethyl)-5-methyluridine-3'-[(2-cyanoethyl)-N,N-diisopropylphosphoramidite]

5'-O-DMT-2'-O-(dimethylaminooxyethyl)-5-methyluridine (1.08 g, 1.67 mmol) was co-evaporated with toluene (20 mL). To the residue N,N-diisopropylamine tetrazonide (0.29 g, 1.67 mmol) was added and dried over $P_2O_5$ under high vacuum overnight at 40° C. Then the reaction mixture was dissolved in anhydrous acetonitrile (8.4 mL) and 2-cyanoethyl-N,N,$N^1$,$N^1$-tetraisopropylphosphoramidite (2.12 mL, 6.08 mmol) was added. The reaction mixture was stirred at ambient temperature for 4 hrs under inert atmosphere. The progress of the reaction was monitored by TLC (hexane:ethyl acetate 1:1). The solvent was evaporated, then the residue was dissolved in ethyl acetate (70 mL) and washed with 5% aqueous $NaHCO_3$ (40 mL). Ethyl acetate layer was dried over anhydrous $Na_2SO_4$ and concentrated. Residue obtained was chromatographed (ethyl acetate as eluent) to get 5'-O-DMT-2'-O-(2-N,N-dimethylaminooxyethyl)-5-methyluridine-3-[(2-cyanoethyl)-N,N-diisopropylphosphoramidite] as a foam (1.04 g, 74.9%).

2'-(Aminooxyethoxy)nucleoside amidites

2'-(Aminooxyethoxy) nucleoside amidites [also known in the art as 2'-O-(aminooxyethyl) nucleoside amidites] are prepared as described in the following paragraphs. Adenosine, cytidine and thymidine nucleoside amidites are prepared similarly.

N2-isobutyryl-6-O-diphenylcarbamoyl-2'-O-(2-ethylacetyl)-5'-O-(4,4'-dimethoxyrtrityl)guanosine-3'-[(2-cyanoethyl)-N,N-diisopropylphosphoramidite]

The 2'-O-aminooxyethyl guanosine analog may be obtained by selective 2'-O-alkylation of diaminopurine riboside. Multigram quantities of diaminopurine riboside may be purchased from Schering AG (Berlin) to provide 2'-O-(2-ethylacetyl) diaminopurine riboside along with a minor amount of the 3'-O-isomer. 2'-O-(2-ethylacetyl) diaminopurine riboside may be resolved and converted to 2'-O-(2-ethylacetyl)guanosine by treatment with adenosine deaminase. (McGee, D. P. C., Cook, P. D., Guinosso, C. J., WO 94/02501 A1 940203.) Standard protection procedures should afford 2'-O-(2-ethylacetyl)-5'-O-(4,4'-dimethoxytrityl)guanosine and 2-N-isobutyryl-6-O-diphenylcarbamoyl-2'-O-(2-ethylacetyl)-5'-O-(4,4'-dimethoxytrityl)guanosine which may be reduced to provide 2-N-isobutyryl-6-O-diphenylcarbamoyl-2'-O-(2-hydroxyethyl)-5'-O-(4,4'-dimethoxytrityl)guanosine. As before the hydroxyl group may be displaced by N-hydroxyphthalimide via a Mitsunobu reaction, and the protected nucleoside may phosphitylated as usual to yield 2-N-isobutyryl-6-O-diphenylcarbamoyl-2'-O-([2-phthalmidoxy]ethyl)-5'-O-(4,4'-dimethoxytrityl)guanosine-3'-[(2-cyanoethyl)-N,N-diisopropylphosphoramidite].

2'-dimethylaminoethoxyethoxy (2'-DXAEOE)nucleoside amidites

2'-dimethylaminoethoxyethoxy nucleoside amidites (also known in the art as 2'-O-dimethylaminoethoxyethyl, i.e., 2'-O—$CH_2$—O—$CH_2$—$N(CH_2)_2$, or 2'-DMAEOE nucleoside amidites) are prepared as follows. Other nucleoside amidites are prepared similarly.

2'-O-[2(2-N,N-dimethylaminoethoxy)ethyl]-5-methyl uridine

2[2-(Dimethylamino)ethoxy]ethanol (Aldrich, 6.66 g, 50 mmol) is slowly added to a solution of borane in tetrahydrofuran (1 M, 10 mL, 10 mmol) with stirring in a 100 mL bomb. Hydrogen gas evolves as the solid dissolves. $O^2$-, 2'-anhydro-5-methyluridine (1.2 g, 5 mmol), and sodium bicarbonate (2.5 mg) are added and the bomb is sealed, placed in an oil bath and heated to 155° C. for 26 hours. The bomb is cooled to room temperature and opened. The crude solution is concentrated and the residue partitioned between water (200 mL) and hexanes (200 mL). The excess phenol is extracted into the hexane layer. The aqueous layer is extracted with ethyl acetate (3×200 mL) and the combined organic layers are washed once with water, dried over anhydrous sodium sulfate and concentrated. The residue is columned on silica gel using methanol/methylene chloride 1:20 (which has 2% triethylamine) as the eluent. As the column fractions are concentrated a colorless solid forms which is collected to give the title compound as a white solid.

5'-O-dimethoxytrityl-2'-O-(2(2-N,N-dimethylaminoethoxy)ethyl)]-5-methyl uridine

To 0.5 g (1.3 mmol) of 2'-O-[2(2-N,N-dimethylaminoethoxy)ethyl)]-5-methyl uridine in anhydrous pyridine (8 mL), triethylamine (0.36 mL) and dimethoxytrityl chloride (DMT-Cl, 0.87 g, 2 eq.) are added and stirred for 1 hour. The reaction mixture is poured into water (200 mL) and extracted with $CH_2Cl_2$ (2×200 mL). The combined $CH_2Cl_2$ layers are washed with saturated $NaHCO_3$ solution, followed by saturated NaCl solution and dried over anhydrous sodium sulfate. Evaporation of the solvent followed by silica gel chromatography using MeOH:$CH_2Cl_2$:$Et_3N$ (20:1, v/v, with 1% triethylamine) gives the title compound.

5'-O-Dimethoxytrityl-2'-O-[2(2-N,N-dimethylaminoethoxy)-ethyl)]-5-methyl uridine-3'-O-(cyanoethyl-N,N-diisopropyl)phosphoramidite Diisopropylaminotetrazolide (0.6 g) and 2-cyanoethoxy-N,N-diisopropyl phosphoramidite (1.1 mL, 2 eq.) are added to a solution of 5'-O-dimethoxytrityl-2'-O-[2(2-N,N-dimethylaminoethoxy)ethyl)]-5-methyluridine (2.17 g, 3 mmol) dissolved in $CH_2Cl_2$ (20 mL) under an atmosphere of argon. The reaction mixture is stirred overnight and the solvent evaporated. The resulting residue is purified by silica gel flash column chromatography with ethyl acetate as the eluent to give the title compound.

Example 2
Oligonucleotide Synthesis

Unsubstituted and substituted phosphodiester (P=O) oligonucleotides are synthesized on an automated DNA synthesizer (Applied Biosystems model 380D) using standard phosphoramidite chemistry with oxidation by iodine.

Phosphorothioates (P=S) are synthesized as for the phosphodiester oligonucleotides except the standard oxidation bottle was replaced by 0.2 M solution of 3H-1,2-benzodithiole-3-one 1,1-dioxide in acetonitrile for the stepwise thiation of the phosphite linkages. The thiation wait step was increased to 68 sec and was followed by the capping step. After cleavage from the CPG column and deblocking in concentrated ammonium hydroxide at 55° C. (18 h), the oligonucleotides were purified by precipitating twice with 2.5 volumes of ethanol from a 0.5 M NaCl solution.

Phosphinate oligonucleotides are prepared as described in U.S. Pat. No. 5,508,270, herein incorporated by reference.

Alkyl phosphonate oligonucleotides are prepared as described in U.S. Pat. No. 4,469,863, herein incorporated by reference.

3'-Deoxy-3'-methylene phosphonate oligonucleotides are prepared as described in U.S. Pat. Nos. 5,610,289 or 5,625,050, herein incorporated by reference.

Phosphoramidite oligonucleotides are prepared as described in U.S. Pat. No. 5,256,775 or U.S. Pat. No. 5,366,878, herein incorporated by reference.

Alkylphosphonothioate oligonuclectides are prepared as described in published PCT applications PCT/US94/00902 and PCT/US93/06976 (published as WO 94/17093 and WO 94/02499, respectively), herein incorporated by reference.

3'-Deoxy-3'-amino phosphoramidate oligonucleotides are prepared as described in U.S. Pat. No. 5,476,925, herein incorporated by reference.

Phosphotriester oligonucleotides are prepared as described in U.S. Pat. No. 5,023,243, herein incorporated by reference.

Borano phosphate oligonucleotides are prepared as described in U.S. Pat. Nos. 5,130,302 and 5,177,198, both herein incorporated by reference.

Example 3
Oligonucleoside Synthesis

Methylenemethylimino linked oligonucleosides, also identified as MMI linked oligonucleosides, methylenedimethyl-hydrazo linked oligonucleosides, also identified as MDH linked oligonucleosides, and methylenecarbonylamino linked oligonucleosides, also identified as amide-3 linked oligonucleosides, and methyleneaminocarbonyl linked oligonucleosides, also identified as amide-4 linked oligonucleosides, as well as mixed backbone compounds having, for instance, alternating MMI and P=O or P=S linkages are prepared as described in U.S. Pat. Nos. 5,378,825, 5,386,023, 5,489,677, 5,602,240 and 5,610,289, all of which are herein incorporated by reference.

Formacetal and thioformacetal linked oligonucleosides are prepared as described in U.S. Pat. Nos. 5,264,562 and 5,264,564, herein incorporated by reference.

Ethylene oxide linked oligonucleosides are prepared as described in U.S. Pat. Nos. 5,223,618, herein incorporated by reference.

Example 4
PNA Synthesis

Peptide nucleic acids (PNAs) are prepared in accordance with any of the various procedures referred to in Peptide Nucleic Acids (PNA): Synthesis, Properties and Potential Applications, *Bioorganic & Medicinal Chemistry*, 1996, 4, 5–23. They may also be prepared in accordance with U.S. Pat. Nos. 5,539,082, 5,700,922, and 5,719,262, herein incorporated by reference.

Example 5
Synthesis of Chimeric Oligonucleotides

Chimeric oligonucleotides, oligonucleosides or mixed oligonucleotides/oligonucleosides of the invention can be of several different types. These include a first type wherein the "gap" segment of linked nucleosidies is positioned between 5' and 3' "wing" segments of linked nucleosides and a second "open end" type wherein the "gap" segment is located at either the 3' or the 5' terminus of the oligomeric compound. Oligonucleotides of the first type are also known in the art as "gapmers" or gapped oligonucleotides. Oligonucleotides of the second type are also known in the art as "hemimers" or "wingmers".

[2'-O-Me]—[2'-deoxy]—[2'-O-Me] Chimeric Phosphorothioate Oligonucleotides

Chimeric oligonucleotides having 2'-O-alkyl phosphorothioate and 2'-deoxy phosphorothioate oligonucleotide segments are synthesized using an Applied Biosystems automated DNA synthesizer Model 380B, as above. Oligonucleotides are synthesized using the automated synthesizer and 2'-deoxy-5'-dimethoxytrityl-3'-O-phosphoramidite for the DNA portion and 5'-dimethoxytrityl-2'-O-methyl-3'-O-phosphoramidite for 5' and 3' wings. The standard synthesis cycle is modified by increasing the wait step after the delivery of tetrazole and base to 600 s repeated four times for RNA and twice for 2'-O-methyl. The fully protected oligonucleotide is cleaved from the support and the phosphate group is deprotected in 3:1 ammonia/ethanol at room temperature overnight then lyophilized to dryness. Treatment in methanolic ammonia for 24 hrs at room temperature is then done to deprotect all bases and sample was again lyophilized to dryness. The pellet is resuspended in 1M TBAF in THF for 24 hrs at room temperature to deprotect the 2' positions. The reaction is then quenched with 1M TEAA and the sample is then reduced to ½ volume by rotovac before being desalted on a G25 size exclusion column. The oligo recovered is then analyzed spectrophotometrically for yield and for purity by capillary electrophoresis and by mass spectrometry.

[2'-O-(2-Methoxyethyl)]—[2'-deoxy]—[2'-O-(Methoxyethyl)] Chimeric Phosphorothioate Oligonucleotides

[2'-O-(2-methoxyethyl)]—[2'-deoxy]—[-2'-O-(methoxyethyl)] chimeric phosphorothioate oligonucleotides were prepared as per the procedure above for the 2'-O-methyl chimeric oligonucleotide, with the substitution of 2'-O-(methoxyethyl) amidites for the 2'-O-methyl amidites.

[2'-O-(2-Methoxyethyl)Phosphodiester]—[2'-deoxy Phosphorothioate]—[2'-O-(2-Methoxyethyl) Phosphodiester] Chimeric Oligonucleotides

[2'-O-(2-methoxyethyl phosphodiester]—[2'-deoxy phosphorothioate]—[2'-O-(methoxyethyl) phosphodiester] chimeric oligonucleotides are prepared as per the above procedure for the 2'-O-methyl chimeric oligonucleotide with the substitution of 2'-O-(methoxyethyl) amidites for the 2'-O-methyl amidites, oxidization with iodine to generate the phosphodiester internucleotide linkages within the wing portions of the chimeric structures and sulfurization utilizing 3,H-1,2 benzodithiole-3-one 1,1 dioxide (Beaucage Reagent) to generate the phosphorothioate internucleotide linkages for the center gap.

Other chimeric oligonucleotides, chimeric oligonucleosides and mixed chimeric oligonucleotides/oligonucleosides are synthesized according to U.S. Pat. No. 5,623,065, herein incorporated by reference.

Example 6
Oligonucleotide Isolation

After cleavage from the controlled pore glass column (Applied Biosystems) and deblocking in concentrated ammonium hydroxide at 55° C. for 18 hours, the oligonucleotides or oligonucleosides are purified by precipitation twice out of 0.5 M NaCl with 2.5 volumes ethanol. Synthesized oligonucleotides were analyzed by polyacrylamide gel electrophoresis on denaturing gels and judged to be at least 85% full length material. The relative amounts of phosphorothioate and phosphodiester linkages obtained in synthesis were periodically checked by $^{31}$P nuclear magnetic resonance spectroscopy, and for some studies oligonucleotides were purified by HPLC, as described by Chiang et al., J. Biol. Chem. 1991, 266, 18162–18171. Results obtained with HPLC-purified material were similar to those obtained with non-HPLC purified material.

Example 7
Oligonucleotide Synthesis—96 Well Plate Format

Oligonucleotides were synthesized via solid phase P(III) phosphoramidite chemistry on an automated synthesizer capable of assembling 96 sequences simultaneously in a standard 96 well format. Phosphodiester internucleotide linkages were afforded by oxidation with aqueous iodine. Phosphorothioate internucleotide linkages were generated by sulfurization utilizing 3,H-1,2 benzodithiole-3-one 1,1 dioxide (Beaucage Reagent) in anhydrous acetonitrile. Standard base-protected beta-cyanoethyldiisopropyl phosphoramidites were purchased from commercial vendors (e.g. PE-Applied Biosystems, Foster City, Calif., or Pharmacia, Piscataway, N.J.). Non-standard nucleosides are synthesized as per known literature or patented methods. They are utilized as base protected beta-cyanoethyldiisopropyl phosphoramidites.

Oligonucleotides were cleaved from support and deprotected with concentrated NH$_4$OH at elevated temperature (55–60° C.) for 12–16 hours and the released product then dried in vacuo. The dried product was then re-suspended in sterile water to afford a master plate from which all analytical and test plate samples are then diluted utilizing robotic pipettors.

Example 8
Oligonucleotide Analysis—96 Well Plate Format

The concentration of oligonucleotide in each well was assessed by dilution of samples and UV absorption spectroscopy. The full-length integrity of the individual products was evaluated by capillary electrophoresis (CE) in either the 96 well format (Beckman P/ACE™ MDQ) or, for individually prepared samples, on a commercial CE apparatus (e.g., Beckman P/ACE™ 5000, ABI 270). Base and backbone composition was confirmed by mass analysis of the compounds utilizing electrospray-mass spectroscopy. All assay test plates were diluted from the master plate using single and multi-channel robotic pipettors. Plates were judged to be acceptable if at least 85% of the compounds on the plate were at least 85% full length.

Example 9
Cell Culture and Oligonucleotide Treatment

The effect of antisense compounds on target nucleic acid expression can be tested in any of a variety of cell types provided that the target nucleic acid is present at measurable levels. This can be routinely determined using, for example, PCR or Northern blot analysis. The following 5 cell types are provided for illustrative purposes, but other cell types can be routinely used, provided that the target is expressed in the cell type chosen. This can be readily determined by methods routine in the art, for example Northern blot analysis, Ribonuclease protection assays, or RT-PCR.

T-24 Cells

The human transitional cell bladder carcinoma cell line T-24 was obtained from the American Type Culture Collection (ATCC) (Manassas, Va.). T-24 cells were routinely cultured in complete McCoy's 5A basal media (Invitrogen Corporation, Carlsbad, Calif.) supplemented with 10% fetal calf serum ((Invitrogen Corporation, Carlsbad, Calif.), penicillin 100 units per mL, and streptomycin 100 micrograms per mL (Invitrogen Corporation, Carlsbad, Calif.). Cells were routinely passaged by trypsinization and dilution when they reached 90% confluence. Cells were seeded into 96-well plates (Falcon-Primaria #3872) at a density of 7000 cells/well for use in RT-PCR analysis.

For Northern blotting or other analysis, cells may be seeded onto 100 mm or other standard tissue culture plates and treated similarly, using appropriate volumes of medium and oligonucleotide.

A549 Cells

The human lung carcinoma cell line A549 was obtained from the American Type Culture Collection (ATCC) (Manassas, Va.). A549 cells were routinely cultured in DMEM basal media (Invitrogen Corporation, Carlsbad, Calif.) supplemented with 10% fetal calf serum (Invitrogen Corporation, Carlsbad, Calif.), penicillin 100 units per mL, and streptomycin 100 micrograms per mL (Invitrogen Corporation, Carlsbad, Calif.). Cells were routinely passaged by trypsinization and dilution when they reached 90% confluence.

NHDF Cells

Human neonatal dermal fibroblast (NHDF) were obtained from the Clonetics Corporation (Walkersville, Md.). NHDFs were routinely maintained in Fibroblast Growth Medium (Clonetics Corporation, Walkersville, Md.) supplemented as recommended by the supplier. Cells were maintained for up to 10 passages as recommended by the supplier.

HEK Cells

Human embryonic keratinocytes (HEK) were obtained from the Clonetics Corporation (Walkersville, Md.). HEKs were routinely maintained in Keratinocyte Growth Medium (Clonetics Corporation, Walkersville, Md.) formulated as recommended by the supplier. Cells were routinely maintained for up to 10 passages as recommended by the supplier.

HepG2 Cells

The human hepatoblastoma cell line HepG2 was obtained from the American Type Culture Collection (Manassas, Va.). HepG2 cells were routinely cultured in Eagle's MEM supplemented with 10% fetal calf serum, non-essential amino acids, and 1 mM sodium pyruvate (Gibco/Life Technologies, Gaithersburg, Md.). Cells were routinely passaged by trypsinization and dilution when they reached 90% confluence. Cells were seeded into 96-well plates (Falcon-Primaria #3872) at a density of 7000 cells/well for use in RT-PCR analysis.

For Northern blotting or other analyses, cells may be seeded onto 100 mm or other standard tissue culture plates and treated similarly, using appropriate volumes of medium and oligonucleotide.

Treatment with Antisense Compounds

When cells reached 70% confluenczy, they were treated with oligonucleotide. For cells grown in 96-well plates, wells were washed once with 100 µL OPTI-MEM™-1 reduced-serum medium (Invitrogen Corporation, Carlsbad, Calif.) and then treated with 130 µL of OPTI-MEM™-1 containing 3.75 µg/mL LIPOFECTIN™ (Invitrogen Corporation, Carlsbad, Calif.) and the desired concentration of oligonucleotide. After 4–7 hours of treatment, the medium was replaced with fresh medium. Cells were harvested 16–24 hours after oligonucleotide treatment.

The concentration of oligonucleotide used varies from cell line to cell line. To determine the optimal oligonucleotide concentration for a particular cell line, the cells are treated with a positive control oligonucleotide at a range of concentrations. For human cells the positive control oligonucleotide is ISIS 13920, TCCGTCATCGCTCCTCAGGG, SEQ ID NO: 1, a 2'-O-methoxyethyl gaprner (2'-O-methoxyethyls shown in bold) with a phosphorothioate backbone which is targeted to human H-ras. For mouse or rat cells the positive control oligonucleotide is ISIS 15770, ATGCATTCTGCCCCCAAGGA, SEQ ID NO: 2, a 2'-O-methoxyethyl gapier (2'-O-methoxyethyls shown in bold) with a phosphorothioate backbone which is targeted to both mouse and rat c-raf. The concentration of positive control oligonucleotide that results in 80% inhibition of c-Ha-ras (for ISIS 13920) or c-raf (for ISIS 15770) mRNA is then utilized as the screening concentration for new oligonucleotides in subsequent experiments for that cell line. If 80% inhibition is not achieved, the lowest concentration of positive control oligonucleotide that results in 60% inhibition of H-ras or c-raf mRNA is then utilized as the oligonucleotide screening concentration in subsequent experiments for that cell line. If 60% inhibition is not achieved, that particular cell line is deemed as unsuitable for oligonucleotide transfection experiments.

Example 10

Analysis of Oligonucleotide Inhibition of CD36L1 Expression

Antisense modulation of CD36L1 expression can be assayed in a variety of ways known in the art. For example, CD36L1 mRNA levels can be quantitated by, e.g., Northern blot analysis, competitive polymerase chain reaction (PCR), or real-time PCR (RT-PCR). Real-time quantitative PCR is presently preferred. RNA analysis can be performed on total cellular RNA or poly(A)+mRNA. The preferred method of RNA analysis of the present invention is the use of total cellular RNA as described in other examples herein. Methods of RNA isolation are taught in, for example, Ausubel, F. M. et al., Current Protocols in Molecular Biology, Volume 1, pp. 4.1.1–4.2.9 and 4.5.1–4.5.3, John Wiley & Sons, Inc., 1993. Northern blot analysis is routine in the art and is taught in, for example, Ausubel, F. M. et al., Current Protocols in Molecular Biology, Volume 1, pp. 4.2.1–4.2.9, John Wiley & Sons, Inc., 1996. Real-time quantitative (PCR) can be conveniently accomplished using the commercially available ABI PRISM™ 7700 Sequence Detection System, available from PE-Applied Biosystems, Foster City, Calif. and used according to manufacturer's instructions.

Protein levels of CD36L1 can be quantitated in a variety of ways well known in the art, such as immunoprecipitation, Western blot analysis (immunoblotting), ELISA or fluorescence-activated cell sorting (FACS). Antibodies directed to CD36L1 can be identified and obtained from a variety of sources, such as the MSRS catalog of antibodies (Aerie Corporation, Birmingham, Mich.), or can be prepared via conventional antibody generation methods. Methods for preparation of polyclonal antisera are taught in, for example, Ausubel, F. M. et al., Current Protocols in Molecular Biology, Volume 2, pp. 11.12.1–11.12.9, John Wiley & Sons, Inc., 1997. Preparation of monoclonal antibodies is taught in, for example, Ausubel, F. M. et al., Current Protocols in Molecular Biology, Volume 2, pp. 11.4.1–11.11.5, John Wiley & Sons, Inc., 1997.

Immunoprecipitation methods are standard in the art and can be found at, for example, Ausubel, F. M. et al., Current Protocols in Molecular Biology, Volume 2, pp. 10.16.1–10.16.11, John Wiley & Sons, Inc., 1998. Western blot (immunoblot) analysis is standard in the art and can be found at, for example, Ausubel, F. M. et al., Current Protocols in Molecular Biology, Volume 2, pp. 10.8.1–10.8.21, John Wiley & Sons, Inc., 1997. Enzyme-linked immunosorbent assays (ELISA) are standard in the art and can be found at, for example, Ausubel, F. M. et al., Current Protocols in Molecular Biology, Volume 2, pp. 11.2.1–11.2.22, John Wiley & Sons, Inc., 1991.

Example 11

Poly(A)+mRNA Isolation

Poly(A)+mRNA was isolated according to Miura et al., Clin. Chem., 1996, 42, 1758–1764. Other methods for poly(A)+mRNA isolation are taught in, for example, Ausubel, F. M. et al., Current Protocols in Molecular Biology, Volume 1, pp. 4.5.1–4.5.3, John Wiley & Sons, Inc., 1993. Briefly, for cells grown on 96-well plates, growth medium was removed from the cells and each well was washed with 200 µL cold PBS. 60 µL lysis buffer (10 mM Tris-HCl, pH 7.6, 1 mM EDTA, 0.5 M NaCl, 0.5% NP-40, 20 mM vanadyl-ribonucleoside complex) was added to each well, the plate was gently agitated and then incubated at room temperature for five minutes. 55 µL of lysate was transferred to Oligo d(T) coated 96-well plates (AGCT Inc., Irvine Calif.). Plates were incubated for 60 minutes at room temperature, washed 3 times with 200 µL of wash buffer (10 mM Tris-HCl pH 7.6, 1 mM EDTA, 0.3 M NaCl). After the final wash, the plate was blotted on paper towels to remove excess wash buffer and then air-dried for 5 minutes. 60 µL of elution buffer (5 mM Tris-HCl pH 7.6), preheated to 70° C. was added to each well, the plate was incubated on a 90° C. hot plate for 5 minutes, and the eluate was then transferred to a fresh 96-well plate.

Cells grown on 100 mm or other standard plates may be treated similarly, using appropriate volumes of all solutions.

Example 12

Total RNA Isolation

Total RNA was isolated using an RNEASY 96™ kit and buffers purchased from Qiagen Inc. (Valencia, Calif.) following the manufacturer's recommended procedures. Briefly, for cells grown on 96-well plates, growth medium was removed from the cells and each well was washed with 200 µL cold PBS. 150 µL Buffer RLT was added to each well and the plate vigorously agitated for 20 seconds. 150 µL of 70% ethanol was then added to each well and the contents mixed by pipetting three times up and down. The samples were then transferred to the RNEASY 96™ well plate attached to a QLAVAC™ manifold fitted with a waste collection tray and attached to a vacuum source. Vacuum was applied for 1 minute. 500 µL of Buffer RW1 was added to each well of the RNEASY 96™ plate and incubated for 15 minutes and the vacuum was again applied for 1 minute. An additional 500 µL of Buffer RW1 was added to each well of the RNEASY 96™ plate and the vacuum was applied for 2 minutes. 1 mL of Buffer RPE was then added to each well of the RNEASY 96™ plate and the vacuum applied for a period of 90 seconds. The Buffer RPE wash was then repeated and the vacuum was applied for an additional 3 minutes. The plate was then removed from the QIAVAC™ manifold and blotted dry on paper towels. The plate was then re-attached to the QIAVAC™ manifold fitted with a collection tube rack containing 1.2 mL collection tubes. RNA was then eluted by pipetting 170 µL water into each well, incubating 1 minute, and then applying the vacuum for 3 minutes.

The repetitive pipetting and elution steps may be automated using a QIAGEN Bio-Robot 9604 (Qiagen, Inc., Valencia Calif.). Essentially, after lysing of the cells on the culture plate, the plate is transferred to the robot deck where the pipetting, DNase treatment and elution steps are carried out.

Example 13
Real-Time Quantitative PCR Analysis of CD36L1 mRNA Levels

Quantitation of CD36L1 mRNA levels was determined by real-time quantitative PCR using the ABI PRISM™ 7700 Sequence Detection System (PE-Applied Biosystems, Foster City, Calif.) according to manufacturer's instructions. This is a closed-tube, non-gel-based, fluorescence detection system which allows high-throughput quantitation of polymerase chain reaction (PCR) products in real-time. As opposed to standard PCR, in which amplification products are quantitated after the PCR is completed, products in real-time quantitative PCR are quantitated as they accumulate. This is accomplished by including in the PCR reaction an oligonucleotide probe that anneals specifically between the forward and reverse PCR primers, and contains two fluorescent dyes. A reporter dye (e.g., FAM, obtained from either Operon Technologies Inc., Alameda, Calif. or Integrated DNA Technologies Inc., Coralville, Iowa) is attached to the 5' end of the probe and a quencher dye (e.g., TAMRA, obtained from either Operon Technologies Inc., Alameda, Calif. or Integrated DNA Technologies Inc., Coralville, Iowa) is attached to the 3' end of the probe. When the probe and dyes are intact, reporter dye emission is quenched by the proximity of the 3' quencher dye. During amplification, annealing of the probe to the target sequence creates a substrate that can be cleaved by the 5'-exonuclease activity of Taq polymerase. During the extension phase of the PCR amplification cycle, cleavage of the probe by Taq polymerase releases the reporter dye from the remainder of the probe (and hence from the quencher moiety) and a sequence-specific fluorescent signal is generated. With each cycle, additional reporter dye molecules are cleaved from their respective probes, and the fluorescence intensity is monitored at regular intervals by laser optics built into the ABI PRISM™ 7700 Sequence Detection System. In each assay, a series of parallel reactions containing serial dilutions of mRNA from untreated control samples generates a standard curve that is used to quantitate the percent inhibition after antisense oligonucleotide treatment of test samples.

Prior to quantitative PCR analysis, primer-probe sets specific to the target gene being measured are evaluated for their ability to be "multiplexed" with a GAPDH amplification reaction. In multiplexing, both the target gene and the internal standard gene GAPDH are amplified concurrently in a single sample. In this analysis, mRNA isolated from untreated cells is serially diluted. Each dilution is amplified in the presence of primer-probe sets specific for GAPDH only, target gene only ("single-plexing"), or both (multiplexing). Following PCR amplification, standard curves of GAPDH and target mRNA signal as a function of dilution are generated from both the single-plexed and multiplexed samples. If both the slope and correlation coefficient of the GAPDH and target signals generated from the multiplexed samples fall within 10% of their corresponding values generated from the single-plexed samples, the primer-probe set specific for that target is deemed multiplexable. Other methods of PCR are also known in the art.

PCR reagents were obtained from Invitrogen, Carlsbad, Calif. RT-PCR reactions were carried out by adding 20 µL PCR cocktail (2.5×PCR buffer (—MgCl2), 6.6 mM MgCl2, 375 µM each of DATP, dCTP, dCTP and dGTP, 375 nM each of forward primer and reverse primer, 125 nM of probe, I Units RNAse inhibitor, 1.25 Units PLATINUM® Taq, 5 Units MuLV reverse transcriptase, and 2.5×ROX dye) to 96 well plates containing 30 µL total RNA solution. The RT reaction was carried out by incubation for 30 minutes at 48° C. Following a 10 minute incubation at 95° C. to activate the PLATINUM® Taq, 40 cycles of a two-step PCR protocol were carried out: 95° C. for 15 seconds (denaturation) followed by 60° C. for 1.5 minutes (annealing/extension).

Gene target quantities obtained by real time RT-PCR are normalized using either the expression level of GAPDH, a gene whose expression is constant, or by quantifying total RNA using RiboGreen™ (Molecular Probes, Inc. Eugene, Oreg.). GAPDH expression is quantified by real time RT-PCR, by being run simultaneously with the target, multiplexing, or separately. Total RNA is quantified using RiboGreen™ RNA quantification reagent from Molecular Probes. Methods of RNA quantification by RiboGreen™ are taught in Jones, L. J., et al, Analytical Biochemistry, 1998, 265, 368–374.

In this assay, 170 µL of RiboGreen™ working reagent (RiboGreen™ reagent diluted 1:350 in 10 mM Tris-HCl, 1 mM EDTA, pH 7.5) is pipetted into a 96-well plate containing 30 µL purified, cellular RNA. The plate is read in a CytoFluor 4000 (PE Applied Biosystems) with excitation at 480 nm and emission at 520 nm.

Probes and primers to human CD36L1 were designed to hybridize to a human CD36L1 sequence, using published sequence information (GenBank accession number NM_005505.1, incorporated herein as SEQ ID NO: 3). For human CD36L1 the PCR primers were:

forward primer: CTGGGCTCTTCACGGTGTTC (SEQ ID NO: 4)
reverse primer: TCAGCCCGTTCCACTTGTC (SEQ ID NO: 5) and the
PCR probe was: FAM-CCAGAACATCAGCAGGATCC ACCTCG-TAMRA (SEQ ID NO: 6) where FAM (PE-Applied Biosystems, Foster City, Calif.) is the fluorescent reporter dye) and TAMRA (PE-Applied Biosystems, Foster City, Calif.) is the quencher dye. For human GAPDH the PCR primers were:
forward primer: GAAGGTGAAGGTCGGAGTC(SEQ ID NO: 7)
reverse primer: GAAGATGGTGATGGGATTTC (SEQ ID NO: 8) and the PCR probe was: 5' JOE-CAAGCTTCCCGTTCTCAGCC-TAMRA 3' (SEQ ID NO: 9) where JOE (PE-Applied Biosystems, Foster City, Calif.) is the fluorescent reporter dye) and TAMRA (PE-Applied Biosystems, Foster City, Calif.) is the quencher dye.

Example 14
Northern Blot Analysis of CD36L1 mRNA Levels

Eighteen hours after antisense treatment, cell monolayers were washed twice with cold PBS and lysed in 1 mL RNAZOL™ (TEL-TEST "B" Inc., Friendswood, Tex.). Total RNA was prepared following manufacturer's recommended protocols. Twenty micrograms of total RNA was fractionated by electrophoresis through 1.2% agarose gels containing 1.1% formaldehyde using a MOPS buffer system (AMRESCO, Inc. Solon, Ohio). RNA was transferred from the gel to HYBOND™-N+ nylon membranes (Amersham Pharmacia Biotech, Piscataway, N.J.) by overnight capillary transfer using a Northern/Southern Transfer buffer system (TEL-TEST "B" Inc., Friendswood, Tex.). RNA transfer was confirmed by UV visualization. Membranes were fixed by UV cross-linking using a STRATALINKER™ UV Crosslinker 2400 (Stratagene, Inc, La Jolla, Calif.) and then probed using QUICKHYB™ hybridization solution (Stratagene, La Jolla, Calif.) using manufacturer's recommendations for stringent conditions.

To detect human CD36L1, a human CD36L1 specific probe was prepared by PCR using the forward primer CTGGGCTCTTCACGGTGTTC (SEQ ID NO: 4) and the reverse primer TCAGCCCGTTCCACTTGTC (SEQ ID NO: 5). To normalize for variations in loading and transfer efficiency membranes were stripped and probed for human glyceraldehyde-3-phosphate dehydrogenase (GAPDH) RNA (Clontech, Palo Alto, Calif.).

Hybridized membranes were visualized and quantitated using a PHOSPHORIMAGER™ and IMAGEQUANT™ Software V3.3 (Molecular Dynamics, Sunnyvale, Calif.). Data was normalized to GAPDH levels in untreated controls.

Example 15
Antisense Inhibition of Human CD36L1 Expression by Chimeric Phosphorothioate Oligonucleotides having 2'-MOE Wings and a Deoxy Gap In accordance with the present invention, a series of oligonucleotides were designed to target different regions of the human CD36L1 RNA, using published sequences (GenBank accession number NM_005505.1, representing CD36L1 mRNA, incorporated herein as SEQ ID NO: 3; GenBank accession number BF793747.1, representing a partial 3' untranslated region of CD36L1, incorporated herein as SEQ ID NO: 10; GenBank accession number BG770204.1, representing a partial 5' untranslated region of CD36L1, incorporated herein as SEQ ID NO: 11; GenBank accession number BG820695.1, representing a potential variant of CD36L1 that splices from exon 12 to exon 14, incorporated herein as SEQ ID NO: 12; and residues 1441000–1482321 of GenBank accession number NT_009459, representing a partial genomic sequence of CD36L1, the complement of which is incorporated herein as SEQ ID NO: 13). The oligonucleotides are shown in Table 1. "Target site" indicates the first (5'-most) nucleotide number on the particular target sequence to which the oligonucleotide binds. All compounds in Table 1 are chimeric oligonucleotides ("gapmers") 20 nucleotides in length, composed of a central "gap" region consisting of ten 2'-deoxynucleotides, which is flanked on both sides (5' and 3' directions) by five-nucleotide "wings". The wings are composed of 2'-methoxyethyl (2'-MOE) nucleotides. The internucleoside (backbone) linkages are phosphorothioate (P=S) throughout the oligonucleotide. All cytidine residues are 5-methylcytidines. The compounds were analyzed for their effect on human CD36L1 mRNA levels by quantitative real-time PCR as described in other examples herein. Data are averages from two experiments. If present, "N.D." indicates "no data".

TABLE 1

Inhibition of human CD36L1 mRNA levels by chimeric phosphorothioate oligonucleotides having 2'-MOE wings and a deoxy gap

| ISIS # | REGION | TARGET SEQ ID NO | TARGET SITE | SEQUENCE | % INHIB | SEQ ID NO |
|---|---|---|---|---|---|---|
| 199301 | 5'UTR | 3 | 19 | cagggctccgcgcctggcag | 42 | 14 |
| 199302 | Start Codon | 3 | 62 | ggagcagcccatgtctgcgc | 17 | 15 |
| 199303 | Start Codon | 3 | 69 | ctttggcggagcagcccatg | 13 | 16 |
| 199304 | Coding | 3 | 169 | acctgctgcttgatgagcga | 22 | 17 |
| 199305 | Coding | 3 | 305 | ctgcggcttctcgcccttca | 27 | 18 |
| 199306 | Coding | 3 | 336 | ccctgtacacgtagggcccg | 64 | 19 |
| 199307 | Coding | 3 | 344 | cctggactccctgtacacgt | 56 | 20 |
| 199308 | Coding | 3 | 370 | ttgttgaaggtgatgttgct | 0 | 21 |
| 199309 | Coding | 3 | 377 | gtcgttgttgttgaaggtga | 44 | 22 |
| 199310 | Coding | 3 | 389 | gaaggacacggtgtcgttgt | 47 | 23 |
| 199311 | Coding | 3 | 397 | tactcgaggaaggacacggt | 25 | 24 |
| 199312 | Coding | 3 | 461 | gggcatgacgatgtagtcgc | 11 | 25 |
| 199313 | Coding | 3 | 526 | atgatgagcttcagggtcat | 41 | 26 |
| 199314 | Coding | 3 | 572 | gcggttcatgaaggcacgtt | 24 | 27 |
| 199315 | Coding | 3 | 592 | cacatgatctcacccacagt | 5 | 28 |

TABLE 1-continued

Inhibition of human CD36L1 mRNA levels by chimeric phosphorothioate oligonucleotides having 2'-MOE wings and a deoxy gap

| ISIS # | REGION | TARGET SEQ ID NO | TARGET SITE | SEQUENCE | % INHIB | SEQ ID NO |
|---|---|---|---|---|---|---|
| 199316 | Coding | 3 | 606 | ggtccttgtagccccacatg | 34 | 29 |
| 199317 | Coding | 3 | 743 | gatcctgctgatgttctgga | 32 | 30 |
| 199318 | Coding | 3 | 764 | gttccacttgtccacgaggt | 36 | 31 |
| 199319 | Coding | 3 | 786 | agaagtcaaccttgctcagc | 0 | 32 |
| 199320 | Coding | 3 | 811 | atcatgttgcactgatcgga | 39 | 33 |
| 199321 | Coding | 3 | 817 | ccattgatcatgttgcactg | 13 | 34 |
| 199322 | Coding | 3 | 919 | gactccttgtacattagctt | 44 | 35 |
| 199323 | Coding | 3 | 1012 | cagaagccttcgttgggtgg | 4 | 36 |
| 199324 | Coding | 3 | 1025 | ctccaggcacgggcagaagc | 24 | 37 |
| 199325 | Coding | 3 | 1132 | aggccagtcaccgcttctgc | 26 | 38 |
| 199326 | Coding | 3 | 1147 | tcctggttagggtgcaggcc | 42 | 39 |
| 199327 | Coding | 3 | 1250 | aatgcctgcgacagatttca | 34 | 40 |
| 199328 | Coding | 3 | 1262 | cccagtttgtccaatgcctg | 29 | 41 |
| 199329 | Coding | 3 | 1286 | cggcaggaccacaggctcaa | 32 | 42 |
| 199330 | Coding | 3 | 1310 | cccgctctctgcaaaccaga | 0 | 43 |
| 199331 | Coding | 3 | 1400 | cgccaggaggacgtactggg | 7 | 44 |
| 199332 | Coding | 3 | 1460 | gcatttctcttggctccgga | 33 | 45 |
| 199333 | Coding | 3 | 1466 | taaatagcatttctcttggc | 18 | 46 |
| 199334 | Coding | 3 | 1517 | ggcctgaatggcctccttat | 3 | 47 |
| 199335 | Coding | 3 | 1539 | atgtcatcagggattcagaa | 13 | 48 |
| 199336 | Coding | 3 | 1568 | ttcctgcagcacagagccct | 47 | 49 |
| 199337 | Coding | 3 | 1575 | gttttgcttcctgcagcaca | 6 | 50 |
| 199338 | Stop Codon | 3 | 1588 | tcaggaccctacagttttgc | 23 | 51 |
| 199339 | 3'UTR | 3 | 1766 | cgcatgtgtgtatgtgtgcc | 3 | 52 |
| 199340 | 3'UTR | 3 | 1792 | tccctgagtgtctgcacaag | 19 | 53 |
| 199341 | 3'UTR | 3 | 1797 | ctccatccctgagtgtctgc | 0 | 54 |
| 199342 | 3'UTR | 3 | 1842 | agtgcttgttgacgagcctc | 14 | 55 |
| 199343 | 3'UTR | 3 | 1882 | tggtcagcctgtgggccacg | 32 | 56 |
| 199344 | 3'UTR | 3 | 1936 | aacgggacaggccaggctca | 44 | 57 |
| 199345 | 3'UTR | 3 | 1945 | caacggctgaacgggacagg | 22 | 58 |
| 199346 | 3'UTR | 3 | 1991 | acaccgggactgcagtgttt | 44 | 59 |
| 199347 | 3'UTR | 3 | 2092 | aaggccaaagctcgtgccag | 2 | 60 |
| 199348 | 3'UTR | 3 | 2136 | cgaggcctgtgtaaaggcgc | 18 | 61 |
| 199349 | 3'UTR | 3 | 2171 | tgcacagggcatcttgtgct | 22 | 62 |
| 199350 | 3'UTR | 3 | 2184 | accctcgggcagctgcacag | 54 | 63 |

TABLE 1-continued

Inhibition of human CD36L1 mRNA levels by chimeric phosphorothioate oligonucleotides having 2'-MOE wings and a deoxy gap

| ISIS # | REGION | TARGET SEQ ID NO | TARGET SITE | SEQUENCE | % INHIB | SEQ ID NO |
|---|---|---|---|---|---|---|
| 199351 | 3'UTR | 3 | 2235 | agtgcctgtgaagacttcgg | 47 | 64 |
| 199352 | 3'UTR | 3 | 2253 | cgccagacaacccgatgcag | 21 | 65 |
| 199353 | 3'UTR | 3 | 2296 | ctcagtccataggatgatgt | 37 | 66 |
| 199354 | 3'UTR | 3 | 2310 | cagagagtggccggctcagt | 42 | 67 |
| 199355 | 3'UTR | 3 | 2331 | cacagcctgcgccacttcgg | 21 | 68 |
| 199356 | 3'UTR | 3 | 2394 | tcacctcagcctgggcacct | 47 | 69 |
| 199357 | 3'UTR | 3 | 2445 | ggtttgccccagggtccagg | 44 | 70 |
| 199358 | 3'UTR | 3 | 2472 | tttctattccagtagaaaag | 1 | 71 |
| 199359 | 3'UTR | 3 | 2518 | tttattacttcaagagtgaa | 10 | 72 |
| 199360 | Exon: Exon Junction | 12 | 268 | cctcaggaccttggctccgg | 2 | 73 |
| 199361 | 3'UTR | 10 | 305 | tgtcacagaggcaggcatcc | 0 | 74 |
| 199362 | 3'UTR | 10 | 322 | acctcagcaaacaaggctgt | 4 | 75 |
| 199363 | 3'UTR | 10 | 614 | ccaggatttgtagataaatg | 5 | 76 |
| 199364 | 3'UTR | 10 | 657 | agagagcaaaggccttagaa | 5 | 77 |
| 199365 | 3'UTR | 10 | 804 | agtcccgggcacctaaatcc | 25 | 78 |
| 199366 | 3'UTR | 10 | 836 | caaatctgaattgcgcgacc | 3 | 79 |
| 199367 | 3'UTR | 10 | 841 | gtgttcaaatctgaattgcg | 30 | 80 |
| 199368 | 5'UTR | 11 | 76 | ggccagtggttttatgcccc | 0 | 81 |
| 199369 | 5'UTR | 11 | 84 | cggcaggtggccagtggttt | 12 | 82 |
| 199370 | 5'UTR | 11 | 132 | ccgcagaggcacggtggatc | 38 | 83 |
| 199371 | Exon: Intron Junction | 13 | 9971 | cggcacgtactgaacctgca | 5 | 84 |
| 199372 | Intron 9 | 13 | 20630 | tctaatgagcttccctgcta | 17 | 85 |
| 199373 | Intron 10 | 13 | 27548 | agaccagcctgggcaacata | 24 | 86 |
| 199374 | Intron: Exon Junction | 13 | 30274 | cccagtttgtctggaaataa | 39 | 87 |
| 199375 | Intron: Exon Junction | 13 | 31228 | tggccccgctctgaggagac | 17 | 88 |
| 199376 | Intron 12 | 13 | 32803 | ctgcagatcttatgttctgg | 36 | 89 |
| 199377 | Intron 13 | 13 | 38743 | ctctctctgtcgcccaggct | 32 | 90 |
| 199378 | Intron: Exon Junction | 13 | 39145 | cctcaggaccctgtgggagaa | 20 | 91 |

As shown in Table 1, SEQ ID NOs 14, 19, 20, 22, 23, 26, 31, 33, 35, 39, 49, 57, 59, 63, 64, 66, 67, 69, 70, 83, 87 and 89 demonstrated at least 35% inhibition of human CD36L1 expression in this assay and are therefore preferred. The target sites to which these preferred sequences are complementary are herein referred to as "active sites" and are therefore preferred sites for targeting by compounds of the present invention.

Example 16
Western Blot Analysis of CD36L1 Protein Levels

Western blot analysis (immunoblot: analysis) is carried out using standard methods. Cells are harvested 16–20 h after oligonucleotide treatment, washed once with PBS, suspended in Laemmli buffer (100 ul/well), boiled for 5 minutes and loaded on a 16% SDS-PAGE gel. Gels are run for 1.5 hours at 150 V, and transferred to membrane for western blotting. Appropriate primary antibody directed to CD36L1 is used, with a radiolabelled or fluorescently labeled secondary antibody directed against the primary antibody species. Bands are visualized using a PHOSPHO-RIMAGER™ (Molecular Dynamics, Sunnyvale Calif.).

What is claimed is:

1. A compound 8 to 50 nucleobases in length targeted to nucleobases 336 through 363 of a coding region of a nucleic acid molecule encoding CD36L1 (SEQ ID NO: 3), wherein said compound is an antisense oligonucleotide with at least one modified internucleoside linkage and specifically hybridizes with said region and inhibits the expression of CD36L1.

2. The compound of claim 1 wherein the modified internucleoside linkage is a phosphorothioate linkage.

3. The compound of claim 1 wherein the antisense oligonucleotide comprises at least one modified sugar moiety.

4. The compound of claim 3 wherein the modified sugar moiety is a 2'-o-methoxyethyl sugar moiety.

5. The compound of claim 1 wherein the antisense oiigonucleotide comprises at least one modified nucleobase.

6. The compound of claim 5 wherein the modified nucleobase is a 5-methylcytosine.

7. The compound of claim 1 wherein the antisense oligonucleotide is a chimeric oligonucleotide.

8. A composition comprising the compound of claim 1 and a pharmaceutically acceptable carrier or diluent.

9. The composition of claim 8 further comprising a colloidal dispersion system.

10. A method of inhibiting the expression of CD36L1 in cells or tissues comprising contacting said cells or tissues In vitro with the compound of claim 1 so that expression of CD36L1 is inhibited.

* * * * *